US011634502B2

(12) United States Patent
Yan et al.

(10) Patent No.: US 11,634,502 B2
(45) Date of Patent: *Apr. 25, 2023

(54) HETERODIMERIC BISPECIFIC ANTIBODIES

(71) Applicant: AMGEN INC., Thousand Oaks, CA (US)

(72) Inventors: Wei Yan, Sammamish, WA (US); Martin J. Pentony, Seattle, WA (US); Luis G. Borges, Redwood City, CA (US); Mark L. Michaels, Encino, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/774,320

(22) PCT Filed: Mar. 13, 2014

(86) PCT No.: PCT/US2014/026658
§ 371 (c)(1),
(2) Date: Sep. 10, 2015

(87) PCT Pub. No.: WO2014/151910
PCT Pub. Date: Sep. 25, 2014

(65) Prior Publication Data
US 2016/0115241 A1 Apr. 28, 2016

Related U.S. Application Data

(60) Provisional application No. 61/944,841, filed on Feb. 26, 2014, provisional application No. 61/791,357, filed on Mar. 15, 2013.

(51) Int. Cl.
*C07K 16/30* (2006.01)
*C07K 16/28* (2006.01)

(52) U.S. Cl.
CPC .......... *C07K 16/30* (2013.01); *C07K 16/2803* (2013.01); *C07K 16/2809* (2013.01); *C07K 2317/31* (2013.01); *C07K 2317/35* (2013.01); *C07K 2317/55* (2013.01); *C07K 2317/565* (2013.01); *C07K 2317/60* (2013.01); *C07K 2317/626* (2013.01); *C07K 2317/64* (2013.01); *C07K 2317/73* (2013.01); *C07K 2317/94* (2013.01)

(58) Field of Classification Search
CPC ............ C07K 16/2809; C07K 2317/31; C07K 2317/60; C07K 2317/64
USPC .......................................... 424/133.1, 136.1
See application file for complete search history.

(56) References Cited

U.S. PATENT DOCUMENTS

| | | | |
|---|---|---|---|
| 5,837,242 A | 11/1998 | Holliger et al. | |
| 7,037,784 B1 | 5/2006 | Hong | |
| 7,083,784 B2 | 8/2006 | Dall'Acqua et al. | |
| 7,371,827 B2 | 5/2008 | Goddard et al. | |
| 7,670,600 B2 | 3/2010 | Dall'Acqua et al. | |
| 7,695,936 B2 | 4/2010 | Carter et al. | |
| 2002/0004587 A1 | 1/2002 | Miller et al. | |
| 2003/0078385 A1 | 4/2003 | Arathoon et al. | |
| 2003/0114659 A1 | 6/2003 | Winter et al. | |
| 2004/0033561 A1 | 2/2004 | O'Keefe et al. | |
| 2004/0220388 A1* | 11/2004 | Mertens ................. | C07K 16/00 530/388.8 |
| 2007/0004909 A1 | 1/2007 | Johnson et al. | |
| 2007/0071675 A1 | 3/2007 | Wu et al. | |
| 2007/0105199 A1 | 5/2007 | Yan et al. | |
| 2009/0060910 A1 | 3/2009 | Johnson et al. | |
| 2009/0311253 A1 | 12/2009 | Ghayur et al. | |
| 2010/0150918 A1 | 6/2010 | Kufer et al. | |
| 2010/0174053 A1 | 7/2010 | Johnson et al. | |
| 2010/0183615 A1 | 7/2010 | Kufer et al. | |
| 2010/0234575 A1 | 9/2010 | Chamberlain et al. | |
| 2010/0286374 A1 | 11/2010 | Kannan et al. | |
| 2014/0024111 A1* | 1/2014 | Kannan ................. | C07K 16/468 435/328 |
| 2014/0308285 A1* | 10/2014 | Yan ....................... | C07K 16/468 424/136.1 |
| 2016/0038588 A1* | 2/2016 | Padhi ...................... | A61P 43/00 424/133.1 |
| 2016/0145340 A1* | 5/2016 | Borges ................... | C07K 16/28 424/136.1 |
| 2016/0257748 A1* | 9/2016 | Michaels ............... | C07K 16/28 |

(Continued)

FOREIGN PATENT DOCUMENTS

| | | |
|---|---|---|
| CA | 2150262 A1 | 6/1994 |
| EP | 2050764 A1 | 4/2009 |
| JP | 2009-504191 A | 2/2009 |

(Continued)

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*

(Continued)

*Primary Examiner* — Lynn A Bristol
(74) *Attorney, Agent, or Firm* — Marshall, Gerstein & Borun LLP

(57) ABSTRACT

Provided herein are heterodimeric bispecific antibodies that can mediate cytolysis of a target cell by an immune effector cell, nucleic acids encoding such antibodies, methods of making such antibodies, and methods of using such antibodies. These antibodies comprise two different polypeptide chains, each comprising two immunoglobulin variable regions and, optionally, a half life-extending moiety.

24 Claims, 22 Drawing Sheets

Specification includes a Sequence Listing.

(56) References Cited

U.S. PATENT DOCUMENTS

2020/0071425 A1* 3/2020 Yan .................. C07K 16/3069

FOREIGN PATENT DOCUMENTS

| JP | 2009-512453 A | 3/2009 |
| JP | 2011-508604 | 3/2011 |
| JP | 2012-504403 | 2/2012 |
| JP | 2012-512894 A | 6/2012 |
| JP | 2012-512894 | 7/2012 |
| WO | WO-2002/002781 A1 | 1/2002 |
| WO | WO 2004/003019 * | 6/2004 |
| WO | WO-2007/024715 A2 | 3/2007 |
| WO | WO-2007/048037 A2 | 4/2007 |
| WO | WO-2008/024188 A2 | 2/2008 |
| WO | WO-2008/157379 A2 | 12/2008 |
| WO | WO-2009/089004 A1 | 7/2009 |
| WO | WO-2010/037836 A2 | 4/2010 |
| WO | WO 2010/080538 | 7/2010 |
| WO | WO2010/080538 A1 | 7/2010 |
| WO | WO-2012/025530 A1 | 3/2012 |
| WO | WO-2012/116927 A1 | 9/2012 |
| WO | WO-2012/118903 A2 | 9/2012 |
| WO | WO-2012/125850 A1 | 9/2012 |
| WO | WO-2012/135345 A1 | 10/2012 |
| WO | WO-2013/096221 A1 | 6/2013 |
| WO | WO-2014/106015 A2 | 7/2014 |
| WO | WO-2014/145806 A2 | 9/2014 |

OTHER PUBLICATIONS

Song et al. (Biochem Biophys Res Comm 268:390-394 (2000)).*
Gunasekaran et al. (JBC 285(25):19637-19646 (Jun. 18, 2010)).*
Lui et al. (JBC 290(12):7535-7562 (Mar. 20, 2015)).*
Van Audenhove et al. (EBioMedicine 8 (2016) 40-48).*
Kim et al. (Biochimica et Biophysica Acta 1844 (2014) 1983-2001).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Worn and Pluckthun (J. Molec. Biol. 305( 5):989-1010 (2001)).*
Chen et al. (Adv Drug Deliv Rev. Oct. 15, 2013; 65(10): 1357-1369).*
Klein et al., Progress in overcoming the chain association issue in bispecific heterodimeric IgG antibodies. *MABS* 4(6): 653-63 (2012).
International Search Report issued in connection with International Application No. PCT/US2014/026658, European Patent Office, dated Jul. 9, 2014.
Bargou et al., Tumor regression in cancer patients by very low doses of a T cell-engaging antibody. *Science* 321(5891): 974-7 (2008).
Desmyter et al., Antigen specificity and high affinity binding provided by one single loop of a camel single-domain antibody. *J. Biol. Chem.* 276(28): 26285-90 (2001).
Edelman et al., The covalent structure of an entire gammaG immunoglobulin molecule. *Proc. Natl. Acad. Sci. USA* 63(1): 78-85 (1969).
Haas et al., Mode of cytotoxic action of T cell-engaging BiTE antibody MT110. *Immunobiology* 214(6): 441-53 (2009).
Holt et al., Domain antibodies: Proteins for therapy, *Trends in Biotechnology* 21(11): 484-90 (2003).
Honegger et al., Yet another numbering scheme for immunoglobulin variable domains: an automatic modeling and analysis tool. *J. Mol. Biol.* 309(3): 657-70 (2001).
Horton et al., Engineering hybrid genes without the use of restriction enzymes: gene splicing by overlap extension. *Gene* 77(1): 61-8 (1989).
Kabat et al., Sequences of Proteins of Immunological Interest, Public Health Service N.I.H. (1991).
Koide et al., The fibronectin type III domain as a scaffold for novel binding proteins. *J. Mol. Biol.* 284(4): 1141-51 (1998).
Laible et al., Genetic engineering of goats for the production of a biosimilar antibody in milk. *Reprod. Fertil. Dev.*25(1): 315 (2012).
Muyldermans, Single domain camel antibodies: current status. *J. Biotechnol.* 74(4): 277-302 (2001).
Panka et al., Variable region framework differences result in decreased or increased affinity of variant anti-digoxin antibodies. *Proc. Natl. Acad. Sci. USA* 85(9): 3080-4 (1988).
Paul (ed.), Fundamental Immunology. Raven Press, New York, 3rd ed. 292-5 (1993).
Rudikoff et al., *Proc. Natl. Acad. Sci. USA* 79: 1979 (1982).
Scheller et al., Production of spider silk proteins in tobacco and potato. *Nature Biotechnol.* 19(6): 573-7 (2001).
Streltsov et al., Structure of a shark IgNAR antibody variable domain and modeling of an early-developmental isotype. *Protein Sci.* 14(11): 2901-9 (2005).
Xu et al., In vitro characterization of five humanized OKT3 effector function variant antibodies. *Cell Immunol.* 200(1): 16-26 (2000).
Zhu et al., Production of human monoclonal antibody in eggs of chimeric chickens. *Nat. Biotechnol.* 23(9): 1159-69 (2005).
Wu et al., Simultaneous targeting of multiple disease mediators by a dual-variable-domain immunoglobulin, *Nature Biotechnology* 23(11): 1290-97 (2007).
Kumagai et al., Humanized bispecific antibodies recognizing lymphocytes and cancer cells, *Drug Delivery System* 23(5): 518-25 (2008).
Olafsen et al., Optimizing radiolabeled engineered anti-p185HER2 antibody fragments for in vivo imaging, *Cancer Res.* 65:5907-16 (2005).
U.S. Appl. No. 14/155,334.
U.S. Appl. No. 61/746,619.
Baeuerle et al., Bispecific T-cell engaging antibodies for cancer therapy, *Cancer Res.* 69:4941-4 (2009).
Hezereh et al., Effector Function Activities of a Panel of Mutants of a Broadly Neutralizing Antibody against Human Immunodeficiency Virus Type 1, *J. Virol.* 75:12161-8 (2001).
Holliger et al., "Diabodies": small bivalent and bispecific antibody fragments, *Proc. Natl. Acad. Sci. USA.* 90:6444-8 (1993).
Kontermann et al., Dual targeting strategies with bispecific antibodies, *MAbs.* 4:182-97 (2012).
Kontermann, R., Strategies to extend plasma half-lives of recombinant antibodies, *BioDrugs* 23:93-109 (2009).
Letter of the Patentee to the Examining Division filed on May 27, 2016 disclosed in EP2970484.
Letter of the Patentee to the Examining Division filed on Aug. 4, 2017 disclosed in EP2970484.
Ridgway et al., 'Knobs-into-holes' engineering of antibody CH3 domains for heavy chain heterodimerization, *Protein Eng.* 9:617-21 (1996).
Strohl W., Optimization of Fc-mediated effector functions of monoclonal antibodies, *Curr. Opin. Biotechnol.* 20:685-91 (2009).
D17 Word Document disclosed in EP2970484 concerning the amino acid sequences of the diabody disclosed in example 6.10 of D1.

* cited by examiner

HETERODIMERIC BISPECIFIC ANTIBODIES

CROSS REFERENCE TO RELATED APPLICATIONS

This application claims benefit of US Provisional Application Nos. 61/791,357, filed Mar. 15, 2013, and 61/944,841, filed Feb. 26, 2014, the contents of which are incorporated herein by reference in their entirety.

FIELD

The invention is in the field of antibody engineering.

BACKGROUND

Bispecific antibodies have a lot of promise as therapeutics in a variety of indications. Bispecific antibodies having a standard IgG format can be challenging to produce because they include four different polypeptide chains. The efficacy of a smaller, more easily-produced bispecific molecule has been clinically demonstrated in non-Hodgkin's lymphoma. See, e.g., Bargou et al. (2008), Science 321(5891): 974-977. Daily administration was used to achieve these results, presumably because of the short in vivo half life of this single chain molecule. Id. Hence, there is a need in the art for bispecific therapeutics with favorable pharmacokinetic properties, as well as therapeutic efficacy, ease of administration, and a format that makes them straightforward to produce.

SUMMARY

The bispecific heterodimeric antibody format described herein produces an antibody that can bind to one molecule of each of two different proteins and contains a half-life extending moiety, for example, an Fc region of an antibody. Thus, the bispecific antibody itself will not directly cause the multimerization of either of the proteins on a cell surface. Multimerization of certain proteins expressed on immune effector cells causes a generalized activation of the immune effector cell, a situation that could potentially cause undesirable, generalized inflammation. Since the Fc region can also bind to various other proteins, for example, the neonatal Fc receptor (FcRn), the bispecific heterodimeric antibodies described herein could be viewed as trispecific, although the binding specificity of an Fc region is not ordinarily recognized when designating an antibody as bispecific, trispecific, tetraspecific, etc. The antibody also can have favorable pharmacokinetic properties relative to a molecule lacking a half-life extending moiety. In some embodiments, one protein bound by the antibody is expressed on an immune effector cell, such as a T cell or an NK cell, and the other protein is expressed on a target cell, for example, a cancer cell. The bispecific heterodimeric antibodies described herein can have desirable pharmacokinetic properties and can bind to two specific proteins, one of which is expressed on an immune effector cell and the other of which is expressed on a diseased cell, such as a cancer cell. The binding of the bispecific heterodimeric antibody brings the immune effector cell and the target cell together, activates the immune cell, and induces the immune effector cell to eliminate the target cell, likely through a mechanism similar to that observed with some other bispecific antibodies. See, e.g., Hass et al. (2009), Immunobiology 214(6): 441-53.

In one aspect, provided herein is heterodimeric bispecific antibody comprising (a) a first polypeptide chain having the formula V1-L1-V2-L2-CH1, wherein V1 and V2 are immunoglobulin variable regions, L1 and L2 are linkers, L2 can be present or absent, and CH1 is a first immunoglobulin heavy chain constant region; and (b) a second polypeptide chain having the formula V3-L3-V4-L4-CL, wherein V3 and V4 are immunoglobulin variable regions, L3 and L4 are linkers, L4 can be present or absent, and CL is an immunoglobulin light chain constant region; wherein either or both of the first and the second polypeptide chains further comprise(s) a half life-extending moiety downstream from the regions represented by the formulas recited in (a) and (b); wherein V1, V2, V3, and V4 have different amino acid sequences; and wherein the heterodimeric bispecific antibody mediates cytolysis of a target cell displaying a target cell protein by an immune effector cell, but does not mediate the cytolysis of a cell that does not display a target cell protein by the immune effector cell and/or the heterodimeric antibody binds to a target cell and an immune effector cell. The half life-extending moiety can be a polypeptide. A half life-extending moiety can be downstream from the regions recited in (a) and/or from the regions recited in (b). The half life-extending moiety can be an Fc polypeptide chain, and the first and second polypeptide chains can each comprise an Fc polypeptide chain downstream from the regions represented by the formulas recited in (a) and (b). The target cell can be a cancer cell. The immune effector cell can be a T cell, an NK cell, a macrophage, a monocyte, or a neutrophil, and the heterodimeric bispecific antibody can mediate increased expression of CD25 and CD69 on the T cell in the presence of target cells, but not in the absence of target cells. The Fc polypeptide chains of the first and second polypeptide chains can be human IgG Fc polypeptide chains, such as IgG1, IgG2, IgG3, or IgG4 Fc polypeptide chains or variants thereof comprising not more than 10 deletions, insertions, or substitutions of a single amino acid per 100 amino acids of sequence. Such amino acid alterations can be engineered to prevent or augment binding to Fcγ receptors or immune cells, such as macrophages, monocytes, or NK cells. For example, if binding to Fcγ receptors is augmented, Fcγ receptor positive cells can be more readily engaged to augment killing of target cells. In some embodiments, L1 and L3 are no more than 12 amino acids long or 10 amino acids long. In some embodiments, one of V1 and V4 can be an immunoglobulin heavy chain variable (VH) region and the other can be an immunoglobulin light chain variable (VL) region, and V1 and V4 can bind to a target cell or an immune effector cell when they are part of an IgG or and/or an scFv antibody. In such embodiments, one of V2 and V3 can be a VH region and the other can be a VL region, and V2 and V3 can bind to a target cell or an immune effector cell when they are part of an IgG and/or an scFv antibody. V1 and V3 can be VL regions, and V2 and V4 can be VH regions. In other embodiments, V1 and V3 can be VH regions, and V2 and V4 can be VL regions. In further embodiments, V1 and V2 can be VL regions, and V3 and V4 can be VH regions. In still other embodiments, V1 and V2 can be VH regions, and V3 and V4 can be VL regions.

In another aspect, one of V1 and V3 can be a VH region and the other can be a VL region, and V1 and V3 can bind to a target cell or an immune effector cell when they are part of an IgG and/or an scFv antibody. In such embodiments, one of V2 and V4 can be a VH region and the other can be a VL region, and V2 and V4 can bind to a target cell or an immune effector cell when they are part of an IgG and/or an scFv antibody. In a further aspect, V1 and V2 can be VH regions, and V3 and V4 can be VL regions. Alternatively, V1 and V2 can be VL regions, and V3 and V4 can be VH regions. In another aspect, V1 and V4 can be VH regions, and V2 and V3 can be VL regions. In a further aspect, V1 and V4 can be VL regions, and V2 and V3 can be VH regions.

Any heterodimeric bispecific antibody described herein can bind to an immune effector cell. The effector cell protein can be part of a human TCR-CD3 complex. In such a case, the effector cell protein can, for example, be the CD3ε chain.

In a further embodiment, described herein is a heterodimeric bispecific antibody comprising two polypeptide chains selected from the group consisting of: (a) a first polypeptide chain comprising an amino acid sequence having the formula VH1-L1-VL2-L2-CH1 and a second polypeptide chain comprising an amino acid sequence having the formula VH2-L3-VL1-L4-CL; (b) a first polypeptide chain comprising an amino acid sequence having the formula VL2-L1-VH1-L2-CH1 and a second polypeptide chain comprising an amino acid sequence having the formula VL1-L3-VH2-L4-CL; (c) a first polypeptide chain comprising an amino acid sequence having the formula VH2-L1-VL1-L2-CH1 and a second polypeptide chain comprising an amino acid sequence having the formula VH1-L3-VL2-L4-CL; (d) a first polypeptide chain comprising an amino acid sequence having the formula VL2-L1-VL1-L2-CH1 and a second polypeptide chain comprising an amino acid sequence having the formula VH1-L3-VH2-L4-CL; (e) a first polypeptide chain comprising an amino acid sequence having the formula VL1-L1-VH2-L2-CH1 and a second polypeptide chain comprising an amino acid sequence having the formula VL2-L3-VH1-L4-CL; (f) a first polypeptide chain comprising an amino acid sequence having the formula VH1-L1-VH2-L2-CH1 and a second polypeptide chain comprising an amino acid sequence having the formula VL2-L3-VL1-L4-CL; (g) a first polypeptide chain comprising an amino acid sequence having the formula VH2-L1-VH1-L2-CH1 and a second polypeptide chain comprising an amino acid sequence having the formula VL1-L3-VL2-L4-CL; and (h) a first polypeptide chain comprising an amino acid sequence having the formula VL1-L1-VL2-L2-CH1 and a second polypeptide chain comprising an amino acid sequence having the formula VH2-L3-VH1-L4-CL; wherein L1, L2, L3, and L4 are linkers; wherein L2 and L4 can be present or absent; wherein VH1 and VL1 are heavy and light chain variable regions, respectively, and can bind to a target cell when they are part of an IgG and/or an scFv antibody; wherein VH2 and VL2 are heavy and light chain variable regions, respectively, and can bind to an immune effector cell when they are part of an IgG and/or an scFv antibody; wherein VH1 and VH2 have different amino acid sequences; and wherein either or both of the first and second polypeptide chain(s) further comprise(s) a half life-extending moiety downstream from the formulas recited in (a)-(h). VL1 and VL2 can have amino acid sequences that are the same or different. The first and second polypeptide chains can each comprise an Fc polypeptide chain downstream from the regions represented by the formulas recited in (a)-(h). The L1 and L3 linkers can be no more than 14, 13, 12, or 10 amino acids long or can be at least 15 amino acids long.

In another aspect, herein is described a heterodimeric bispecific antibody comprising two polypeptide chains selected from the group consisting of: (a) a first polypeptide chain comprising an amino acid sequence having the formula VH1-L1-VH2-L2-CH1 and a second polypeptide chain comprising an amino acid sequence having the formula VL1-L3-VL2-L4-CL; (b) a first polypeptide chain comprising an amino acid sequence having the formula VH2-L1-VH1-L2-CH1 and a second polypeptide chain comprising an amino acid sequence having the formula VL2-L3-VL1-L4-CL; (c) a first polypeptide chain comprising an amino acid sequence having the formula VL1-L1-VL2-L2-CH1 and a second polypeptide chain comprising an amino acid sequence having the formula VH1-L3-VH2-L4-CL; (d) a first polypeptide chain comprising an amino acid sequence having the formula VL2-L1-VL1-L2-CH1 and a second polypeptide chain comprising an amino acid sequence having the formula VH2-L3-VH1-L4-CL; (e) a first polypeptide chain comprising an amino acid sequence having the formula VL1-L1-VH2-L2-CH1 and a second polypeptide chain comprising an amino acid sequence having the formula VH1-L3-VL2-L4-CL; (f) a first polypeptide chain comprising an amino acid sequence having the formula VH2-L1-VL1-L2-CH1 and a second polypeptide chain comprising an amino acid sequence having the formula VL2-L3-VH1-L4-CL; (g) a first polypeptide chain comprising an amino acid sequence having the formula VL2-L1-VH1-L2-CH1 and a second polypeptide chain comprising an amino acid sequence having the formula VH2-L3-VL1-L4-CL; and (h) a first polypeptide chain comprising an amino acid sequence having the formula VH1-L1-VL2-L2-CH1 and a second polypeptide chain comprising an amino acid sequence having the formula VL1-L3-VH2-L4-CL; wherein L1, L2, L3, and L4 are linkers; wherein L2 and L4 are present or absent; wherein VH1 and VL1 are heavy and light chain variable regions, respectively, and can bind to a target cell when they are part of an IgG and/or an scFv antibody; wherein VH2 and VL2 are heavy and light chain variable regions, respectively, and can bind to an immune effector cell when they are part of an IgG and/or an scFv antibody; wherein VH1 and VH2 have different amino acid sequences; and wherein either or both of the first and second polypeptide chain(s) further comprise(s) a half life-extending moiety downstream from the formulas recited in (a)-(h). VL1 and VL2 can have amino acid sequences that are the same or different. The first and second polypeptide chains can each comprise an Fc polypeptide chain downstream from the regions represented by the formulas recited in (a)-(h). The L1 and L3 linkers can be no more than 14, 13, 12, or 10 amino acids long or can be at least 15 amino acids long.

In another aspect, a heterodimeric bispecific antibody can comprise a VH region comprising the amino acid sequence of SEQ ID NO:42 or a variant of SEQ ID NO:42 containing not more than 20 insertions, deletions, or substitutions relative to SEQ ID NO:42 and a VL region comprising the amino acid sequence of SEQ ID NO:43 or a variant of SEQ ID NO:43 containing not more than 20 insertions, deletions, or substitutions of a single amino acid relative to SEQ ID NO:43. Alternatively, a heterodimeric bispecific antibody can comprise a VH region comprising the amino acid sequence of SEQ ID NO:44 or a variant of SEQ ID NO:44 containing not more than 20 insertions, deletions, or substitutions relative to SEQ ID NO:44 and a VL region comprising the amino acid sequence of SEQ ID NO:45 or a variant of SEQ ID NO:45 containing not more than 20 insertions, deletions, or substitutions of a single amino acid relative to SEQ ID NO:45. In other embodiments, a heterodimeric bispecific antibody can comprise a V1, V2, V3, and V4 that comprise the amino acid sequences of SEQ ID NO:46 or 49, SEQ ID NO:43, SEQ ID NO:42, and SEQ ID NO:48, respectively. Alternatively, a heterodimeric bispecific antibody can comprise a V1, V2, V3, and V4, as described above, that comprise the amino acid sequences of SEQ ID NO:43, SEQ ID NO:46 or 49, SEQ ID NO:48, and SEQ ID NO:42, respectively. In a further alternative, a heterodimeric bispecific antibody can comprise a V1, V2, V3, and V4, as described above, that comprise the amino acid sequences of SEQ ID NO:50, SEQ ID NO:46 or 49, SEQ ID NO:48, and SEQ ID NO:51, respectively. In still another alternative, a heterodimeric bispecific antibody can comprise a V1, V2, V3, and V4, as described above, that comprise the amino acid sequences of SEQ ID NO:44, SEQ ID NO:52, SEQ ID NO:53, and SEQ ID NO:45, respectively. In the constructs mentioned above, the VH and VL regions having the amino acid sequences of SEQ ID NOs:82 and 83, respectively, can replace the VH and VL regions SEQ ID NOs:42 and 43 or SEQ ID NOs:44 and 45. Any heterodimeric bispecific antibody described herein can comprise the amino acid sequences of SEQ ID NO:82 and 83. It is further contemplated that variants of the amino acid sequences mentioned above containing not more than 10 deletions, insertions, or substitutions of a single amino acid per 100 amino acids of sequence are provided herein.

Any heterodimeric bispecific antibody described herein that comprises an Fc polypeptide chain, optionally a human IgG Fc polypeptide chain, on both the first and second polypeptide chains can comprise at least one charge pair substitution on each Fc polypeptide chain. In some such embodiments, the Fc polypeptide chain portion of the first polypeptide chain can comprise the charge pair substitutions E356K, E356R, D356K, or D356R and D399K or D399R, and the Fc polypeptide chain portion of the second polypeptide can comprise the charge pair substitutions R409D, R409E, K409D, or K409E and N392D, N392E, K392D, or K392E. In other such embodiments, the Fc polypeptide chain portion of the second polypeptide chain can comprise the charge pair substitutions E356K, E356R, D356K, or D356R and D399K or D399R, and the Fc polypeptide chain portion of the first polypeptide comprises the charge pair substitutions R409D, R409E, K409D, or K409E and N392D, N392E, K392D, or K392E.

Any heterodimeric bispecific antibody described herein that comprises an Fc polypeptide chain on both the first and second polypeptide chains can comprise one or more alterations that inhibit Fc gamma receptor (FcγR) binding. Such alterations can include L234A, L235A, and/or any substitution at position 297.

Any heterodimeric bispecific antibody described herein that comprises an Fc polypeptide chain on both the first and second polypeptide chains can comprise one or more Fc alterations that extend half life. Such alterations can include an insertion between residues 384 and 385, according to the EU numbering system, in each of the Fc polypeptide chain portions of the first and second polypeptide chains, wherein the insertion comprises the amino acid sequence of any one of SEQ ID NOs:54-65.

In another aspect, any heterodimeric bispecific antibody described herein that comprises an Fc polypeptide chain on both the first and second polypeptide chains can comprise one or more alterations that enhance ADCC in the Fc polypeptide chain portions of the first and second polypeptide chains. These alterations can include amino acid substitutions, insertions, or deletions. Enhanced ADCC can also be engineered by de-fucosylation of the Fc polypeptide chains by various methods known in the art.

In addition, provided herein are one or more nucleic acid(s) encoding any polypeptide chain of any of the heterodimeric bispecific antibodies described herein. Exemplary nucleic acid sequences include SEQ ID NOs:32, 33, 34, 35, 36, 37, 38, and 39. Further provided are one or more vector(s) comprising such nucleic acid(s), and host cells containing such nucleic acid(s) or vector(s). In another aspect, described herein are methods of making a heterodimeric bispecific antibody comprising culturing a host cell containing such nucleic acids under conditions so as to express the nucleic acid encoding the heterodimeric bispecific antibody and recovering the antibody from the cell mass or cell culture supernatant.

In a different aspect, described herein is a method of treating a cancer patient comprising administering to the patient a therapeutically effective amount of any heterodimeric bispecific antibody described herein, wherein the target cell protein is a cancer cell antigen. In some embodiments, chemotherapy or radiation can be administered to the patient concurrently with, before, or after administration of the antibody. In another approach, a non-chemotherapeutic anti-neoplastic agent can be administered to the patient concurrently with, before, or after administration of the antibody.

In a further aspect, described herein is method for treating a patient having an infectious disease comprising administering to the patient a therapeutically effective dose of any heterodimeric bispecific antibody described herein, wherein the target cell is an infected cell.

In a further aspect, provided herein is method for treating a patient having an autoimmune or inflammatory condition or a fibrotic condition comprising administering to the patient a therapeutically effective dose of any heterodimeric bispecific antibody described herein.

Provided herein is a use of any heterodimeric bispecific antibody described herein as a medicament.

In a further aspect, described herein is a pharmaceutical composition comprising any heterodimeric bispecific antibody described herein. The pharmaceutical composition can be for the treatment of cancer, an infectious disease, an autoimmune or inflammatory disease, or a fibrotic disease.

BRIEF DESCRIPTION OF THE FIGURES

FIG. 10: An anti-FOLR1/CD3ε heterodimeric bispecific antibody or single chain anti-FOLR1/CD3ε molecule stimulates release of cytokines from T cells in the presence of a FOLR1-expressing tumor cell line (T47D). The methods used are described in Example 6. In each panel, the x axis indicates the concentration of the anti-FOLR1/CD3ε heterodimeric bispecific antibody or single chain molecule (pM) used in the TDCC assay. The y axis indicates the concentration of the cytokine detected in the supernatant (pg/mL). Open circles connected by a dashed line indicate data from samples containing the anti-FOLR1/CD3ε heterodimeric bispecific antibody, whereas solidly filled circles connected by solid lines indicate data from samples containing the anti-FOLR1/CD3ε single chain molecule. The cytokines assayed are indicated in each panel. As indicated, panels on the left show data from samples containing T47D cells, and panels on the right show data from samples containing BT474 cells. As indicated.

FIG. 11: An anti-HER2/CD3ε heterodimeric bispecific antibody or anti-HER2/CD3ε single chain molecule stimulates the release of cytokines from T cells in the presence of a HER2-expressing tumor cell line (JIMT-1). The methods used are described in Example 7. In each panel, the x axis indicates the concentration of the anti-HER2/CD3ε heterodimeric bispecific antibody or single chain molecule (pM) used in the TDCC assay. The y axis indicates the concentration of the cytokine detected in the supernatant (pg/mL). Open circles connected by a dashed line indicate data from samples containing the anti-HER2/CD3ε heterodimeric bispecific antibody, whereas solidly filled circles connected by solid lines indicate data from samples containing the anti-HER2/CD3ε single chain molecule. The cytokines assayed are indicated in each panel. As indicated, panels on the left show data from samples containing JIMT-1 cells, and panels on the right show data from samples containing SHP77 cells. As indicated.

BRIEF DESCRIPTION OF THE SEQUENCES

Figure 1:
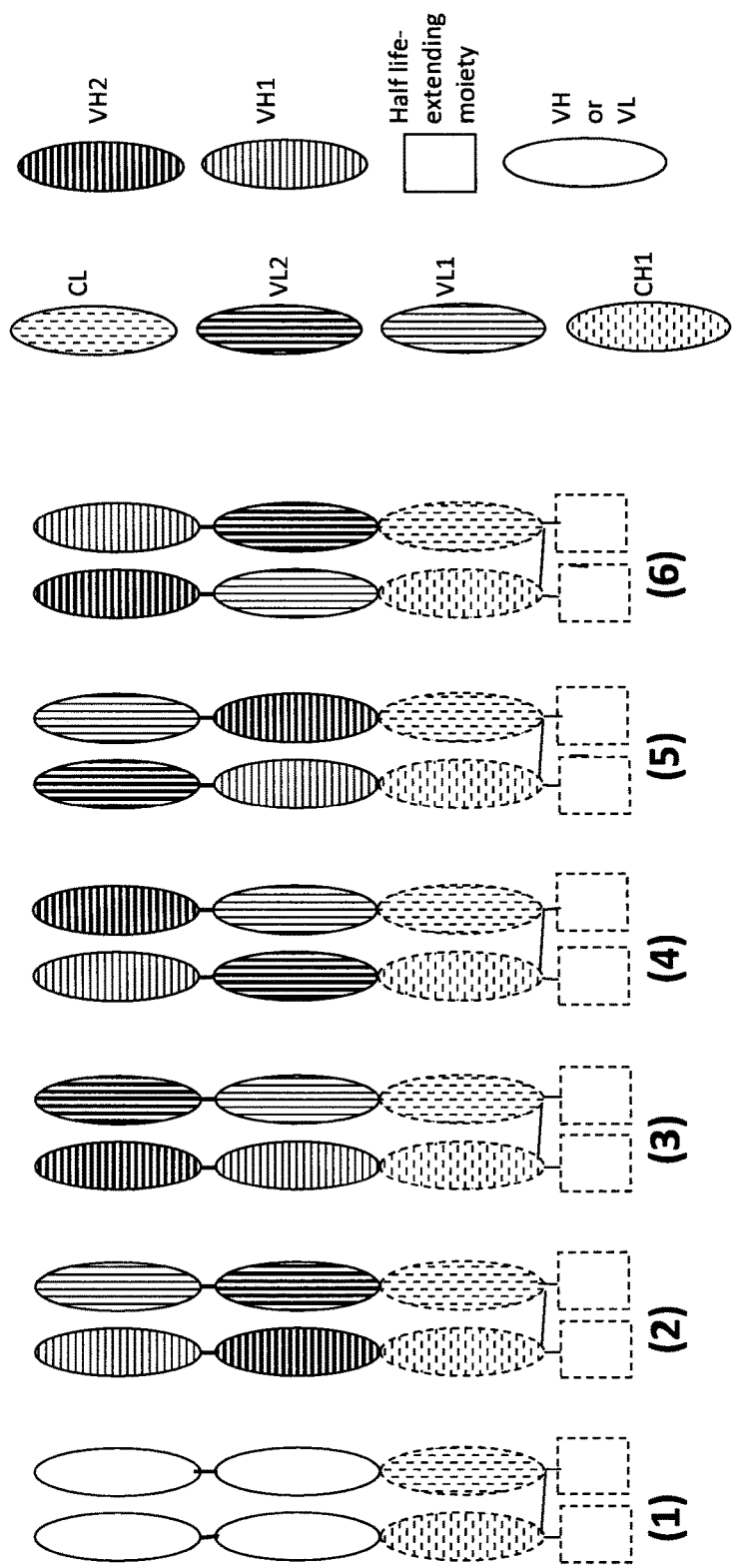
FIG. 1: Exemplary subtypes of heterodimeric bispecific antibodies. In these diagrams VH1 and VL1 are a pair of immunoglobulin heavy and light chain variable regions that can bind to a "target cell protein," and VH2 and VL2 are a pair of immunoglobulin heavy and light chain variable regions that can bind to an "effector cell protein." Other regions depicted in the diagrams are identified in the figure. The dashed lines surrounding the CL and CH1 regions mean that these regions can be eliminated in some embodiments. In some embodiments, both the CL and the CH1 regions are eliminated. The dashed lines delineating the squares representing the half life-extending moieties also indicate that these can be eliminated in some embodiments. However, in this case, only one or the other, not both, half life-extending moieties can be eliminated.

| SEQ ID NO | Description |
| --- | --- |
| SEQ ID NO: 1 | Amino acid sequence of human fibronectin 3 domain |
| SEQ ID NO: 2 | Amino acid sequence of human IqG1 Fc region |
| SEQ ID NO: 3 | Amino acid sequence of human IqG2 Fc region |
| SEQ ID NO: 4 | Amino acid sequence of human IqG3 Fc region |
| SEQ ID NO: 5 | Amino acid sequence of human IqG4 Fc region |
| SEQ ID NO: 6 | Amino acid sequence of the first polypeptide chain of P57216.9 |
| SEQ ID NO: 7 | Amino acid sequence of the second polypeptide chain of P57216.9 |
| SEQ ID NO: 8 | Amino acid sequence of the first polypeptide chain of P56019.5 |
| SEQ ID NO: 9 | Amino acid sequence of the second polypeptide chain of P56019.5 |
| SEQ ID NO: 10 | Amino acid sequence of the first polypeptide chain of H71362.2 |
| SEQ ID NO: 11 | Amino acid sequence of the second polypeptide chain of H71362.2 |
| SEQ ID NO: 12 | Amino acid sequence of the first polypeptide chain of P69058.3 |
| SEQ ID NO: 13 | Amino acid sequence of the second polypeptide chain of P69058.3 |

-continued

| SEQ ID NO | Description |
|---|---|
| SEQ ID NO: 14 | Amino acid sequence of the first polypeptide chain of P69059.3 |
| SEQ ID NO: 15 | Amino acid sequence of the second polypeptide chain of P69059.3 |
| SEQ ID NO: 16 | Amino acid sequence of the first polypeptide chain of E73356.3 |
| SEQ ID NO: 17 | Amino acid sequence of the second polypeptide chain of E73356.3 |
| SEQ ID NO: 18 | Amino acid sequence of the first polypeptide chain of E73352.3 |
| SEQ ID NO: 19 | Amino acid sequence of the second polypeptide chain of E73352.3 |
| SEQ ID NO: 20 | Amino acid sequence of the first polypeptide chain of P136797.3 |
| SEQ ID NO: 21 | Amino acid sequence of the second polypeptide chain of P136797.3 |
| SEQ ID NO: 22 | Amino acid sequence of the first polypeptide chain of P136795.3 |
| SEQ ID NO: 23 | Amino acid sequence of the second polypeptide chain of P136795.3 |
| SEQ ID NO: 24 | Amino acid sequence of the first polypeptide chain of H69070.4 |
| SEQ ID NO: 25 | Amino acid sequence of the second polypeptide chain of H69070.4 |
| SEQ ID NO: 26 | Amino acid sequence of the first polypeptide chain of H69071.4 |
| SEQ ID NO: 27 | Amino acid sequence of the second polypeptide chain of H69071.4 |
| SEQ ID NO: 28 | Amino acid sequence of the first polypeptide chain of H69072.4 |
| SEQ ID NO: 29 | Amino acid sequence of the second polypeptide chain of H69072.4 |
| SEQ ID NO: 30 | Amino acid sequence of the first polypeptide chain of H71365.2 |
| SEQ ID NO: 31 | Amino acid sequence of the second polypeptide chain of H71365.2 |
| SEQ ID NO: 32 | Polynucleotide sequence encoding first polypeptide chain of P57216.9 |
| SEQ ID NO: 33 | Polynucleotide sequence encoding second polypeptide chain of P57216.9 |
| SEQ ID NO: 34 | Polynucleotide sequence encoding first polypeptide chain of P69058.3 |
| SEQ ID NO: 35 | Polynucleotide sequence encoding second polypeptide chain of P69058.3 |
| SEQ ID NO: 36 | Polynucleotide sequence encoding first polypeptide chain of P69059.3 |
| SEQ ID NO: 37 | Polynucleotide sequence encoding second polypeptide chain of P69059.3 |
| SEQ ID NO: 38 | Polynucleotide sequence encoding first polypeptide chain of P136795.3 |
| SEQ ID NO: 39 | Polynucleotide sequence encoding second polypeptide chain of P136795.3 |
| SEQ ID NO: 40 | Mature amino acid sequence of CD3 epsilon chain of *Homo sapiens* |
| SEQ ID NO: 41 | Mature amino acid sequence of CD3 epsilon chain of *Macaca fascicularis* |
| SEQ ID NO: 42 | Amino acid sequence of anti-CD3ε VH region (9C11) |
| SEQ ID NO: 43 | Amino acid sequence of anti-CD3ε VL region (9C11) |
| SEQ ID NO: 44 | Amino acid sequence of anti-CD3ε VH region (F12Q) |
| SEQ ID NO: 45 | Amino acid sequence of anti-CD3ε VL region (F12Q) |
| SEQ ID NO: 46 | Amino acid sequence of the first immunoglobulin variable region of P69058.3 |
| SEQ ID NO: 47 | Amino acid sequence of the third immunoglobulin variable region of P69058.3 |
| SEQ ID NO: 48 | Amino acid sequence of the fourth immunoglobulin variable region of P69058.3 |
| SEQ ID NO: 49 | Amino acid sequence of the second immunoglobulin variable region of P69059.3 |
| SEQ ID NO: 50 | Amino acid sequence of the first immunoglobulin variable region of H69072.4 |
| SEQ ID NO: 51 | Amino acid sequence of the fourth immunoglobulin variable region of H69072.4 |
| SEQ ID NO: 52 | Amino acid sequence of the second immunoglobulin variable region of P136795.3 |
| SEQ ID NO: 53 | Amino acid sequence of the third immunoglobulin variable region of P136795.3 |
| SEQ ID NO: 54 | Amino acid sequence of a peptide insertion that increases half life |
| SEQ ID NO: 55 | Amino acid sequence of a peptide insertion that increases half life |
| SEQ ID NO: 56 | Amino acid sequence of a peptide insertion that increases half life |
| SEQ ID NO: 57 | Amino acid sequence of a peptide insertion that increases half life |
| SEQ ID NO: 58 | Amino acid sequence of a peptide insertion that increases half life |
| SEQ ID NO: 59 | Amino acid sequence of a peptide insertion that increases half life |
| SEQ ID NO: 60 | Amino acid sequence of a peptide insertion that increases half life |
| SEQ ID NO: 61 | Amino acid sequence of a peptide insertion that increases half life |
| SEQ ID NO: 62 | Amino acid sequence of a peptide insertion that increases half life |
| SEQ ID NO: 63 | Amino acid sequence of a peptide insertion that increases half life |

-continued

| SEQ ID NO | Description |
|---|---|
| SEQ ID NO: 64 | Amino acid sequence of a peptide insertion that increases half life |
| SEQ ID NO: 65 | Amino acid sequence of a peptide insertion that increases half life |
| SEQ ID NO: 66 | Amino acid sequence of a linker |
| SEQ ID NO: 67 | Amino acid sequence of a linker |
| SEQ ID NO: 68 | Amino acid sequence of a linker |
| SEQ ID NO: 69 | Amino acid sequence of a linker |
| SEQ ID NO: 70 | Amino acid sequence of a CH1 region |
| SEQ ID NO: 71 | Amino acid sequence of a lambda CL region |
| SEQ ID NO: 72 | Amino acid sequence of VL specific to MSLN |
| SEQ ID NO: 73 | Amino acid sequence of a kappa CL region |
| SEQ ID NO: 74 | Amino acid sequence of a linker |
| SEQ ID NO: 75 | Amino acid sequence of an anti-HER2/CD3ε single chain bispecific molecule |
| SEQ ID NO: 76 | Amino acid sequence of an anti-FOLR1/CD3ε single chain bispecific molecule |
| SEQ ID NO: 77 | Amino acid sequence preceding a heavy chain CDR1 |
| SEQ ID NO: 78 | Amino acid preceding a heavy chain CDR2 |
| SEQ ID NO: 79 | Amino acid sequence following a heavy chain CDR3 |
| SEQ ID NO: 80 | Amino acid sequence preceding a light chain CDR3 |
| SEQ ID NO: 81 | Amino acid sequence of a portion of an epitope on CD3ε |
| SEQ ID NO: 82 | Amino acid sequence of an anti-CD3ε VH region (12C) |
| SEQ ID NO: 83 | Amino acid sequence of an anti-CD3ε VL region (12C) |
| SEQ ID NO: 84 | Amino acid sequence of a second polypeptide chain anti-FOLR1/CD3ε heterodimeric bispecific antibody (PL-30056) |
| SEQ ID NO: 85 | Polynucleotide sequence encoding the second polypeptide chain of the anti-FOLR1/CD3ε heterodimeric bispecific antibody (PL-30056) |
| SEQ ID NO: 86 | Amino acid sequence of a first polypeptide chain anti-FOLR1/CD3ε heterodimeric bispecific antibody (PL-30056) |
| SEQ ID NO: 87 | Polynucleotide sequence encoding the first polypeptide chain of the anti-FOLR1/CD3ε heterodimeric bispecific antibody (PL-30056) |
| SEQ ID NO: 88 | Amino acid sequence of an anti-FOLR1/CD3 single chain bispecific (PL-30055) |
| SEQ ID NO: 89 | Polynucleotide sequence encoding the anti-FOLR1/CD3ε single chain bispecific of SEQ ID NO: 88 |
| SEQ ID NO: 90 | Amino acid sequence of an anti-Mec/CD3ε single chain bispecific (P137424.7) |
| SEQ ID NO: 91 | Polynucleotide sequence encoding the amino acid sequence of the anti-Mec/CD3ε single chain bispecific (P137424.7) |
| SEQ ID NO: 92 | Amino acid sequence of an anti-CD33/CD3ε single chain bispecific (P138241.3) |
| SEQ ID NO: 93 | Polynucleotide sequence encoding the amino acid sequence of an anti-CD33/CD3ε single chain bispecific (P138241.3) |
| SEQ ID NO: 94 | Amino acid sequence of a first polypeptide chain of an anti-CD33/CD3ε heterodimeric bispecific antibody (PL-144537.6) |
| SEQ ID NO: 95 | Polynucleotide sequence encoding the amino acid sequence of the first polypeptide chain of an anti-CD33/CD3ε heterodimeric bispecific antibody (PL-144537.6) |
| SEQ ID NO: 96 | Amino acid sequence of a second polypeptide chain of an anti-CD33/CD3ε heterodimeric bispecific antibody (PL-144537.6) |
| SEQ ID NO: 97 | Polynucleotide sequence encoding the amino acid sequence of the second polypeptide chain of an anti-CD33/CD3ε heterodimeric bispecific antibody (PL-144537.6) |

DETAILED DESCRIPTION

Described herein is a new form of bispecific antibody. It is a heterodimeric molecule containing two different polypeptide chains, each comprising two immunoglobulin variable regions and, optionally, either a CH1 domain or a Cκ or Cλ domain. Together, the two chains contain two different binding sites, each of which comprises a heavy and light chain immunoglobulin variable (VH and VL) region and each of which binds to a different protein. In some embodiments, one of the proteins is expressed on the surface of an immune effector cell, such as a T cell, an NK cell, a macrophage, a monocyte, or a neutrophil and the other protein is expressed on the surface of a target cell, for example a cancer cell, a cell infected by a pathogen such as a virus, or a cell that mediates a fibrotic, autoimmune, or inflammatory disease. Since a heterodimeric bispecific antibody, as described herein, has only one binding site for each of the proteins it binds to (i.e., it binds "monovalently" to each protein), its binding will not oligomerize the proteins it binds to on a cell surface. For example, if it binds to CD3 on the surface of a T cell, CD3 will not be oligomerized on the T cell surface. Oligomerization of CD3 can cause a generalized activation of a T cell, which can be undesirable. The heterodimeric bispecific antibody described herein tethers an immune effector cell to a target cell, forming a close physical association between the cells and thereby eliciting a specific cytolytic activity against the target cell. The mechanism of action may be similar to that explored in detail for other bispecific antibodies. See, e.g., Haas et al. (2009), Immunobiology 214(6): 441-453. Further, the heterodimeric bispecific antibodies comprise at least one, optionally two, half life-extending moieties. Thus, they have favorable pharmacokinetic properties and are not unduly complex to manufacture since they contain only two different polypeptide chains.

Definitions

An "antibody," as meant herein, is a protein containing at least one VH or VL region, in many cases a heavy and a light chain variable region. Thus, the term "antibody" encompasses molecules having a variety of formats, including single chain Fv antibodies (scFv, which contain VH and VL regions joined by a linker), Fab, F(ab)$_2$', Fab', scFv:Fc antibodies (as described in Carayannopoulos and Capra, Ch. 9 in FUNDAMENTAL IMMUNOLOGY, 3$^{rd}$ ed., Paul, ed., Raven Press, New York, 1993, pp. 284-286) or full length antibodies containing two full length heavy and two full length light chains, such as naturally-occurring IgG antibodies found in mammals. Id. Such IgG antibodies can be of the IgG1, IgG2, IgG3, or IgG4 isotype and can be human antibodies. The portions of Carayannopoulos and Capra that describe the structure of antibodies are incorporated herein by reference. Further, the term "antibody" includes dimeric antibodies containing two heavy chains and no light chains such as the naturally-occurring antibodies found in camels and other dromedary species and sharks. See, e.g., Muldermans et al., 2001, J. Biotechnol. 74:277-302; Desmyter et al., 2001, J. Biol. Chem. 276:26285-90; Streltsov et al. (2005), Protein Science 14: 2901-2909. An antibody can be "monospecific" (that is, binding to only one kind of antigen), "bispecific" (that is, binding to two different antigens), or "multispecific" (that is, binding to more than one different antigen). Further, an antibody can be monovalent, bivalent, or multivalent, meaning that it can bind to one, two, or multiple antigen molecules at once, respectively. An antibody binds "monovalent," to a particular protein when one molecule of the antibody binds to only one molecule of the protein, even though the antibody may also bind to a different protein as well. That is, an antibody binds "monovalently," as meant herein, to two different proteins when it binds to only one molecule of each protein. Such an antibody is "bispecific" and binds to each of two different proteins "monovalently." An antibody can be "monomeric," i.e., comprising a single polypeptide chain. An antibody can comprise multiple polypeptide chains ("multimeric") or can comprise two ("dimeric"), three ("trimeric"), or four ("tetrameric") polypeptide chains. If multimeric, an antibody can be a homomultimer, i.e., containing more than one molecule of only one kind of polypeptide chain, including homodimers, homotrimer, or homotetramers. Alternatively, a multimeric antibody can be a heteromultimer, i.e., containing more than one different kind of polypeptide chain, including heterodimers, heterotrimers, or heterotetramers. An antibody can have a variety of possible formats including, for example, monospecific monovalent antibodies (as described in International Application WO 2009/089004 and US Publication 2007/0105199, the relevant portions of which are incorporated herein by reference) that may inhibit or activate the molecule to which they bind, bivalent monospecific or bispecific dimeric Fv-Fc, scFv-Fc, or diabody Fc, monospecific monovalent scFv-Fc/Fc's, the multispecific binding proteins and dual variable domain immunoglobulins described in US Publication 2009/0311253 (the relevant portions of which are incorporated herein by reference), the heterodimeric bispecific antibodies described herein, and the many formats for bispecific antibodies described in Chapters 1, 4, 5, 6, 7, 8, 9, 10, 11, 12, 13, 14 of BISPECIFIC ANTIBODIES, Kontermann, ed., Springer, 2011 (which chapters are incorporated herein by reference), among many other possible antibody formats.

A "cancer cell antigen," as meant herein, is a protein expressed on the surface of a cancer cell. Some cancer cell antigens are also expressed on some normal cells, and some are specific to cancer cells. Cancer cell antigens can be highly expressed on the surface of a cancer cell. There are a wide variety of cancer cell antigens. Examples of cancer cell antigens include, without limitation, the following human proteins: epidermal growth factor receptor (EGFR), EGFRvIII (a mutant form of EGFR), melanoma-associated chondroitin sulfate proteoglycan (MCSP), mesothelin (MSLN), folate receptor 1 (FOLR1), CD33, CDH19, and epidermal growth factor 2 (HER2), among many others.

"Chemotherapy," as used herein, means the treatment of a cancer patient with a "chemotherapeutic agent" that has cytotoxic or cytostatic effects on cancer cells. A "chemotherapeutic agent" specifically targets cells engaged in cell division and not cells that are not engaged in cell division. Chemotherapeutic agents directly interfere with processes that are intimately tied to cell division such as, for example, DNA replication, RNA synthesis, protein synthesis, the assembly, disassembly, or function of the mitotic spindle, and/or the synthesis or stability of molecules that play a role in these processes, such as nucleotides or amino acids. A chemotherapeutic agent therefore has cytotoxic or cytostatic effects on both cancer cells and other cells that are engaged in cell division. Chemotherapeutic agents are well-known in the art and include, for example: alkylating agents (e.g. busulfan, temozolomide, cyclophosphamide, lomustine (CCNU), methyllomustine, streptozotocin, cis-diamminedichloroplatinum, aziridinylbenzo-quinone, and thiotepa); inorganic ions (e.g. cisplatin and carboplatin); nitrogen mustards (e.g. melphalan hydrochloride, ifosfamide, chlorambucil, and mechlorethamine HCl); nitrosoureas (e.g. carmustine (BCNU)); anti-neoplastic antibiotics (e.g. adriamycin (doxorubicin), daunomycin, mitomycin C, daunorubicin, idarubicin, mithramycin, and bleomycin); plant derivatives (e.g. vincristine, vinblastine, vinorelbine, paclitaxel, docetaxel, vindesine, VP-16, and VM-26); antimetabolites (e.g. methotrexate with or without leucovorin, 5-fluorouracil with or without leucovorin, 5-fluorodeoxyuridine, 6-mercaptopurine, 6-thioguanine, cytarabine, 5-azacytidine, hydroxyurea, deoxycoformycin, gemcitabine, and fludarabine); podophyllotoxins (e.g. etoposide, irinotecan, and topotecan); as well as actinomycin D, dacarbazine (DTIC), mAMSA, procarbazine, hexamethylmelamine, pentamethylmelamine, L-asparaginase, and mitoxantrone, among many known in the art. See e.g. Cancer: Principles and Practice of Oncology, 4$^{th}$ Edition, DeVita et al., eds., J. B. Lippincott Co., Philadelphia, Pa. (1993), the relevant portions of which are incorporated herein by reference. Alkylating agents and nitrogen mustard act by alkylating DNA, which restricts uncoiling and replication of strands. Methotrexate, cytarabine, 6-mercaptopurine, 5-fluorouracil, and gemcitabine interfere with nucleotide synthesis. Plant derivatives such a paclitaxel and vinblastine are mitotic spindle poisons. The podophyllotoxins inhibit topoisomerases, thus interfering with DNA replication. Antibiotics doxorubicin, bleomycin, and mitomycin interfere with DNA synthesis by intercalating between the bases of DNA (inhibiting uncoiling), causing strand breakage, and alkylating DNA, respectively. Other mechanisms of action include carbamoylation of amino acids (lomustine, carmustine), and depletion of asparagine pools (asparaginase). Merck Manual of Diagnosis and Therapy, 17$^{th}$ Edition, Section 11, Hematology and Oncology, 144. Principles of Cancer Therapy, Table 144-2 (1999). Specifically included among chemotherapeutic agents are those that directly affect the same cellular processes that are directly affected by the chemotherapeutic agents listed above.

A drug or treatment is "concurrently" administered with a heterodimeric bispecific antibody, as meant herein, if it is administered in the same general time frame as the antibody, optionally, on an ongoing basis. For example, if a patient is taking Drug A once a week on an ongoing basis and the antibody once every six months on an ongoing basis, Drug A and the antibody are concurrently administered, whether or not they are ever administered on the same day. Similarly, if the antibody is taken once per week on an ongoing basis and Drug A is administered only once or a few times on a daily basis, Drug A and the antibody are concurrently administered as meant herein. Similarly, if both Drug A and the antibody are administered for short periods of time either once or multiple times within a one month period, they are administered concurrently as meant herein as long as both drugs are administered within the same month.

A "conservative amino acid substitution," as meant herein, is a substitution of an amino acid with another amino acid with similar properties. Properties considered include chemical properties such as charge and hydrophobicity. Table 1 below lists substitutions for each amino acid that are considered to be conservative substitutions as meant herein.

TABLE 1

Conservative Amino Acid Substitutions

| Original Residue | Conservative Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

As meant herein, an "Fc region" is a dimer consisting of two polypeptide chains joined by one or more disulfide bonds, each chain comprising part or all of a hinge domain plus a CH2 and a CH3 domain. Each of the polypeptide chains is referred to as an "Fc polypeptide chain." To distinguish the two Fc polypeptide chains, in some instances one is referred to herein as an "A chain" and the other is referred to as a "B chain." More specifically, the Fc regions contemplated for use with the present invention are IgG Fc regions, which can be mammalian, for example human, IgG1, IgG2, IgG3, or IgG4 Fc regions. Among human IgG1 Fc regions, at least two allelic types are known. In other embodiments, the amino acid sequences of the two Fc polypeptide chains can vary from those of a mammalian Fc polypeptide by no more than 10 substitutions, insertions, and/or deletions of a single amino acid per 100 amino acids of sequence relative to a mammalian Fc polypeptide amino acid sequence. In some embodiments, such variations can be "heterodimerizing alterations" that facilitate the formation of heterodimers over homodimers, an Fc alteration that extends half life, an alteration that inhibits Fc gamma receptor (FcγR) binding, and/or an alteration that enhances Fcγ receptor binding and enhances ADCC.

An "Fc alteration that extends half life," as meant herein, is an alteration within an Fc polypeptide chain that lengthens the in vivo half life of a protein that contains the altered Fc polypeptide chain as compared to the half life of a similar protein containing the same Fc polypeptide, except that it does not contain the alteration. Such alterations can be included in an Fc polypeptide chain that is part of a heterodimeric bispecific antibody as described herein. The alterations M252Y, S254T, and T256E (methionine at position 252 changed to tyrosine; serine at position 254 changed to threonine; and threonine at position 256 changed to glutamic acid; numbering according to EU numbering as shown in Table 2) are Fc alterations that extend half life and can be used together, separately or in any combination. These alterations and a number of others are described in detail in U.S. Pat. No. 7,083,784. The portions of U.S. Pat. No. 7,083,784 that describe such alterations are incorporated herein by reference. Similarly, M428L and N434S are Fc alterations that extend half life and can be used together, separately or in any combination. These alterations and a number of others are described in detail in U.S. Patent Application Publication 2010/0234575 and U.S. Pat. No. 7,670,600. The portions of U.S. Patent Application Publication 2010/0234575 and U.S. Pat. No. 7,670,600 that describe such alterations are incorporated herein by reference. In addition, any substitution at one of the following sites can be considered an Fc alteration that extends half life as meant here: 250, 251, 252, 259, 307, 308, 332, 378, 380, 428, 430, 434, 436. Each of these alterations or combinations of these alterations can be used to extend the half life of a heterodimeric bispecific antibody as described herein. Other alterations that can be used to extend half life are described in detail in International Application PCT/US2012/070146 filed Dec. 17, 2012. The portions of this application that describe such alterations are incorporated herein by reference. Some specific embodiments described in this application include insertions between positions 384 and 385 (EU numbering as shown in Table 2) that extend half life, including the following amino acid sequences: GGCVFNMFNCGG (SEQ ID NO:54), GGCHLPFAVCGG (SEQ ID NO:55), GGCGHEYMWCGG (SEQ ID NO:56), GGCWPLQDYCGG (SEQ ID NO:57), GGCMQMNKWCGG (SEQ ID NO:58), GGCDGRTKYCGG (SEQ ID NO:59), GGCALYPTNCGG (SEQ ID NO:60), GGCGKHWHQCGG (SEQ ID NO:61), GGCHSFKHFCGG (SEQ ID NO:62), GGCQGMWTWCGG (SEQ ID NO:63), GGCAQQWHHEYCGG (SEQ ID NO:64), and GGCERFHHACGG (SEQ ID NO:65), among others. Heterodimeric bispecific antibodies containing such insertions are contemplated.

A "half life-extending moiety," as meant herein, is a molecule that extends the in vivo half life of a protein to which it is attached as compared to the in vivo half life of the protein without the half life-extending moiety. Methods for measuring half life are well known in the art. A method for ascertaining half life is disclosed in Example 9. A half life-extending moiety can be a polypeptide, for example an Fc polypeptide chain or a polypeptide that can bind to albumin. The amino acid sequence of a domain of human fibronectin type III (Fn3) that has been engineered to bind to albumin is provided in SEQ ID NO:1, and various human IgG Fc polypeptide sequences are given in SEQ ID NOs:2-5. In alternate embodiments, a half life-extending moiety can be a non-polypeptide molecule. For example, a polyethylene glycol (PEG) molecule can be a half life-extending moiety.

"Heterodimerizing alterations" generally refer to alterations in the A and B chains of an Fc region that facilitate the formation of heterodimeric Fc regions, that is, Fc regions in which the A chain and the B chain of the Fc region do not have identical amino acid sequences. Such alterations can be included in an Fc polypeptide chain that is part of a heterodimeric bispecific antibody as described herein. Heterodimerizing alterations can be asymmetric, that is, an A chain having a certain alteration can pair with a B chain having a different alteration. These alterations facilitate heterodimerization and disfavor homodimerization. Whether hetero- or homo-dimers have formed can be assessed by size differences as determined by polyacrylamide gel electrophoresis in some situations or by other appropriate means such as differing charges or biophysical characteristics, including binding by antibodies or other molecules that recognize certain portions of the heterodimer including molecular tags. One example of such paired heterodimerizing alterations are the so-called "knobs and holes" substitutions. See, e.g., U.S. Pat. No. 7,695,936 and US Patent Application Publication 2003/0078385, the portions of which describe such mutations are incorporated herein by reference. As meant herein, an Fc region that contains one pair of knobs and holes substitutions, contains one substitution in the A chain and another in the B chain. For example, the following knobs and holes substitutions in the A and B chains of an IgG1 Fc region have been found to increase heterodimer formation as compared with that found with unmodified A and B chains: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. This way of notating mutations can be explained as follows. The amino acid (using the one letter code) normally present at a given position in the CH3 region using the EU numbering system (which is presented in Edelman et al (1969), Proc. Natl. Acad. Sci. 63: 78-85; see also Table 2 below) is followed by the EU position, which is followed by the alternate amino acid that is present at that position. For example, Y407T means that the tyrosine normally present at EU position 407 is replaced by a threonine. Alternatively or in addition to such alterations, substitutions creating new disulfide bridges can facilitate heterodimer formation. See, e.g., US Patent Application Publication 2003/0078385, the portions of which describe such mutations are incorporated herein by reference. Such alterations in an IgG1 Fc region include, for example, the following substitutions: Y349C in one Fc polypeptide chain and S354C in the other; Y349C in one Fc polypeptide chain and E356C in the other; Y349C in one Fc polypeptide chain and E357C in the other; L351C in one Fc polypeptide chain and S354C in the other; T394C in one Fc polypeptide chain and E397C in the other; or D399C in one Fc polypeptide chain and K392C in the other. Similarly, substitutions changing the charge of a one or more residue, for example, in the $C_H3$-$C_H3$ interface, can enhance heterodimer formation as explained in WO 2009/089004, the portions of which describe such substitutions are incorporated herein by reference. Such substitutions are referred to herein as "charge pair substitutions," and an Fc region containing one pair of charge pair substitutions contains one substitution in the A chain and a different substitution in the B chain. General examples of charge pair substitutions include the following: 1) K409D or K409E in one chain plus D399K or D399R in the other; 2) K392D or K392E in one chain plus D399K or D399R in the other; 3) K439D or K439E in one chain plus E356K or E356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of the these heterodimerizing alterations can be used in the Fc regions of the heterodimeric bispecific antibodies described herein.

An "alteration that inhibits FcγR binding," as meant herein, is one or more insertions, deletions, or substitutions within an Fc polypeptide chain that inhibits the binding of FcγRIIA, FcγRIIB, and/or FcγRIIIA as measured, for example, by an ALPHALISA®-based competition binding assay (Perkin Elmer, Waltham, Mass.). Such alterations can be included in an Fc polypeptide chain that is part of a heterodimeric bispecific antibody as described herein. More specifically, alterations that inhibit Fc gamma receptor (FcγR) binding include L234A, L235A, or any alteration that inhibits glycosylation at N297, including any substitution at N297. In addition, along with alterations that inhibit glycosylation at N297, additional alterations that stabilize a dimeric Fc region by creating additional disulfide bridges are also contemplated. Further examples of alterations that inhibit FcγR binding include a D265A alteration in one Fc polypeptide chain and an A327Q alteration in the other Fc polypeptide chain.

An "alteration that enhances ADCC," as meant herein is one or more insertions, deletions, or substitutions within an Fc polypeptide chain that enhances antibody dependent cell-mediated cytotoxicity (ADCC). Such alterations can be included in an Fc polypeptide chain that is part of a heterodimeric bispecific antibody as described herein. Many such alterations are described in International Patent Application Publication WO 2012/125850. Portions of this application that describe such alterations are incorporated herein by reference. Such alterations can be included in an Fc polypeptide chain that is part of a heterodimeric bispecific antibody as described herein. ADCC assays can be performed as follows. Cell lines that express high and lower amounts of a cancer cell antigen on the cell surface can be used as target cells. These target cells can belabeled with carboxyfluorescein succinimidyl ester (CFSE) and then washed once with phosphate buffered saline (PBS) before being deposited into 96-well microtiter plates with V-shaped wells. Purified immune effector cells, for example T cells, NK cells, macrophages, monocytes, or peripheral blood mononuclear cells (PBMCs), can be added to each well. A monospecific antibody that binds to the cancer antigen and contains the alteration(s) being tested and an isotype-matched control antibody can be diluted in a 1:3 series and added to the wells. The cells can be incubated at 37° C. with 5% $CO_2$ for 3.5 hrs. The cells can be spun down and re-suspended in 1×FACS buffer (1× phosphate buffered saline (PBS) containing 0.5% fetal bovine serum (FBS)) with the dye TO-PRO®-3 iodide (Molecular Probes, Inc. Corporation, Oregon, USA), which stains dead cells, before analysis by fluorescence activated cell sorting (FACS). The percentage of cell killing can be calculated using the following formula:

(percent tumor cell lysis with bispecific–percent tumor cell lysis without bispecific)/(percent total cell lysis–percent tumor cell lysis without bispecific)

Total cell lysis is determined by lysing samples containing effector cells and labeled target cells without a bispecific molecule with cold 80% methanol. Exemplary alterations that enhance ADCC include the following alterations in the A and B chains of anFc region: (a) the A chain comprises Q311M and K334V substitutions and the B chain comprises L234Y, E294L, and Y296W substitutions or vice versa; (b) the A chain comprises E233L, Q311M, and K334V substitutions and the B chain comprises L234Y, E294L, and Y296W substitutions or vice versa; (c) the A chain comprises L234I, Q311M, and K334V substitutions and the B chain comprises L234Y, E294L, and Y296W substitutions or vice versa; (d) the A chain comprises S298T and K334V substitutions and the B chain comprises L234Y, K290Y, and Y296W substitutions or vice versa; (e) the A chain comprises A330M and K334V substitutions and the B chain comprises L234Y, K290Y, and Y296W substitutions or vice versa; (f) the A chain comprises A330F and K334V substitutions and the B chain comprises L234Y, K290Y, and Y296W substitutions or vice versa; (g) the A chain comprises Q311M, A330M, and K334V substitutions and the B chain comprises L234Y, E294L, and Y296W substitutions or vice versa; (h) the A chain comprises Q311M, A330F, and K334V substitutions and the B chain comprises L234Y, E294L, and Y296W substitutions or vice versa; (i) the A chain comprises S298T, A330M, and K334V substitutions and the B chain comprises L234Y, K290Y, and Y296W substitutions or vice versa; (j) the A chain comprises S298T, A330F, and K334V substitutions and the B chain comprises L234Y, K290Y, and Y296W substitutions or vice versa; (k) the A chain comprises S239D, A330M, and K334V substitutions and the B chain comprises L234Y, K290Y, and Y296W substitutions or vice versa; (l) the A chain comprises S239D, S298T, and K334V substitutions and the B chain comprises L234Y, K290Y, and Y296W substitutions or vice versa; (m) the A chain comprises a K334V substitution and the B chain comprises Y296W and S298C substitutions or vice versa; (n) the A chain comprises a K334V substitution and the B chain comprises L234Y, Y296W, and S298C substitutions or vice versa; (o) the A chain comprises L235S, S239D, and K334V substitutions and the B chain comprises L234Y, K290Y, and Y296W, substitutions or vice versa; (p) the A chain comprises L235S, S239D, and K334V substitutions and the B chain comprises L234Y, Y296W, and S298C substitutions or vice versa; (q) the A chain comprises Q311M and K334V substitutions and the B chain comprises L234Y, F243V, and Y296W substitutions or vice versa; (r) the A chain comprises Q311M and K334V substitutions and the B chain comprises L234Y, K296W, and S298C substitutions or vice versa; (s) the A chain comprises S239D and K334V substitutions and the B chain comprises L234Y, K290Y, and Y296W substitutions or vice versa; (t) the A chain comprises S239D and K334V substitutions and the B chain comprises L234Y, Y296W, and S298C substitutions or vice versa; (u) the A chain comprises F243V and K334V substitutions and the B chain comprises L234Y, K290Y, and Y296W, substitutions or vice versa; (v) the A chain comprises F243V and K334V substitutions and the B chain comprises L234Y, Y296W, and S298C substitutions or vice versa; (w) the A chain comprises E294L and K334V substitutions and the B chain comprises L234Y, K290Y, and Y296W substitutions or vice versa; (x) the A chain comprises E294L and K334V substitutions and the B chain comprises L234Y, Y296W, and S298C substitutions or vice versa; (y) the A chain comprises A330M and K334V substitutions and the B chain comprises L234Y and Y296W substitutions or vice versa; or (z) the A chain comprises A330M and K334V substitutions and the B chain comprises K290Y and Y296W substitutions or vice versa.

An "IgG antibody," as meant herein, is an antibody consisting essentially of two immunoglobulin IgG heavy chains and two immunoglobulin light chains, which can be kappa or lambda light chains. More specifically, the heavy chains contain a VH region, a CH1 region, a hinge region, a CH2 region, and a CH3 region, while the light chains contain a VL region and a CL region. Numerous sequences of such immunoglobulin regions are known in the art. See, e.g., Kabat et al. in SEQUENCES OF IMMUNOLOGICAL INTEREST, Public Health Service N.I.H., Bethesda, Md., 1991. Sequences of regions from IgG antibodies disclosed in Kabat et al. are incorporated herein by reference.

An "immune effector cell," as meant herein, is a cell that is involved in the mediation of a cytolytic immune response, including, for example, T cells, NK cells, monocytes, macrophages, or neutrophils. The heterodimeric bispecific antibodies described herein bind to an antigen that is part of a protein expressed on the surface of an immune effector cell. Such proteins are referred to herein as "effector cell proteins."

An "immunoglobulin heavy chain," as meant herein, consists essentially of a VH region, a CH1 region, a hinge region, a CH2 region, a CH3 region in that order, and, optionally, a region downstream of the CH3 region in some isotypes. Close variants of an immunoglobulin heavy chain containing no more than 10 amino acid substitutions, insertions, and/or deletions of a single amino acid per 100 amino acids relative to a known or naturally occurring immunoglobulin heavy chain amino acid sequence are encompassed within what is meant by an immunoglobulin heavy chain.

A "immunoglobulin light chain," as meant herein, consists essentially of a light chain variable region (VL) and a light chain constant domain (CL). Close variants of an immunoglobulin light chain containing no more than 10 amino acid substitutions, insertions, and/or deletions of a single amino acid per 100 amino acids relative to a known or naturally occurring immunoglobulin light chain amino acid sequence are encompassed within what is meant by an immunoglobulin light chain.

An "immunoglobulin variable region," as meant herein, is a VH region, a VL region, or a variant thereof. Close variants of an immunoglobulin variable region containing no more than 10 amino acid substitutions, insertions, and/or deletions of a single amino acid per 100 amino acids relative to a known or naturally occurring immunoglobulin variable region amino acid sequence are encompassed within what is meant by an immunoglobulin variable region. Many examples of VH and VL regions are known in the art, such as, for example, those disclosed by Kabat et al. in SEQUENCES OF IMMUNOLOGICAL INTEREST, Public Health Service N.I.H., Bethesda, Md., 1991. Based on the extensive sequence commonalities in the less variable portions of the VH and VL regions, the position within a sequence of more variable regions, and the predicted tertiary structure, one of skill in the art can recognize an immunoglobulin variable region by its sequence. See, e.g., Honegger and Plückthun (2001), J. Mol. Biol. 309: 657-670.

An immunoglobulin variable region contains three hypervariable regions, known as complementarity determining region 1 (CDR1), complementarity determining region 2 (CDR2), and complementarity determining region 3 (CDR3). These regions form the antigen binding site of an antibody. The CDR5 are embedded within the less variable framework regions (FR1-FR4). The order of these subregions within an immunoglobulin variable region is as follows: FR1-CDR1-FR2-CDR2-FR3-CDR3-FR4. Numerous sequences of immunoglobulin variable regions are known in the art. See, e.g., Kabat of al., SEQUENCES OF PROTEINS OF IMMUNOLOGICAL INTEREST, Public Health Service N.I.H., Bethesda, Md., 1991.

CDR5 can be located in a VH region sequence in the following way. CDR1 starts at approximately residue 31 of the mature VH region and is usually about 5-7 amino acids long, and it is almost always preceded by a Cys-Xxx-Xxx-Xxx-Xxx-Xxx-Xxx-Xxx-Xxx (SEQ ID NO:77) (where "Xxx" is any amino acid). The residue following the heavy chain CDR1 is almost always a tryptophan, often a Trp-Val, a Trp-Ile, or a Trp-Ala. Fourteen amino acids are almost always between the last residue in CDR1 and the first in CDR2, and CDR2 typically contains 16 to 19 amino acids. CDR2 may be immediately preceded by Leu-Glu-Trp-Ile-Gly (SEQ ID NO:78) and may be immediately followed by Lys/Arg-Leu/Ile/Val/Phe/Thr/Ala-Thr/Ser/Ile/Ala. Other amino acids may precede or follow CDR2. Thirty two amino acids are almost always between the last residue in CDR2 and the first in CDR3, and CDR3 can be from about 3 to 25 residues long. A Cys-Xxx-Xxx almost always immediately precedes CDR3, and a Trp-Gly-Xxx-Gly (SEQ ID NO: 79) almost always follows CDR3.

Light chain CDR5 can be located in a VL region in the following way. CDR1 starts at approximately residue 24 of the mature antibody and is usually about 10 to 17 residues long. It is almost always preceded by a Cys. There are almost always 15 amino acids between the last residue of CDR1 and the first residue of CDR2, and CDR2 is almost always 7 residues long. CDR2 is typically preceded by Ile-Tyr, Val-Tyr, Ile-Lys, or Ile-Phe. There are almost always 32 residues between CDR2 and CDR3, and CDR3 is usually about 7 to 10 amino acids long. CDR3 is almost always preceded by Cys and usually followed by Phe-Gly-Xxx-Gly (SEQ ID NO:80).

A "linker," as meant herein, is a peptide that links two polypeptides, which can be two immunoglobulin variable regions in the context of a heterodimeric bispecific antibody. A linker can be from 2-30 amino acids in length. In some embodiments, a linker can be 2-25, 2-20, or 3-18 amino acids long. In some embodiments, a linker can be a peptide no more than 14, 13, 12, 11, 10, 9, 8, 7, 6, or 5 amino acids long. In other embodiments, a linker can be 5-25, 5-15, 4-11, 10-20, or 20-30 amino acids long. In other embodiments, a linker can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long. Exemplary linkers include, for example, the amino acid sequences TVAAP (SEQ ID NO:66), ASTKGP (SEQ ID NO:67), GGGGSGGGGS (SEQ ID NO:68), GGGGSAAA (SEQ ID NO:69), GGGGSGGGGSGGGGS (SEQ ID NO:74), and AAA, among many others.

A heterodimeric bispecific antibody "mediates cytolysis of a target cell by an immune effector cell," as meant herein, when addition of an amount from 0.001 pM to 20000 pM of the heterodimeric bispecific antibody to a cell cytolysis assay as described herein effectively elicits cytolysis of the target cells.

"Non-chemotherapeutic anti-neoplastic agents" are chemical agents, compounds, or molecules having cytotoxic or cytostatic effects on cancer cells other than chemotherapeutic agents. Non-chemotherapeutic antineoplastic agents may, however, be targeted to interact directly with molecules that indirectly affect cell division such as cell surface receptors, including receptors for hormones or growth factors. However, non-chemotherapeutic antineoplastic agents do not interfere directly with processes that are intimately linked to cell division such as, for example, DNA replication, RNA synthesis, protein synthesis, or mitotic spindle function, assembly, or disassembly. Examples of non-chemotherapeutic anti-neoplastic agents include inhibitors of Bcl2, inhibitors of farnesyltransferase, anti-estrogenic agents such as tamoxifen, anti-androgenic compounds, interferon, arsenic, retinoic acid, retinoic acid derivatives, antibodies targeted to tumor-specific antigens, and inhibitors of the Bcr-Abl tyrosine kinase (e.g., the small molecule STI-571 marketed under the trade name GLEEVEC™ by Novartis, New York and New Jersey, USA and Basel, Switzerland), among many possible non-chemotherapeutic antineoplastic agents.

A "target cell" is a cell that a heterodimeric bispecific antibody, as described herein, binds to and that is involved in mediating a disease. In some cases, a target cell can be a cell that is ordinarily involved in mediating an immune response, but is also involved in the mediation of a disease. For example in B cell lymphoma, a B cell, which is ordinarily involved in mediating immune response, can be a target cell. In some embodiments, a target cell is a cancer cell, a cell infected with a pathogen, or a cell involved in mediating an autoimmune or inflammatory disease. The heterodimeric bispecific antibody can bind to the target cell via binding to an antigen on a "target cell protein," which is a protein that is displayed on the surface of the target cell, possibly a highly expressed protein or a protein with a restricted pattern of expression that is enriched in the target cell versus other kinds of cells or tissues in the body.

"Tumor burden" refers to the number of viable cancer cells, the number of tumor sites, and/or the size of the tumor(s) in a patient suffering from a cancer. A reduction in tumor burden can be observed, for example, as a reduction in the amount of a tumor-associated antigen or protein in a patient's blood or urine, a reduction in the number of tumor cells or tumor sites, and/or a reduction in the size of one or more tumors.

A "therapeutically effective amount" of a heterodimeric bispecific antibody as described herein is an amount that has the effect of, for example, reducing or eliminating the tumor burden of a cancer patient or reducing or eliminating the symptoms of any disease condition that the protein is used to treat. A therapeutically effective amount need not completely eliminate all symptoms of the condition, but may reduce severity of one or more symptoms or delay the onset of more serious symptoms or a more serious disease that can occur with some frequency following the treated condition.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition.

When it is said that a named VH/VL pair of immunoglobulin variable regions can bind to a target cell or an immune effector cell "when they are part of an IgG antibody or scFv antibody," it is meant that an IgG antibody that contains the named VH region in both heavy chains and the named VL region in both light chains or the scFv that contains the VH/VL pair can bind to the target cell or the immune effector cell. A binding assay is described in Example 2. One of skill in the art could construct an IgG or scFv antibody containing the desired sequences given the knowledge in the art.

Heterodimeric Bispecific Antibodies

In the most general sense, a heterodimeric bispecific antibody as described herein comprises two polypeptide chains having different amino acid sequences, which, together, can bind to two different antigens. In addition, due to the inclusion of a half life-extending moiety, the heterodimeric bispecific antibodies have tunable pharmacokinetic properties, optionally including a half life between a few hours and a few days or from a few days to one or more weeks. In one embodiment, the first polypeptide chain comprises two immunoglobulin variable regions followed by a CH1 region, which is followed by a half-life extending moiety, and the second polypeptide chain comprises two immunoglobulin variable regions followed by a CL region. Optionally, the CL region can also be followed by a half life-extending moiety. This structure is illustrated in FIG. 1(1). In an alternate embodiment, the second polypeptide chain comprises two immunoglobulin variable regions followed by a CL region and then a half life-extending moiety, and the first polypeptide chain comprises two immunoglobulin variable regions followed by a CH1 region, which may or may not be followed by a half-life extending moiety. In some embodiments, the half-life extending moiety is an Fc polypeptide chain that is present on both the first and second polypeptide chains after the CH1 region and the CL region, respectively. In other embodiments, neither polypeptide chain includes a CH1 or a CL region, but at least one polypeptide chain includes a half life-extending moiety. In some such embodiments, both polypeptide chains include an Fc polypeptide chain.

More particular embodiments specify which immunoglobulin variable regions are VH or VL regions and which can associate to form a binding site for an antigen, which can be part of a protein expressed on the surface of an immune effector cell or a target cell. Generally, the antigen-binding portion of an antibody includes both a VH and a VL region, although in some cases a VH or a VL region can bind to an antigen without a partner. See, e.g., US Application Publication 2003/0114659. FIG. 1(2) illustrates an embodiment in which the two variable regions in what is referred as the first polypeptide chain (which contains a CH1 region) are two different VH regions, and the two variable regions in what is referred to as the second polypeptide chain (which contains a CL region) are two different VL regions. In this embodiment, the linkers between the two variable regions in both the first and second polypeptide chains are shorter than 12 amino acids. As a result, variable regions can pair "in parallel" to form the antigen binding sites. That is, the first VH region on the first polypeptide chain (VH1) can pair with the first VL region on the second polypeptide chain (VL1) to form a binding site for a first antigen. Further, the second VH region on the first polypeptide (VH2) can associate "in parallel" with the second VL region on the second polypeptide chain (VL2) to form a binding site for a second antigen binding site. The embodiment shown in FIG. 1(3) is similar except the order of the two VH regions and of the two VL regions is reversed. The variable regions can pair in parallel to form the antigen binding sites.

Other embodiments in which "in parallel" VH/VL interaction are required can have two VL regions on the first polypeptide chain and two VH regions on the second polypeptide chain. In another embodiment in which an "in parallel" interaction is required, the first polypeptide chain can comprise a VH region followed by a VL region and the second polypeptide chain can comprise a VL region followed by a VH region. Similarly, the first polypeptide chain could also comprise a VL region followed by a VH region, and the second polypeptide chain could comprise a VH region followed by a VL region.

FIG. 1(4) shows an embodiment in which the first variable region on the first polypeptide chain is the VH1 region, which is followed by the VL2 region. On the second polypeptide chain, the VH2 region is followed the VL1 region. In this format, the first variable region on the first polypeptide chain must associate with the second variable region on the second polypeptide chain to form a binding site for the first antigen. Similarly, the second variable region on the first polypeptide chain must associate with the first variable region on the second polypeptide chain to form a binding site for the second antigen. This situation is referred to herein as a "diagonal" interaction. Although the order of the variable regions on the first and second polypeptide chains in embodiments 1(5) and 1(6) is different, the variable regions in these embodiments must also pair in a diagonal interaction to form the antigen binding sites.

Between the two immunoglobulin variable regions on each polypeptide chain is a peptide linker, which can be the same on both polypeptide chains or different. The linkers can play a role in the structure of the antibody. If the linker is short enough, i.e., less than or no more than 14, 13, 12 or 10 amino acids long, it will not allow enough flexibility for the two variable regions on a single polypeptide chain to interact to form an antigen binding site. Thus, short linkers make it more likely that a variable region will interact with a variable region on the other polypeptide chain to form an antigen binding site, rather than interacting with a variable region on the same polypeptide chain. If the linker is at least 15 amino acids long, it will allow a variable region to interact with another variable region on the same polypeptide chain to form an antigen binding site.

There may or may not be a linker between the CH1 region on the first polypeptide chain and the variable region immediately upstream from it. Similarly, there may or may not be a linker between the CL region on the second polypeptide chain and the linker immediately upstream from it. If present, these linkers can be from 1 to 50, 20 to 40, 1 to 5, 1 to 10, or 10 to 20 amino acids long. Alternatively, these linkers can be absent.

A half life-extending moiety can be, for example, an Fc polypeptide, albumin, an albumin fragment, a moiety that binds to albumin or to the neonatal Fc receptor (FcRn), a derivative of fibronectin that has been engineered to bind albumin or a fragment thereof, a peptide, a single domain protein fragment, or other polypeptide that can increase serum half life. In alternate embodiments, a half life-extending moiety can be a non-polypeptide molecule such as, for example, polyethylene glycol (PEG). Sequences of human IgG1, IgG2, IgG3, and IgG4 Fc polypeptides that could be used are provided in SEQ ID NOs:2-5. Variants of these sequences containing one or more heterodimerizing alterations, one or more Fc alteration that extends half life, one or more alteration that enhances ADCC, and/or one or more alteration that inhibits Fc gamma receptor (FcγR) binding are also contemplated, as are other close variants containing not more than 10 deletions, insertions, or substitutions of a single amino acid per 100 amino acids of sequence.

The sequence of a derivative of human fibronectin type III (Fn3) engineered to bind albumin is provided in SEQ ID NO:1. As is known in the art, the loops of a human fibronectin type III (Fn3) domain can be engineered to bind to other targets. Koide (1998), *J Mol Biol:* 284(4): 1141-51. Exemplary pairs of amino acid sequences that make up heterodimeric bispecific antibodies that contain an engineered fibronectin type III domain that can bind to albumin as a half life-extending moiety include the following: SEQ ID NOs:6 and 7; SEQ ID NOs:8 and 9; SEQ ID NOs:10 and 11; SEQ ID NO:s:12 and 13, and SEQ ID NOs:14 and 15.

The half life extending moiety can be an Fc region of an antibody. If so, the first polypeptide chain can contain an Fc polypeptide chain after the CH1 region, and the second polypeptide chain can contain an Fc polypeptide chain after the CL region. Alternatively, only one polypeptide chain can contain an Fc polypeptide chain. There can be, but need not be, a linker between the CH1 region and the Fc region and/or between the CL region and the Fc region. As explained above, an Fc polypeptide chain comprises all or part of a hinge region followed by a CH2 and a CH3 region. The Fc polypeptide chain can be of mammalian (for example, human, mouse, rat, rabbit, dromedary, or new or old world monkey), avian, or shark origin. In addition, as explained above, an Fc polypeptide chain can include a limited number alterations. For example, an Fc polypeptide chain can comprise one or more heterodimerizing alterations, one or more alteration that inhibits or enhances binding to FcγR, or one or more alterations that increase binding to FcRn. Exemplary amino acid sequences of pairs of polypeptide chains that make up a heterodimeric bispecific antibody containing an Fc region include the following pairs of sequences: SEQ ID NOs:16 and 17; SEQ ID NOs:18 and 19; SEQ ID NOs:20 and 21; SEQ ID NOs:84 and 86; and SEQ ID NOs:94 and 96.

In some embodiments the amino acid sequences of the Fc polypeptides can be mammalian, for example a human, amino acid sequences. The isotype of the Fc polypeptide can be IgG, such as IgG1, IgG2, IgG3, or IgG4, IgA, IgD, IgE, or IgM. Table 2 below shows an alignment of the amino acid sequences of human IgG1, IgG2, IgG3, and IgG4 Fc polypeptide chains.

TABLE 2

Amino acid sequences of human IgG Fc polypeptide chains

```
IgG1   ------------------------------------------------
IgG2   ------------------------------------------------
IgG3   ELKTPLGDTTHTCPRCPEPKSCDTPPPCPRCPEPKSCDTPPPCPRCP
IgG4   ------------------------------------------------

225       235       245       255       265       275
               *         *         *         *         *         *
IgG1   EPKSCDKTHTCPPCPAPELLGGPSVFLEPPKPKDTLMISRTPEVTCVVVDVSHEDPEVKF
IgG2   ERKCCVE---CPPCPAPPVA-GPSVFLEPPKPKDTLMISRTPEVTCVVVDVSHEDPEVQF
IgG3   EPKSCDTPPPCPRCPAPELLGGPSVFLEPPKPKDTLMISRTPEVTCVVVDVSHEDPEVQF
IgG4   ESKYG---PPCPSCPAPEFLGGPSVFLFPPKPKDTLMISRTPEVTCVVVDVSQEDPEVQF 285       295       305       315       325       335
               *         *         *         *         *         *
IgG1   NWYVDGVEVHNAKTKPREEQYNSTYRVVSVLTVLHQDWLNGKEYKCKVSNKALPAPIEKT
IgG2   NWYVDGMEVHNAKTKPREEQFNSTFRVVSVLTVVHQDWLNGKEYKCKVSNKGLPAPIEKT
IgG3   KWYVDGVEVHNAKTKPREEQYNSTFRVVSVLTVLHQDWLNGKEYKCKVSNKALPAPIEKT
IgG4   NWYVDGVEVHNAKTKPREEQFNSTYRVVSVLTVLHQDWLNGKEYKCKVSNKGLPSSIEKT 345       355       365       375       385       395
               *         *         *         *         *         *
IgG1   ISKAKGQPREPQVYTLPPSREEMTKNQVSLTCLVKGFYPSDIAVEWESNGQPENNYKTTP
IgG2   ISKTKGQPREPQVYTLPPSREEMTKNQVSLTCLVKGFYPSDIAVEWESNGQPENNYKTTP
IgG3   ISKTKGQPREPQVYTLPPSREEMTKNQVSLTCLVKGFYPSDIAVEWESSGQPENNYNTTP
IgG4   ISKAKGQPREPQVYTLPPSQEEMTKNQVSLTCLVKGFYPSDIAVEWESNGQPENNYKTTP 405       415       425       435       445
               *         *         *         *         *
IgG1   PVLDSDGSFFLYSKLTVDKSRWQQGNVFSCSVMHEALHNHYTQKSLSLSPGK  (SEQ ID NO: 2)
IgG2   PMLDSDGSFFLYSKLTVDKSRWQQGNVFSCSVMHEALHNHYTQKSLSLSPGK  (SEQ ID NO: 3)
IgG3   PMLDSDGSFFLYSKLTVDKSRWQQGNIFSCSVMHEALHNRFTQKSLSLSPGK  (SEQ ID NO: 4)
IgG4   PVLDSDGSFFLYSRLTVDKSRWQEGNVFSCSVMHEALHNHYTQKSLSLSLGK  (SEQ ID NO: 5)
```

The numbering shown in Table 2 is according the EU system of numbering, which is based on the sequential numbering of the constant region of an IgG1 antibody. Edelman et at (1969), Proc. Natl. Acad. Sci. 63: 78-85. Thus, it does not accommodate the additional length of the IgG3 hinge well. It is nonetheless used here to designate positions in an Fc region because it is still commonly used in the art to refer to positions in Fc regions. The hinge regions of the IgG1, IgG2, and IgG4 Fc polypeptides extend from about position 216 to about 230. It is clear from the alignment that the IgG2 and IgG4 hinge regions are each three amino acids shorter than the IgG1 hinge. The IgG3 hinge is much longer, extending for an additional 47 amino acids upstream. The CH2 region extends from about position 231 to 340, and the CH3 region extends from about position 341 to 447.

Naturally occurring amino acid sequences of Fc polypeptides can be varied slightly. Such variations can include no more that 10 insertions, deletions, or substitutions of a single amino acid per 100 amino acids of sequence of a naturally occurring Fc polypeptide chain. If there are substitutions, they can be conservative amino acid substitutions, as defined above. The Fc polypeptides on the first and second polypeptide chains can differ in amino acid sequence. In some embodiments, they can include "heterodimerizing alterations," for example, charge pair substitutions, as defined above, that facilitate heterodimer formation. Further, the Fc polypeptide portions of the heterodimeric antibody can also contain alterations that inhibit or enhance FcγR binding. Such mutations are described above and in Xu et al. (2000), Cell Immunol. 200(1): 16-26, the relevant portions of which are incorporated herein by reference. The Fc polypeptide portions can also include an "Fc alteration that extends half life," as described above, including those described in, e.g., U.S. Pat. Nos. 7,037,784, 7,670,600, and 7,371,827, US Patent Application Publication 2010/0234575, and International Application PCT/US2012/070146, the relevant portions of all of which are incorporated herein by reference. Further, an Fc polypeptide can comprise "alterations that enhance ADCC," as defined above.

A heterodimeric bispecific antibody as described herein can bind to an immune effector cell through an antigen that is part of an effector cell protein and can bind to a target cell through an antigen that is part of a target cell protein. Some effector cell proteins are described in detail below. Similarly, a number of possible target cell proteins is also described below. A heterodimeric bispecific antibody can bind to any combination of an effector cell protein and a target cell protein, which can be engaged noncovalently by the bispecific heterodimeric antibody.

Nucleic Acids Encoding Heterodimeric Bispecific Antibodies

Provided are nucleic acids encoding the heterodimeric bispecific antibodies described herein. Numerous nucleic acid sequences encoding immunoglobulin regions including VH, VL, hinge, CH1, CH2, CH3, and CH4 regions are known in the art. See, e.g., Kabat et al. in SEQUENCES OF IMMUNOLOGICAL INTEREST, Public Health Service N.I.H., Bethesda, Md., 1991. Using the guidance provided herein, one of skill in the art could combine such nucleic acid sequences and/or other nucleic acid sequence known in the art to create nucleic acid sequences encoding the heterodimeric bispecific antibodies described herein. Exemplary pairs of nucleic acids encoding heterodimeric bispecific antibodies include the following: SEQ ID NOs:32 and 33; SEQ ID NOs:34 and 35; SEQ ID NOs:36 and 37; SEQ ID NOs:38 and 39, SEQ ID NOs:85 and 87; and SEQ ID NOs:95 and 97.

In addition, nucleic acid sequences encoding heterodimeric bispecific antibodies described herein can be determined by one of skill in the art based on the amino acid sequences provided herein and knowledge in the art. Besides more traditional methods of producing cloned DNA segments encoding a particular amino acid sequence, companies such as DNA 2.0 (Menlo Park, Calif., USA) and BlueHeron (Bothell, Wash., USA), among others, now routinely produce chemically synthesized, gene-sized DNAs of any desired sequence to order, thus streamlining the process of producing such DNAs.

Methods of Making the Heterodimeric Bispecific Antibodies

The heterodimeric bispecific antibodies described herein can be made using methods well known in the art. For example, nucleic acids encoding the two polypeptide chains of a heterodimeric bispecific antibody can be introduced into a cultured host cell by a variety of known methods, such as, for example, transformation, transfection, electroporation, bombardment with nucleic acid-coated microprojectiles, etc. In some embodiments the nucleic acids encoding the heterodimeric bispecific antibodies can be inserted into a vector appropriate for expression in the host cells before being introduced into the host cells. Typically such vectors can contain sequence elements enabling expression of the inserted nucleic acids at the RNA and protein levels. Such vectors are well known in the art, and many are commercially available. The host cells containing the nucleic acids can be cultured under conditions so as to enable the cells to express the nucleic acids, and the resulting heterodimeric bispecific antibodies can be collected from the cell mass or the culture medium. Alternatively, the heterodimeric bispecific antibodies can be produced in vivo, for example in plant leaves (see, e.g., Scheller et al. (2001), Nature Biotechnol. 19: 573-577 and references cited therein), bird eggs (see, e.g., Zhu et al. (2005), Nature Biotechnol. 23: 1159-1169 and references cited therein), or mammalian milk (see, e.g., Laible et al. (2012), Reprod. Fertil. Dev. 25(1): 315).

A variety of cultured host cells can be used including, for example, bacterial cells such as *Escherichia coli* or *Bacillus steorothermophilus*, fungal cells such as *Saccharomyces cerevisiae* or *Pichia pastoris*; insect cells such as lepidopteran insect cells including *Spodoptera frugiperda* cells, or mammalian cells such as Chinese hamster ovary (CHO) cells, baby hamster kidney (BHK) cells, monkey kidney cells, HeLa cells, human hepatocellular carcinoma cells, or 293 cells, among many others.

Immune Effector Cells and Effector Cell Proteins

A heterodimeric bispecific antibody as described herein can bind to a molecule expressed on the surface of an immune effector cell (called "effector cell protein" herein) and to another molecule expressed on the surface of a target cell (called a "target cell protein" herein). The immune effector cell can be a T cell, an NK cell, a monocyte, a macrophage, or a neutrophil. In some embodiments the effector cell protein is a protein included in the T cell receptor (TCR)-CD3 complex. The TCR-CD3 complex is a heteromultimer comprising a heterodimer comprising either (1) TCRα and TCRβ or (2) TCRγ and TCRδ, plus various CD3 chains from among the CD3 zeta (CD3ζ) chain, CD3 epsilon (CD3ε) chain, CD3 gamma (CD3γ) chain, and CD3 delta (CD3δ) chain. In some embodiments, a heterodimeric bispecific antibody binds to a CD3ε chain (the mature amino acid sequence of which is disclosed in SEQ ID NO:40), which may be part of a multimeric protein. Alternatively, the effector cell protein can be human and/or cynomolgus monkey TCRα, TCRβ, TCRδ, TCRγ, CD3 beta (CD3β) chain, CD3γ chain, CD3δ chain, or CD3ζ chain.

Moreover, in some embodiments, the heterodimeric bispecific antibody can also bind to a CD3ε chain from another species, such as mouse, rat, rabbit, new world monkey, and/or old world monkey species. Such species include, without limitation, the following mammalian species: *Mus musculus; Rattus rattus; Rattus norvegicus*; the cynomolgus monkey, *Macaca fascicularis*; the hamadryas baboon, *Papio hamadryas*; the Guinea baboon, *Papio papio*; the olive baboon, *Papio anubis; the yellow baboon, Papio cynocephalus*; the Chacma baboon, *Papio ursinus; Callithrix jacchus; Saguinus Oedipus*; and *Saimiri sciureus*. The mature amino acid sequence of the CD3ε chain of cynomolgus monkey is provided in SEQ ID NO:41. As is known in the art of development of protein therapeutics, having a therapeutic that can have comparable activity in humans and species commonly used for preclinical testing, such as mice and monkeys, can simplify and speed drug development. In the long and expensive process of bringing a drug to market, such advantages can be critical.

In more particular embodiments, the heterodimeric bispecific antibody can bind to an epitope within the first 27 amino acids of the CD3ε chain, which may be a human CD3ε chain or a CD3ε chain from different species, particularly one of the mammalian species listed above. The epitope that the antibody binds to can be part of an amino acid sequence selected from the group consisting of SEQ ID NO:40 and SEQ ID NO:41. The epitope can contain the amino acid sequence Gln-Asp-Gly-Asn-Glu (SEQ ID NO:81). The advantages of an antibody that binds such an epitope are explained in detail in U.S. Patent Application Publication 2010/183615, the relevant portions of which are incorporated herein by reference. The epitope to which an antibody binds can be determined by alanine scanning, which is described in, e.g., U.S. Patent Application Publication 2010/183615, the relevant portions of which are incorporated herein by reference.

Where a T cell is the immune effector cell, effector cell proteins to which a heterodimeric bispecific antibody can bind include those that are part of a TCR-CD3 complex including, without limitation, the CD3α chain, the CD3β chain, the CD3γ chain, the CD3δ chain, the CD3ε chain, the CD3ζ chain, the CD3η chain, TCRα, TCRβ, TCRγ, and TCRδ. Where an NK cell or a cytotoxic T cell is an immune effector cell, NKG2D, CD352, NKp46, or CD16a can be an effector cell protein. Where a CD8+ T cell is an immune effector cell, 4-1BB, OX40, GITR, CD28, CD27, or ICOS can be an effector cell protein. Alternatively, a heterodimeric bispecific antibody could bind to other effector cell proteins expressed on T cells, NK cells, macrophages, monocytes, or neutrophils.

Target Cells and Target Cell Proteins Expressed on Target Cells

As explained above, a heterodimeric bispecific antibody as described herein binds to an effector cell protein and a target cell protein. The target cell protein can, for example, be expressed on the surface of a cancer cell (i.e., a cancer cell antigen), a cell infected with a pathogen, or a cell that mediates an inflammatory or autoimmune condition. In some embodiments, the target cell protein can be highly expressed on the target cell, although this is not required.

Where the target cell is a cancer cell, a heterodimeric bispecific antibody as described herein can bind to a cancer cell antigen as described above. A cancer cell antigen can be a human protein or a protein from another species. For example, a heterodimeric bispecific antibody may bind to a target cell protein from a mouse, rat, rabbit, new world monkey, and/or old world monkey species, among many others. Such species include, without limitation, the following species: *Mus musculus; Rattus rattus; Rattus norvegicus*; cynomolgus monkey, *Macaca fascicularis*; the hamadryas baboon, *Papio hamadryas*; the Guinea baboon, *Papio papio*; the olive baboon, *Papio anubis*; the yellow baboon, *Papio cynocephalus*; the Chacma baboon, *Papio ursinus, Callithrix jacchus, Saguinus oedipus*, and *Saimiri sciureus*.

In some examples, the target cell protein can be a protein selectively expressed on an infected cell. For example, in the case of a hepatitis B virus (HBV) or hepatitis C virus (HCV) infection, the target cell protein can be an envelope protein of HBV or HCV that is expressed on the surface of an infected cell. In other embodiments, the target cell protein can be gp120 encoded by human immunodeficiency virus (HIV) on HIV-infected cells.

In a condition where it is desirable to deplete regulatory T cells, such as in a cancer or an infectious disease, regulatory T cells can be target cells. If so, CCR4 can be a target cell protein.

In other aspects, a target cell can be a cell that mediates an autoimmune or inflammatory disease. For example, human eosinophils in asthma can be target cells, in which case, EGF-like module containing mucin-like hormone receptor (EMR1), for example, can be a target cell protein. Alternatively, excess human B cells in a systemic lupus erythematosus patient can be target cells, in which case CD19 or CD20, for example, can be a target cell protein. In other autoimmune conditions, excess human Th2 T cells can be target cells, in which case CCR4 can, for example, be a target cell protein. Similarly, a target cell can be a fibrotic cell that mediates a disease such as atherosclerosis, chronic obstructive pulmonary disease (COPD), cirrhosis, scleroderma, kidney transplant fibrosis, kidney allograft nephropathy, or a pulmonary fibrosis, including idiopathic pulmonary fibrosis and/or idiotypic pulmonary hypertension. For such fibrotic conditions, fibroblast activation protein alpha (FAP alpha) can, for example, be a target cell protein.

Target Cell Cytolysis Assays

In the Examples below, an assay for determining whether a heterodimeric bispecific antibody as described herein can induce cytolysis of a target cell by an immune effector cell in vitro is described. In this assay, the immune effector cell is a T cell. The following very similar assay can be used where the immune effector cells are NK cells.

A target cell line expressing the target cell protein of interest can be labeled with 2 μM carboxyfluorescein succinimidyl ester (CFSE) for 15 minutes at 37° C. and then washed. An appropriate number of labeled target cells can then be incubated in one or more 96 well flat bottom culture plates for 40 minutes at 4° C., with or without a bispecific protein, a control protein, or no added protein at varying concentrations. NK cells isolated from healthy human donors can be isolated using the Miltenyi NK Cell Isolation Kit II (Miltenyi Biotec, Auburn, Calif.) and then added to the target cells at an Effector:Target ratio of 10:1. Other effector:

target ratios can also be appropriate. The NK cells, which are the immune effector cells in this assay, can be used immediately post-isolation or after overnight culture at 37° C. Plates containing tumor target cells, bispecific proteins, and immune effector cells can be cultured for 18-24 hours at 37° C. with 5% $CO_2$. Appropriate control wells can also be set up. After the 18-24 hour assay period, all cells can be removed from the wells. A volume of a 7-AAD solution equal to the volume of the content of the wells can be added to each sample. Samples can then assayed to determine the percentage of live versus dead target cells via flow cytometry as described in the Examples below.

Therapeutic Methods and Compositions

The heterodimeric bispecific antibodies described herein can be used to treat a wide variety of conditions including, for example, various forms of cancer, infections, fibrotic diseases, and/or autoimmune or inflammatory conditions.

Provided herein are pharmaceutical compositions comprising the heterodimeric bispecific antibodies described herein. Such pharmaceutical compositions comprise a therapeutically effective amount of a heterodimeric bispecific antibody, as described herein, plus one or more additional components such as a physiologically acceptable carrier, excipient, or diluent. Such additional components can include buffers, carbohydrates, polyols, amino acids, chelating agents, stabilizers, and/or preservatives, among many possibilities.

In some embodiments, the heterodimeric, bispecific antibodies described herein can be used to treat cell proliferative diseases, including cancer, which involve the unregulated and/or inappropriate proliferation of cells, sometimes accompanied by destruction of adjacent tissue and growth of new blood vessels, which can allow invasion of cancer cells into new areas, i.e., metastasis. These conditions include hematologic malignancies and solid tumor malignancies. Included within conditions treatable with the heterodimeric bispecific antibodies described herein are non-malignant conditions that involve inappropriate cell growth, including colorectal polyps, cerebral ischemia, gross cystic disease, polycystic kidney disease, benign prostatic hyperplasia, and endometriosis. Other cell proliferative diseases that can be treated using the heterodimeric bispecific antibodies of the present invention are, for example, cancers including mesotheliomas, squamous cell carcinomas, myelomas, osteosarcomas, glioblastomas, gliomas, carcinomas, adenocarcinomas, melanomas, sarcomas, acute and chronic leukemias, lymphomas, and meningiomas, Hodgkin's disease, Sézary syndrome, multiple myeloma, and lung, non-small cell lung, small cell lung, laryngeal, breast, head and neck, bladder, ovarian, skin, prostate, cervical, vaginal, gastric, renal cell, kidney, pancreatic, colorectal, endometrial, and esophageal, hepatobiliary, bone, skin, and hematologic cancers, as well as cancers of the nasal cavity and paranasal sinuses, the nasopharynx, the oral cavity, the oropharynx, the larynx, the hypolarynx, the salivary glands, the mediastinum, the stomach, the small intestine, the colon, the rectum and anal region, the ureter, the urethra, the penis, the testis, the vulva, the endocrine system, the central nervous system, and plasma cells.

Among the texts providing guidance for cancer therapy is *Cancer, Principles and Practice of Oncology*, 4th Edition, DeVita et at, Eds. J. B. Lippincott Co., Philadelphia, Pa. (1993). An appropriate therapeutic approach is chosen according to the particular type of cancer, and other factors such as the general condition of the patient, as is recognized in the pertinent field. The heterodimeric bispecific antibodies described herein may be added to a therapy regimen using other anti-neoplastic agents and/or treatments in treating a cancer patient.

In some embodiments, the heterodimeric bispecific antibodies can be administered concurrently with, before, or after a variety of drugs and treatments widely employed in cancer treatment such as, for example, chemotherapeutic agents, non-chemotherapeutic, anti-neoplastic agents, and/or radiation. For example, chemotherapy and/or radiation can occur before, during, and/or after any of the treatments described herein. Examples of chemotherapeutic agents are discussed above and include, but are not limited to, cisplatin, taxol, etoposide, mitoxantrone (Novantrone®), actinomycin D, cycloheximide, camptothecin (or water soluble derivatives thereof), methotrexate, mitomycin (e.g., mitomycin C), dacarbazine (DTIC), anti-neoplastic antibiotics such as adriamycin (doxorubicin) and daunomycin, and all the chemotherapeutic agents mentioned above.

The heterodimeric bispecific antibodies described herein can also be used to treat infectious disease, for example a chronic hepatitis B virus (HBV) infection, a hepatitis C virus (HPC) infection, a human immunodeficiency virus (HIV) infection, an Epstein-Barr virus (EBV) infection, or a cytomegalovirus (CMV) infection, among many others.

The heterodimeric bispecific antibodies described herein can find further use in other kinds of conditions where it is beneficial to deplete certain cell types. For example, depletion of human eosinophils in asthma, excess human B cells in systemic lupus erythematosus, excess human Th2 T cells in autoimmune conditions, or pathogen-infected cells in infectious diseases can be beneficial. Depletion of myofibroblasts or other pathological cells in fibrotic conditions such as lung fibrosis, such as idiopathic pulmonary fibrosis (IPF), or kidney or liver fibrosis is a further use of a heterodimeric bispecific antibody.

Therapeutically effective doses of the heterodimeric bispecific antibodies described herein can be administered. The amount of antibody that constitutes a therapeutically dose may vary with the indication treated, the weight of the patient, the calculated skin surface area of the patient. Dosing of the bispecific proteins described herein can be adjusted to achieve the desired effects. In many cases, repeated dosing may be required. For example, a heterodimeric bispecific antibody as described herein can be dosed three times per week, twice per week, once per week, once every two, three, four, five, six, seven, eight, nine, or ten weeks, or once every two, three, four, five, or six months. The amount of the heterodimeric bispecific antibody administered on each day can be from about 0.0036 mg to about 450 mg. Alternatively, the dose can calibrated according to the estimated skin surface of a patient, and each dose can be from about 0.002 mg/m$^2$ to about 250 mg/m$^2$. In another alternative, the dose can be calibrated according to a patient's weight, and each dose can be from about 0.000051 mg/kg to about 6.4 mg/kg.

The heterodimeric bispecific antibodies, or pharmaceutical compositions containing these molecules, can be administered by any feasible method. Protein therapeutics will ordinarily be administered by a parenteral route, for example by injection, since oral administration, in the absence of some special formulation or circumstance, would lead to hydrolysis of the protein in the acid environment of the stomach. Subcutaneous, intramuscular, intravenous, intraarterial, intralesional, or peritoneal injection are possible routes of administration. A heterodimeric bispecific antibody can also be administered via infusion, for example intravenous or subcutaneous infusion. Topical administration is also possible, especially for diseases involving the skin. Alternatively, a heterodimeric bispecific antibody can be administered through contact with a mucus membrane, for example by intra-nasal, sublingual, vaginal, or rectal administration or administration as an inhalant. Alternatively, certain appropriate pharmaceutical compositions comprising a heterodimeric bispecific antibody can be administered orally.

Having described the invention in general terms above, the following examples are offered by way of illustration and not limitation.

EXAMPLES

Example 1

Design, Construction, and Production of Heterodimeric Bispecific Antibodies

DNA expression vectors were constructed to produce four different subtypes of heterodimeric bispecific antibodies, which are diagramed in FIG. 1 (2-6), as well as two single chain bispecific molecules, one anti-HER2/CD3ε and one anti-FOLR1/CD3ε. The single chain bispecific molecules contained two VH and two VL regions separated by linkers. Each heterodimeric bispecific antibody contained two polypeptide chains. The first polypeptide chain of each construct comprised two immunoglobulin variable regions followed by a CH1 region and an Fn3 domain that had been engineered to bind albumin, and the second polypeptide chain comprised two immunoglobulin variable regions followed by a CL region. FIG. 1(1).

The coding sequences of immunoglobulin variable regions and constant domains were amplified from DNA templates by polymerase chain reaction (PCR) using forward and reverse primers and subsequently spliced together using a common overhang sequence. See, e.g., Horton et al. (1989), Gene 77: 61-68, the portions of which explain how to perform PCR so as to unite fragments containing matching overhangs is incorporated herein by reference. The PCR products were subcloned into a mammalian expression vector which already contained sequences encoding an albumin-binding fibronection 3 (Fn3) domain (SEQ ID NO:1) and a FLAG®-polyhistidine tag (FLAG-his tag) tag. The Fn3 domain, since it binds to albumin, which is a stable serum protein, is a half-life extending moiety in these constructs. The FLAG-his tag facilitates detection and purification.

DNAs encoding the single chain bispecific molecules were made by similar methods. The amino acid sequences of the anti-HER2/CD3ε (P136629.3) and anti-FOLR1/CD3ε (P136637.3) single chain bispecific molecules are shown in SEQ ID NOs:75 and 76, respectively.

DNA vectors that encode the heterodimeric bispecific antibodies and single chain bispecific molecules were cotransfected into HEK293-6E cells, and the culture media was harvested after 6 days, concentrated, and buffer-exchanged into IMAC loading buffer. The single chain anti-HER2/CD3ε and anti-FOLR1/CD3ε molecules were purified by nickel HISTRAP® (GE Healthcare Bio-Sciences, L.L.C., Uppsala, Sweden) column chromatography and eluted with a 25 to 300 mM imidizole gradient. The elution pools were further purified by size exchange chromatography (SEC) using a preparative SUPERDEX® 200 (GE Healthcare Bio-Sciences, L.L.C., Uppsala, Sweden) column, concentrated to >1 mg/mL, and stored at −70° C. The heterodimeric bispecific antibodies were subjected to nickel HISTRAP® (GE Healthcare Bio-Sciences, L.L.C., Uppsala, Sweden) column chromatography and eluted with a 25 to 300 mM imidizole gradient. The elution pools were further purified by size exchange chromatography (SEC) using a preparative SUPERDEX® 200 (GE Healthcare Bio-Sciences, L.L.C., Uppsala, Sweden) column, concentrated to >1 mg/mL, and stored at −70° C.

In an embodiment like that shown in FIG. 1(2) (designated P57216.9), the first polypeptide chain (SEQ ID NO:6) begins with a VH region specific for human MSLN (SEQ ID NO:46), which is followed by a linker, a VH region specific for human CD3ε (SEQ ID NO:42), a CH1 region (SEQ ID NO:70), an Fn3 domain engineered to bind to human albumin (SEQ ID NO:1), and a FLAG-his tag. The second polypeptide chain (SEQ ID NO:7) begins with a VL region specific for human MSLN (SEQ ID NO:48), followed by a linker, a VL region specific for human CD3ε (SEQ ID NO:43), and a CL region (SEQ ID NO:71). Similarly, SEQ ID NOs: 8 and 9 provide the amino acid sequences of the first and second polypeptide chains, respectively, of another embodiment like that shown in FIG. 1(3) (designated P56019.5). P56019.5 has different variable regions from those used in P57216.9.

An embodiment like that shown in FIG. 1(3) (designated H71362.2) is similar to P56019.5 except that it has different anti-CD3ε variable regions and a different FN3 domain. The anti-CD3ε VH and VL regions in H71362.2 have the amino acid sequences SEQ ID NO:42 and SEQ ID NO:47, respectively, and the first and second polypeptide chains of H71362.2 have the amino acid sequences of SEQ ID NO:10 and SEQ ID NO:11, respectively.

In an embodiment like that shown in FIG. 1(4) (designated P69058.3), the first polypeptide chain (SEQ ID NO:12) begins with a VH region specific for human MSLN (SEQ ID NO:46), which is followed by a linker, a VL region specific for human CD3ε (SEQ ID NO:43), a CH1 region, an Fn3 domain (SEQ ID NO:1), and a FLAG-his tag. The second polypeptide chain (SEQ ID NO:13) begins with a VH region specific for human CD3ε (SEQ ID NO:42), followed by a linker, a VL region specific for human MSLN (SEQ ID NO:48), and a CL region (SEQ ID NO:73).

In an embodiment like that shown in FIG. 1(5) (designated P69059.3), the first polypeptide chain (SEQ ID NO:14) begins with a VL region specific for human CD3ε (SEQ ID NO:43), which is followed by a linker, a VH region specific for human MSLN (SEQ ID NO:49), a CH1 region (SEQ ID NO:70), an Fn3 domain (SEQ ID NO:1), and a FLAG-his tag. The second polypeptide chain (SEQ ID NO:15) begins with a VL region specific for human MSLN (SEQ ID NO:48), followed by a linker, a VH region specific for human CD3ε (SEQ ID NO:42), and a CL region (SEQ ID NO:73).

All constructs described above were designed such that interchain interactions between immunoglobulin variable regions were required to create a complete VH/VL antigen-binding pair for each of the two antigens. The linkers between the two immunoglobulin variable regions on each polypeptide chain were short enough, i.e., 5-10 amino acids, that interaction of variable regions on the same polypeptide chains was highly disfavored. In some cases, the first immunoglobulin variable regions on each polypeptide chain could form a complete VH/VL antigen-binding pair, and the second immunoglobulin variable regions on each polypeptide chain could form another VH/VL antigen-binding pair. See FIGS. 1(2) and 1(3) and the description of constructs P56019.5, P57216.9, and H71362.2 above. This kind of interaction is called herein an "in parallel" interaction. In other cases, the first immunoglobulin variable region on the first polypeptide chain could interact with the second immunoglobulin variable region on the second polypeptide chain to form a VH/VL antigen-binding pair, and the second immunoglobulin variable region on the first polypeptide chain could interact with the first immunoglobulin variable region on the second polypeptide chain to form a VH/VL antigen-binding pair. See FIGS. 1(4), 1(5), 1(6) and the descriptions of constructs P69058.3 and P69059.3 above. This kind of interaction is called herein an "diagonal" interaction.

Example 2

T Cell Dependent Kiting of Cancer Cells by Heterodimeric Bispecific Antibodies that Bind to MSLN and CD3ε

The heterodimeric bispecific antibodies described in Example 1 were produced in HEK 293 cells and were assayed by fluorescence activated cell sorting (FACS) for binding to T cells, which express CD3ε, and to a human ovarian cancer cell line, Ovcar-8, which expresses mesothelin. Briefly, the heterodimeric bispecific antibodies were incubated with about 50,000 Ovcar-8 cells or isolated human or cynomolgus monkey T cells at 4° C. for one hour. The cells were then washed and stained with a fluorescein isothiocyanate (FITC)-conjugated anti-human light chain secondary antibody and analyzed by flow cytometry. The relative binding was represented by the geometric mean of fluorescence intensity. As is apparent in Table 3 below, all constructs tested could bind CD3ε on human T cells and MSLN on Ovcar-8 cells.

The anti-MSLN, anti-CD3ε heterodimeric bispecific antibodies described in Example 1 were assayed to determine their cytolytic activity against cancer cells expressing MSLN in the presence of human T cells. This assay is referred to herein as the human T cell-dependent cell mediated cytolysis assay (human TDCC). A similar assay using NK cells as immune effector cells is described above. Briefly, a human ovarian cancer cell line expressing MSLN (Ovcar-8) was labelled with carboxyfluorescein diacetate succinimidyl ester (CFSE) and plated at about 20,000 cells per well in a 96-well V-bottom microtiter plate. Previously frozen isolated human T cells were thawed, washed, and added to the microtiter plate at about 200,000 cells per well. Antibodies were serially diluted to make final well concentrations ranging from 10 μg/mL to 0.01 μg/mL and added to the microtiter plate. Control wells were included which had no antibody, T cells alone, or tumor cells alone. Plates were incubated at 37° C. in a humidified environment for 40 hours. At the end of the assay, all cells from each well were collected (adherent tumor cells were removed using Trypsin-EDTA) and stained using 0.01 μM TO-PRO®-3 (Molecular Probes, Inc., Eugene, Oreg.) to assess viability. Tumor cell viability was read out using flow cytometry. Percent specific lysis was calculated according to the following formula:

% specific lysis=[% tumor cell lysis with bispecific–% tumor cell lysis without bispecific/20% of total cell lysis–% tumor cell lysis without bispecific]×100

To determine percent total cell lysis (needed to make this calculation), samples containing effector and labeled target cells without bi-specific were lysed with cold 80% methanol. Results of these assays are summarized in Table 3 below.

TABLE 3

| | | | Binding and Cytolytic Activity of Different Subtypes | | | |
|---|---|---|---|---|---|---|
| | | Amino acid sequences of the | FACS binding | | Human TDCC | |
| | Format as | first and second | (geometric mean) | | | Maximum |
| Construct ID No. | shown in FIG. 1 | polypeptide chains | Human T cells | Ovcar-8 cells | EC$_{50}$ (pM) | killing (per cent) |
| P56019.5 | FIG. 1(3) | SEQ ID NO: 8 SEQ ID NO: 9 | 220 | 285 | 0.12 | 53 |
| P57216.9 | FIG. 1(2) | SEQ ID NO: 6 SEQ ID NO: 7 | 103 | 439 | 3.50 | 49 |
| P69058.3 | FIG. 1(4) | SEQ ID NO: 12 SEQ ID NO: 13 | 290 | 588 | <0.1 | 68 |
| P69059.3 | FIG. 1(5) | SEQ ID NO: 14 SEQ ID NO: 15 | 179 | 526 | <0.1 | 68 |
| H71362.2 | FIG. 1(3) | SEQ ID NO: 10 SEQ ID NO: 11 | 354 | 575 | 0.33 | 54 |

Figure 2:
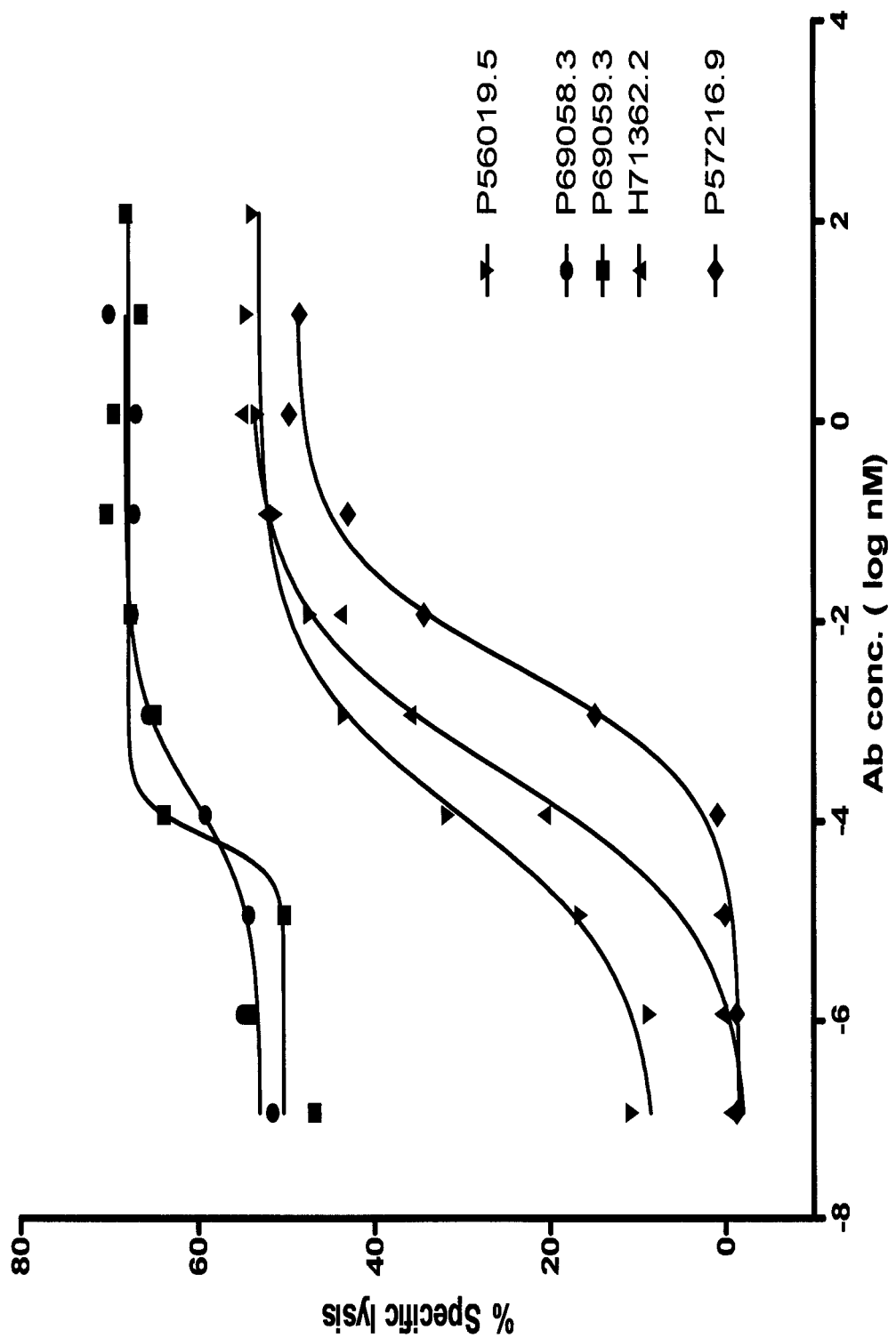
FIG. 2: Heterodimeric bispecific anti-MSLN/CD3ε antibodies induce lysis of MSLN-expressing tumor cell lines in the presence of human T cells. The x axis indicates the antibody concentration (log nM), and the y axis indication the percent specific cell lysis. All methods are described in Example 2, and the particular heterodimeric bispecific antibody constructs used are indicated in the figure.

As shown in Table 3, all of the heterodimeric bispecific antibodies tested could bind to human T cells and Ovcar-8 cells. They also exhibited cytolytic activity against tumor cells in the presence of T cells. Table 3 and FIG. 2. However, the two in which diagonal interchain variable regions interactions resulted in complete antigen binding sites, i.e., P69058.3 and P69059.3, had a combination of both low EC$_{50}$'s and high maximum killing percents, which was not observed with the other three constructs. These other three constructs were designed such that antigen binding sites could be formed by in parallel interchain interactions between variable regions. These data suggest that constructs requiring a "diagonal" interaction of variable regions may have better biological activity than those requiring in parallel interactions.

Another set of constructs was made by methods similar to those used above using the same pair of anti-MSLN VH and VL regions, i.e., SEQ ID NOs:46 and 48, as used in most constructs described above and a different pair of anti-CD3ε VH and VL regions than used in most of the constructs described above. The anti-CD3ε VH and VL regions used could bind to both human and cynomolgus monkey CD3ε. P56019.5 is the only construct described herein using a particular anti-CD3ε VH/VL pair that binds to human, but not cynomolgus monkey, CD3ε. H69070.4 has the same arrangement of variable regions (i.e., the format shown in FIG. 1(3)) and the same anti-MSLN VH/VL pair as P56019.5, but it has a different anti-CD3ε VH/VL pair, which is also present in H69071.4, H69072.4, and H71365.2. The amino acid sequences of the first and second polypeptide chains of H69070.4 are provided in SEQ ID NO:24 and SEQ ID NO:25. H69071.4, H69072.4, and H71365.2 all contain the same anti-CD3ε VH/VL pair and the same anti-MSLN VH/VL pair, but the variable regions in these constructs are arranged in different ways. See Table 4. The amino acid sequences of first and second polypeptide chains, respectively, of these constructs are as follows: H69071.4, SEQ ID NO:26 and SEQ ID NO:27; H69072.4, SEQ ID NO:28 and SEQ ID NO:29; and H71364.2, SEQ ID NO:30 and SEQ ID NO:31. These constructs were tested using the assays described above, as well as the cynomolgus monkey T cell-dependent cell cytolysis (called "cyno TDCC") assay described below.

To perform the cyno TDCC assay, T cells were purified from blood from cynomolgus monkeys as follows. First the red blood cells were lysed with ammonium chloride. Thereafter, the remaining cells were cultured until most of the cultured cells were T cells. These purified cynomolgus monkey T cells were stimulated by incubating them for 48 hrs in a microtiter plate coated with mouse anti-human CD3 in the presence of mouse anti-human CD28. Thereafter, cells were cultured in media containing 10 ng/mL human IL-2 for 7 days. For the assay, a human ovarian cancer line expressing MSLN (Ovcar-8) was labelled with CFSE and plated at 10,000 cells per well in a 96-well V-bottom microtiter plate. The stimulated cynomolgus monkey T cells were washed and added to the microtiter plate at 100,000 cells per well. Antibodies were serially diluted 1:10 to make final well concentrations ranging from 10 µg/mL down to 0.01 µg/mL and added to the microtiter plate. Control wells were included that had either no antibody, T cells alone, or tumor cells alone. Microtiter plates were incubated at 37° C. in a humidified environment for 20 hours. At the end of the assay, all cells from each well were collected (adherent tumor cells were removed using Trypsin-EDTA) and stained using 0.01 µM TO-PRO®-3 (Molecular Probes, Inc., Eugene, Oreg.) to assess viability. Tumor cell viability was read out using flow cytometry, and percent specific cell lysis was determined as described above. Results of this assay and those described above are summarized in Table 4 below.

Figure 3:
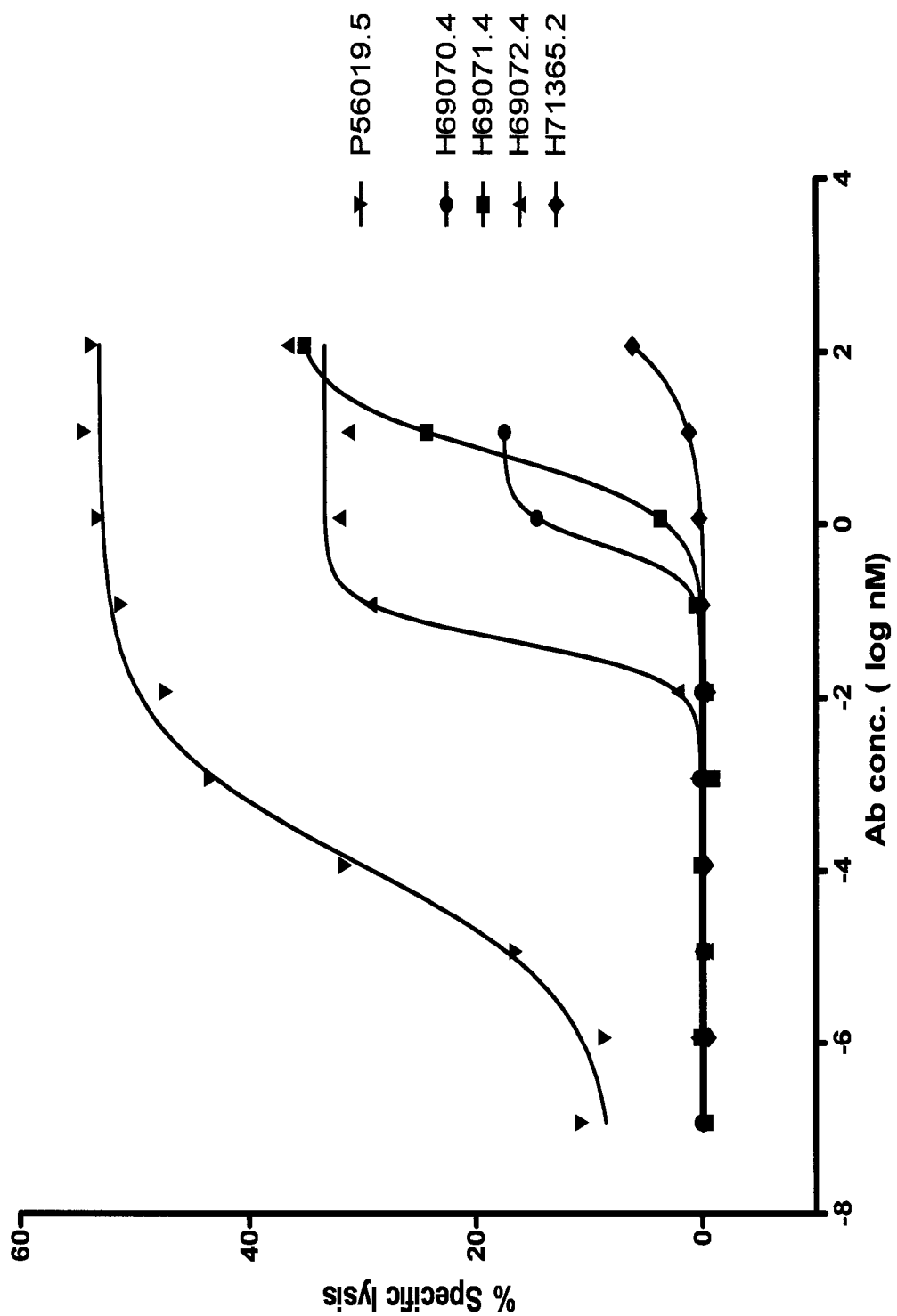
FIG. 3: Heterodimeric bispecific anti-MSLN/CD3ε antibodies induce lysis of MSLN-expressing tumor cell lines in the presence of human T cells. The x axis indicates the antibody concentration (log nM), and the y axis indicates the percent specific cell lysis. All methods are described in Example 2, and the particular heterodimeric bispecific antibody constructs used are indicated in the figure.
Figure 4:
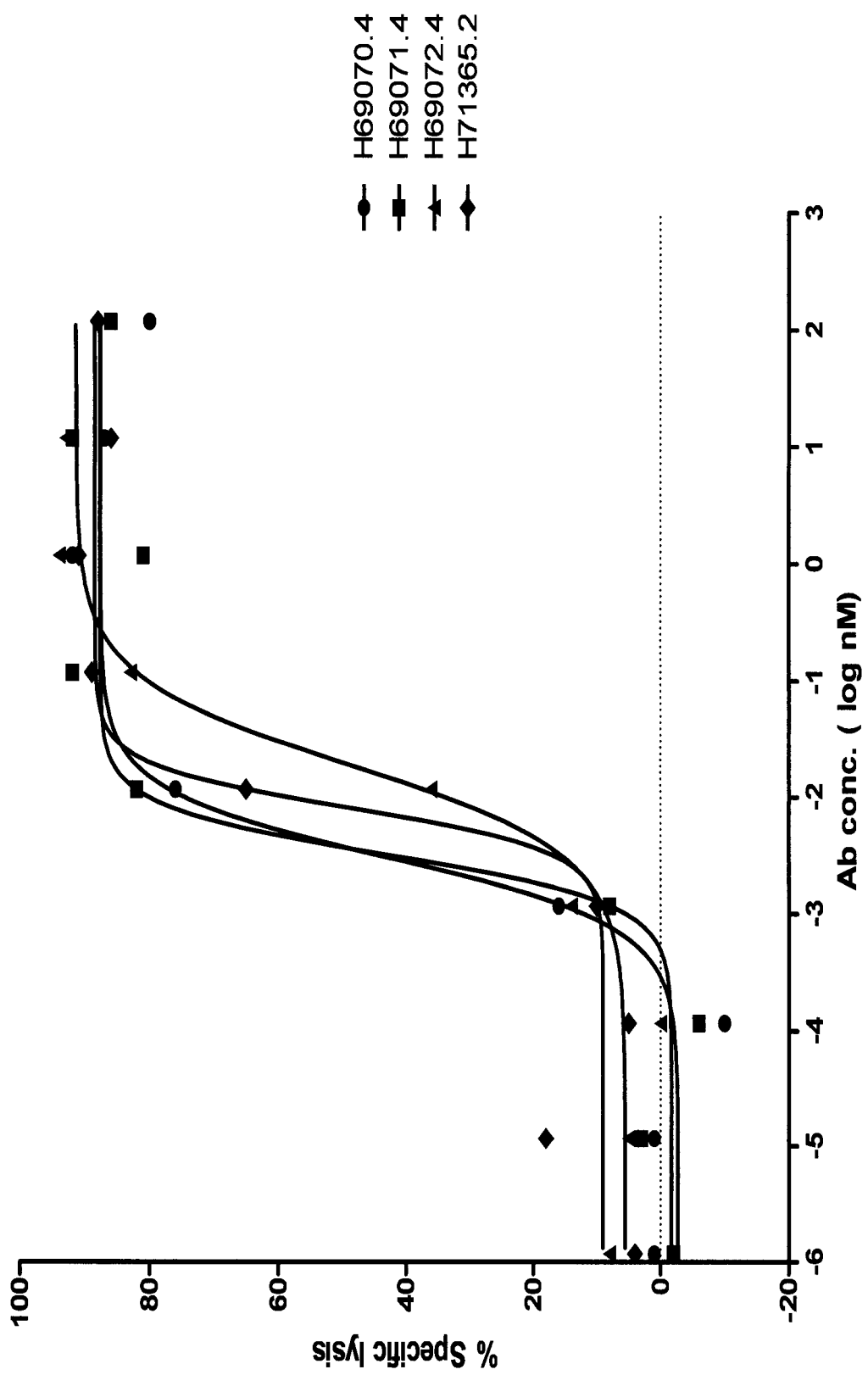
FIG. 4: Heterodimeric bispecific anti-MSLN/CD3ε antibodies induce lysis of MSLN-expressing tumor cell lines in the presence of cynomolgus monkey T cells. The x axis indicates the antibody concentration (log nM), and the y axis indicates the percent specific cell lysis. All methods are described in Example 2, and the particular heterodimeric bispecific antibody constructs used are indicated in the figure.

The data in Table 4 indicate that the CD3ε-binding VH/VL pair used in the anti-MSLN/CD3ε heterodimeric bispecific antibodies designated H69070.4, H69071.2, H69072.4, and H71364.2 binds to cynomolgus monkey CD3ε, as well as human CD3ε to a somewhat lesser extent. Interestingly, construct H69072.4 was much more potent than H69071.4 and H71365.2 (all of which contain the same VH/VL pairs) in the human TDCC assay, although the heterodimeric bispecific antibodies all exhibited roughly comparable activity in the cyno TDCC assay. Table 4 and FIGS. 3 and 4. These data suggest that the particular arrangement of the variable regions in a heterodimeric bispecific antibody can affect its biological activity, perhaps especially in situations where the binding of the variable regions is not particularly robust. For example, the data in Table 4 indicates that most constructs tested did not exhibit as much binding activity for human T cells as they did for cynomolgus monkey T cells. The variable regions were arranged such that interchain interactions resulting in antigen-binding VH/VL pairs were diagonal interactions in constructs H69072.4 and H69071.4. In parallel interactions were required for proper formation of VH/VL pairs in H71365.2. Hence, these data are consistent with the idea that a diagonal interaction of variable regions is more favourable than an in parallel interaction.

Example 3

Construction and Characterization of Heterodimeric Bispecific Antibodies Containing an Fc Region Construct P69058.3 (an anti-MSLN/CD3ε heterodimeric bispecific antibody like that diagrammed in FIG. 1(4)) was modified by the addition of an Fc polypeptide chain to its second polypeptide chain (containing a CL region) and the replacement of the Fn3 domain in the first polypeptide chain (containing a CH1 region) with an Fc polypeptide chain. The amino acid sequences of first and second polypeptides of this construct (designated as P73356.3) are provided in SEQ ID NO:16 and SEQ ID NO:17, respectively. The Fc region in these constructs is a human IgG1 Fc region containing heterodimerizing alterations. Specifically, the first polypeptide chain contains two positively charged mutations (D356K/D399K, using EU numbering as shown in Table 2),

TABLE 4

Binding and Cytolytic Activity of Different Subtypes

| Construct ID No. | Format as shown in FIG. 1 | Amino acid sequences of the first and second polypeptide chains | FACS binding (geometric mean) | | | Human TDCC | | Cyno TDCC | |
|---|---|---|---|---|---|---|---|---|---|
| | | | Human T cells | Ovcar-8 cells | Cyno T cells | EC$_{50}$ (pM) | Max killing (%) | EC$_{50}$ (pM) | Max killing (%) |
| P56019.5 | FIG. 1(3) | SEQ ID NO: 8 SEQ ID NO: 9 | 220 | 285 | NA* | 0.12 | 53 | NA | NA |
| H69070.4 | FIG. 1(3) | SEQ ID NO: 24 SEQ ID NO: 25 | 9 | 592 | 127 | 580 | 17 | 3.0 | 88 |
| H69071.4 | FIG. 1(4) | SEQ ID NO: 26 SEQ ID NO: 27 | 16 | 494 | 121 | 6500 | 35 | 3.20 | 88 |
| H69072.4 | FIG. 1(5) | SEQ ID NO: 28 SEQ ID NO: 29 | 11 | 534 | 110 | 44 | 37 | 18.80 | 91 |
| H71365.2 | FIG. 1(3) | SEQ ID NO: 30 SEQ ID NO: 31 | 66 | 558 | 276 | NA* | NA* | 8.10 | 86 |

*"NA" indicates "not applicable," since activity in the assay was minimal.

and the second polypeptide chain contains two negatively charged mutations (K409D/K392D). These changes result in the preferential formation of heterodimers, as compared to homodimers, when the two polypeptide chains are expressed together in the same cell. See WO 2009/089004. In another construct (P73352.3), the CH1 and CL regions present in P73356.3 in the first and second polypeptide chains, respectively, were removed. The amino acid sequences of the first and second polypeptide chains of P73352.3 are provided in SEQ ID NO:18 and SEQ ID NO:19, respectively.

Figure 5:
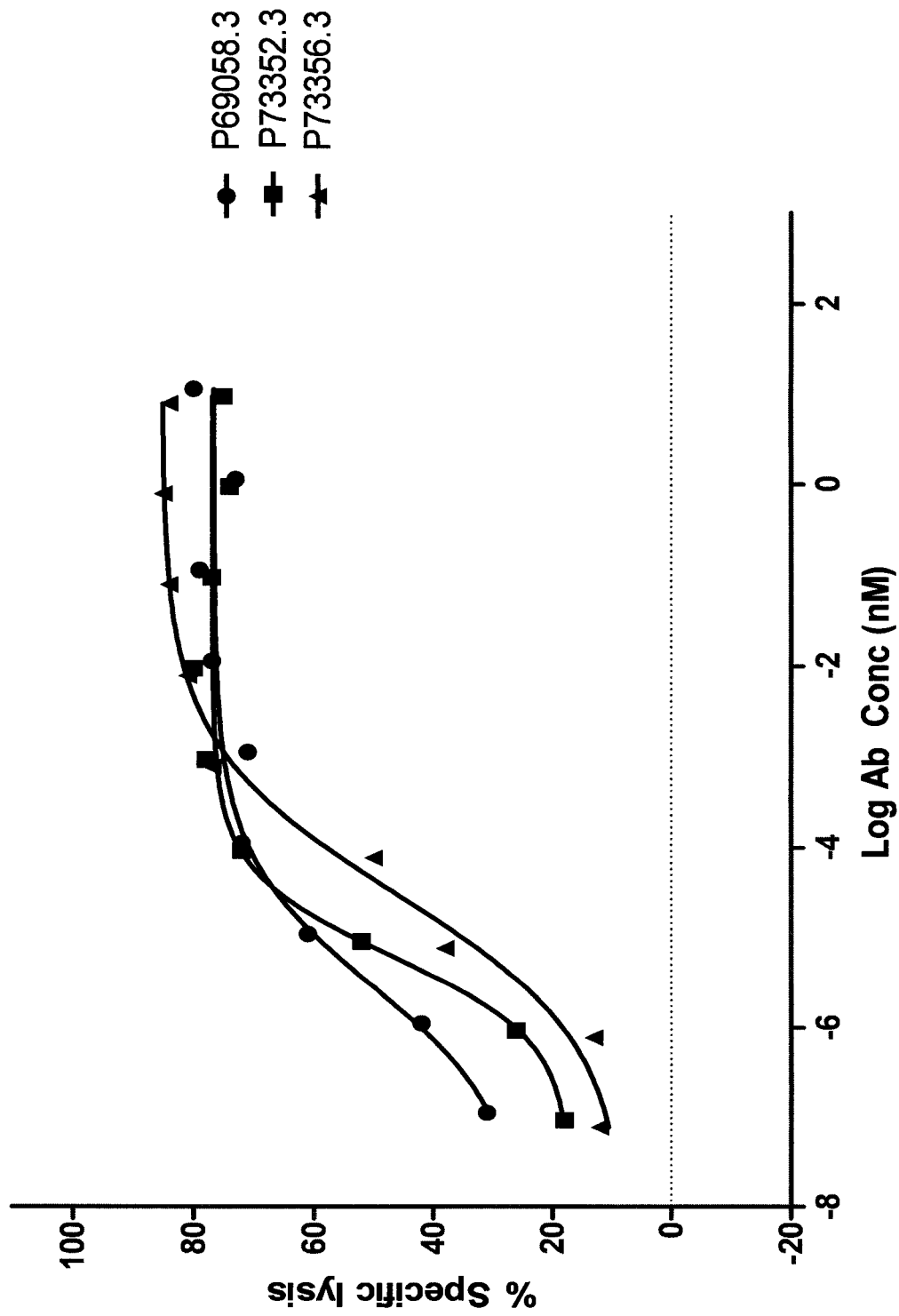
FIG. 5: Bispecific anti-MSLN/CD3ε antibodies in various formats induce lysis of MSLN-expressing tumor cell lines in the presence of human T cells. The x axis indicates the antibody concentration (log nM), and the y axis indication the percent specific cell lysis. All methods are described in Example 3, and the particular heterodimeric bispecific antibody constructs used are indicated in the figure.

The P73352.3 and P73356.3 constructs were produced in HEK 293 cells and tested together with P69058.3 in a human TDCC assay, as described above. As shown in FIG. 5, both P73352.3 and P73356.3 exhibited potent activity in mediating the killing of Ovcar-8 cells with half-maximum effective concentrations ($EC_{50}$'s) in subpicomolar range, in the same range as that of P69058.3, which does not contain an Fc region. These data demonstrated the feasibility of generating biologically potent heterodimeric bispecific antibodies that contain an Fc region, with or without the CH and CL regions, and that retain potent T cell-mediated cytolytic activity.

Example 4

Heterodimeric Anti-HER2/CD3ε Bispecific Antibody Induces Lysis of HER2-Expressing Tumor Cell Lines Using a format similar to that of the anti-MSLN/CD3ε heterodimeric bispecific antibody 73356.3 (which is in the format of FIG. 1(4) and has an Fc polypeptide chain on the C-terminal end of both the first and second polypeptide chains), P136797.3 was constructed using a VH/VL pair from an anti-HER2 antibody and a VH/VL pair from a different anti-CD3ε antibody. The format of P136797.3 is shown in FIG. 1(6). The Fc region of P136797.3 contains additional mutations (L234A/L235A, according to the EU numbering scheme shown in Table 2) to prevent binding to FcγRs. The amino acid sequences of the first and second polypeptide chains of P136797.3 are provided in SEQ ID NO:20 and SEQ ID NO:21, respectively. An anti-HER2/CD3ε single chain bispecific molecule (P136629.3, having the amino acid sequence of SEQ ID NO:75) was also used in the following assays.

Binding of the anti-HER2/CD3ε bispecific heterodimeric antibody P136797.3 and the single chain bispecific P136629.3 to purified human pan T cells and HER2-expressing tumor cells (JIMT-1) cells was assessed. Each cell type was incubated for 16 hours at 4° C. in the presence and absence (as a negative control) of each of these bispecifics. Binding of the bispecific heterodimeric antibody was detected with Allophycocyanin (APC)-labeled secondary antibodies. Binding of the single chain bispecific, which has a FLAG tag, was detected using a mouse anti-FLAG antibody followed by an APC-labeled mouse specific antibody. The level of fluorescent signal was assessed by fluorescence activated cell sorting (FACS). The levels of binding detected with both bispecifics to both human pan T cells and JIMT-1 tumor cells were clearly were distinguishable from levels detected in negative controls. Data not shown. Hence, both bispecifics bind to both T cells and JIMT-1 cells.

Pan T effector cells from human healthy donors were isolated using the Pan T Cell Isolation Kit II, human, Miltenyi Biotec, Auburn, Calif.) and incubated with CFSE-labeled target cells at a ratio of 10:1 (T cell:target cells) in the presence or absence of P136797.3 at varying concentrations. The target cells were either JIMT-1 cells (expressing about 181,000 molecules of HER2 per cell on their cell surface), T47D cells (expressing about 61,000 molecules of HER2 per cell on their cell surface), or SHP77 cells (expressing no detectable HER2 on their cell surface). Following 39-48 hours of incubation, cells were harvested, and tumor cell lysis was monitored by 7AAD uptake using flow cytometry. Percent specific lysis was determined as described in Example 2 above.

Figure 6:
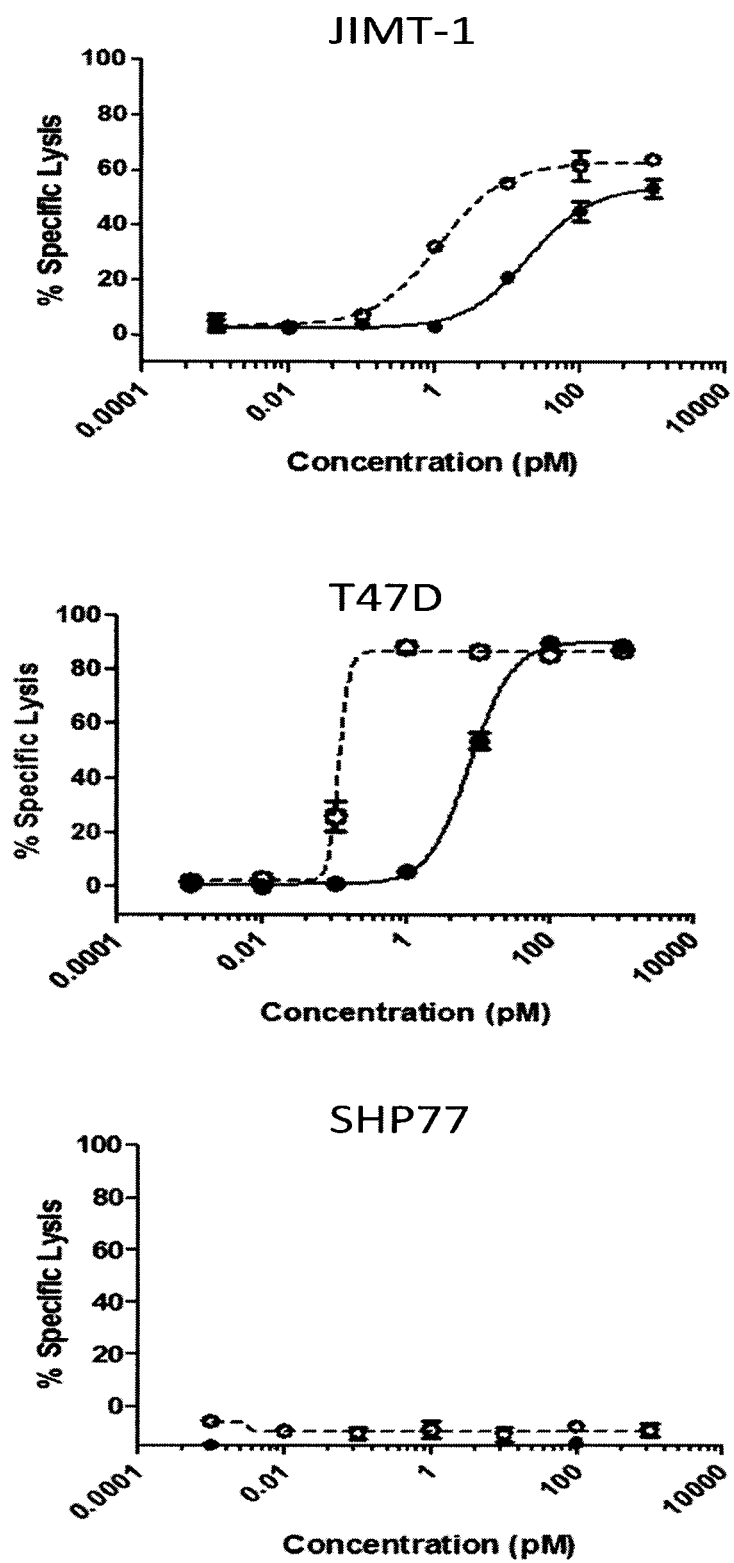
FIG. 6: A heterodimeric bispecific anti-HER2/CD3ε antibody (P136797.3, solidly filled circles and solid lines) and anti-HER2/CD3ε single chain bispecific molecule (P136629.3, open circles and dashed lines) induces lysis of HER2-expressing tumor cell lines (JIMT-1 and T47D) in the presence of human T cells. The x axis indicates antibody concentration (pM), and the y axis indicates percent specific cell lysis. The cell line used, i.e., JIMT-1, T47D, or SHP77 (which does not express HER2), is indicated in each panel. Methods are disclosed in Example 4.

Specific lysis of both JIMT-1 and T47D cells was observed in the presence of appropriate concentrations of P136797.3 or the single chain anti-HER2/CD3ε bispecific. The concentrations for half maximal lysis ($EC_{50}$'s) for P136797.3 were 19.05 pM and 7.75 pM in JIMT-1 and T47D cells, respectively. For the single chain anti-HER2/CD3ε bispecific the $EC_{50}$'s were 1.12 pM and 0.12 in JIMT-1 and T47D cells, respectively. There was no specific lysis of the HER2-negative cell line SHP77 observed. FIG. 6. In addition, lysis of JIMT-1 and T47D cells in the presence of the heterodimeric anti-HER2/CD3ε bispecific antibody did not occur in the absence of T cells. See FIG. 7; remaining data not shown. These observations suggest that both the heterodimeric anti-HER2/CD3ε bispecific antibody and the single chain anti-HER2/CD3ε bispecific are highly specific and potent reagents capable of inducing tumor cell lysis by T cells.

Figure 7:
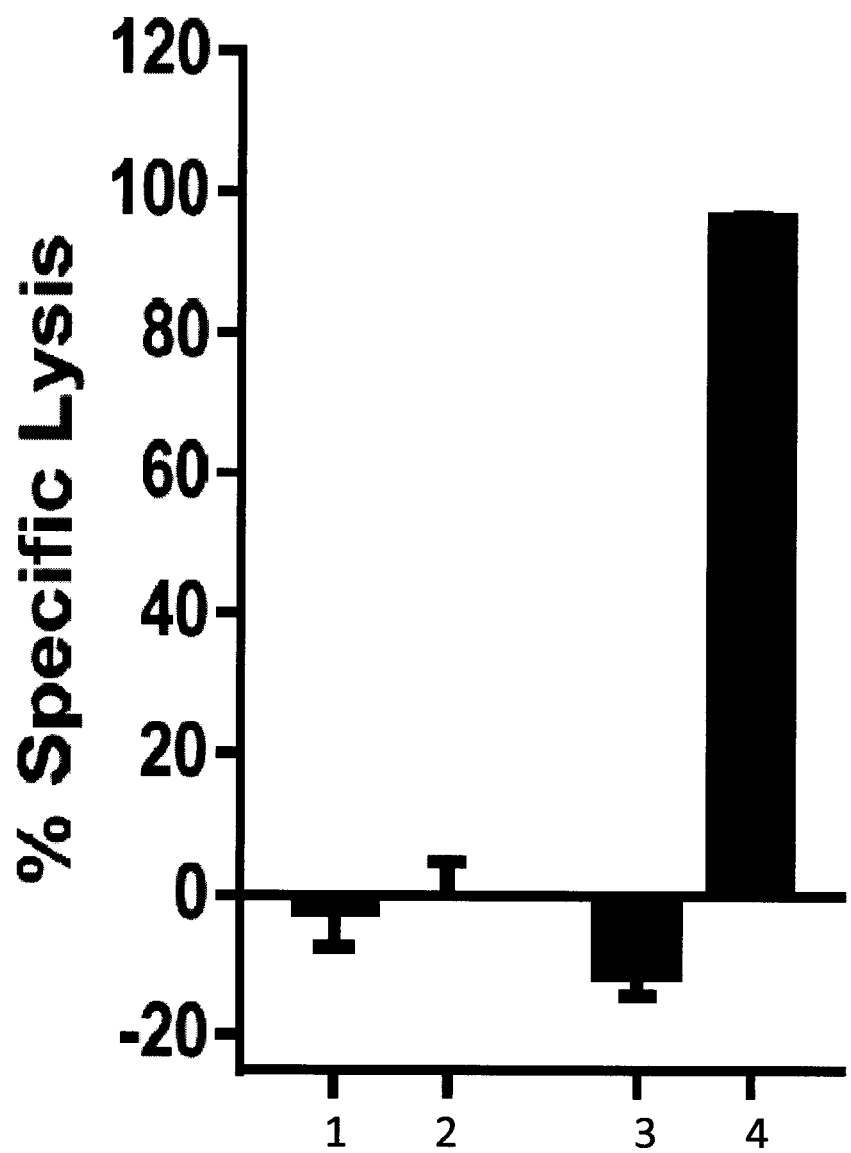
FIG. 7: Lysis of HER2-expressing tumor target cells in the presence of an anti-HER2/CD3ε heterodimeric bispecific antibody occurs in the presence, but not in the absence of T cells. Methods are described in Example 4. The y axis indicates the percent specific lysis of the JIMT-1 cells. As indicated on the x axis, the various bars represent samples containing (1) JIMT-1 cells only without the bispecific, (2) JIMT-1 cell plus T cells without the bispecific, (3) JIMT-1 cells only in the presence of the anti-HER2/CD3ε heterodimeric bispecific antibody, and (4) JIMT-1 cells plus T cells in the presence of the anti-HER2/CD3ε heterodimeric bispecific antibody.

The following control experiment was also done. Using the methods explained immediately above, samples containing JIMT-1 cells with or without pan T effectors cells in the presence or absence of the anti-HER2/CD3ε heterodimeric bispecific antibody were assayed to determine the percent specific lysis of the JIMT-1 cells. Results are shown in FIG. 7. These data indicate that essentially no lysis of the JIMT-1 cells occurred without both the bispecific and the T cells. In the presence of both T cells and the bispecific, lysis of the JIMT-1 cells occurred.

Example 5

CD3" Peripheral Blood T Cells in the Presence of PBMC's and a Heterodimeric Bispecific Antibody are not Activated Unless Target Cells are Present The following experiment was done to determine whether T cells from peripheral blood could upregulate expression of CD25 and CD69 ex vivo in the presence of the heterodimeric anti-HER2/CD3ε bispecific antibody (P136797.3) or the anti-HER2/CD3ε single chain bispecific molecule (P136629.3) described above in the presence or absence of HER2-expressing JIMT-1 cells. CD25 and CD69 are considered to be markers for activation of T cells.

Peripheral blood mononuclear cells (PBMC) from healthy donors were purified on a FICOLL™ gradient from human leukocytes purchased from Biological Specialty Corporation of Colmar, Pennsylvania. These PBMC were incubated with P136797.3 or the single chain bispecific molecule at varying concentrations in the absence and presence of the HER2-expressing JIMT-1 tumor cell line. In each sample containing JIMT-1 cells, the ratio of PBMC:JIMT-1 cells was 10:1. Following 48 hours of incubation, non-adherent cells were removed from the wells and divided into two equal samples. Flow cytometry staining was performed to detect the percent of $CD3^+$ T cells expressing CD25 or CD69. All samples were stained with a fluorescein isothiocyanate (FITC) conjugated anti-human CD3 antibody. Antibodies against human CD25 and CD69 were allophycocyanin (APC) conjugated. The stained samples were analyzed by FACS.

Figure 8:
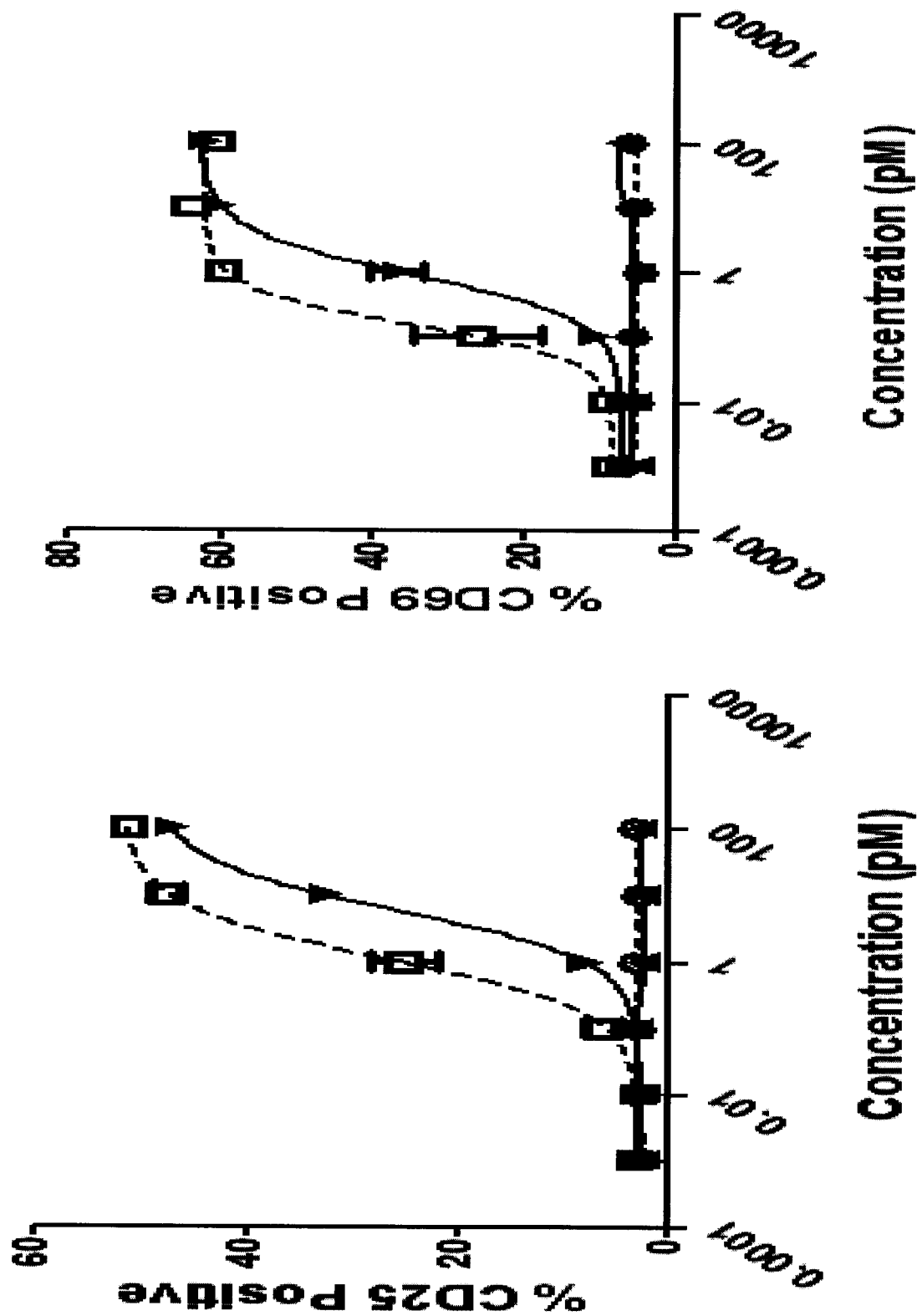
FIG. 8: Peripheral CD3$^+$ T cells show CD25 and CD69 up-regulation in response to anti-HER2/CD3ε heterodimeric bispecfic antibody or single chain anti-HER2/CD3ε bispecific antibody treatment in the presence of HER2-expressing tumor target cells. Expression of CD25 (left panel) and CD69 (right panel) in CD3$^+$ peripheral blood T cells was measured by fluorescence activated cell sorting (FACS) as explained in Example 5. The x axis indicates the concentration of the anti-HER2/CD3ε heterodimeric bispecific antibody (P136797.3) or the single chain anti-HER2/CD3ε bispecific antibody (P136629.3) (pM) in both panels, and the y axis indicates the percent of CD3$^+$ cells that were also CD25 positive (left panel) or CD69 positive (right panel). Symbols indicate as follows: open squares connected by dashed lines, single chain anti-HER2/CD3ε bispecific antibody with tumor target cells; filled, downward pointed triangles connected by solid lines, anti-HER2/CD3ε heterodimeric bispecfic antibody with tumor target cells; open circles connected by dashed lines, single chain anti-HER2/CD3ε bispecific antibody without tumor target cells; and filled, upward pointing triangles, anti-HER2/CD3ε heterodimeric bispecfic antibody without tumor target cells.

As shown in FIG. 8, up-regulation of CD25 and CD69 in CD3+ peripheral T cells was observed with the anti-HER2/CD3ε heterodimeric bispecific antibody P136797.3 and the single chain bispecific molecule. This occurred in the presence, but not in the absence, of HER2-expressing JIMT-1 tumor cells. FIG. 8. These data indicate that T cell activation by the anti-HER2/CD3ε heterodimeric bispecific antibody P136797.3 or the single chain bispecific molecule is dependent on the presence of tumor target cells expressing HER2, even though Fc receptor-bearing cells other than T cells are present in PBMC.

Example 6

Construction and Testing of an Anti-FOLR1×Anti-CD3ε Heterodimeric Bispecific Antibody In a design similar to that of P136797.3, a heterodimeric bispecific antibody that can bind CD3ε and folate receptor 1 (FOLR1), was constructed essentially as described in Example 1. It was designated P136795.3. As with P136797.3, the Fc region of P136795.3 contains both charge pair substitutions and mutations blocking binding of FcγR's. The sequences of the first and second polypeptide chains of P136795.3 are provided in SEQ ID NO:22 and SEQ ID NO:23, respectively. An anti-FOLR1/CD3ε single chain bispecific molecule (having the amino acid sequence of SEQ ID NO:76) described in Example 1 was also included in this experiment.

Human T cells isolated from healthy donors as described above were incubated with CFSE-labeled tumor target cells at a ratio of 10:1 in the presence and absence of the anti-FOLR1/CD3ε heterodimeric bispecific antibody P136795.3. Target cells were either Cal-51 cells (expressing about 148,000 FOLR1 sites/cell), T47D cells (expressing about 101,000 FOLR1 sites/cell), or BT474 cells, which do not express detectable amounts of FOLR1. Following 39-48 hours, cells were harvested and tumor cell lysis was monitored by 7AAD uptake, which stains dead or dying cells but not viable cells, using flow cytometry. Percent specific lysis was determined as described above.

Figure 9:
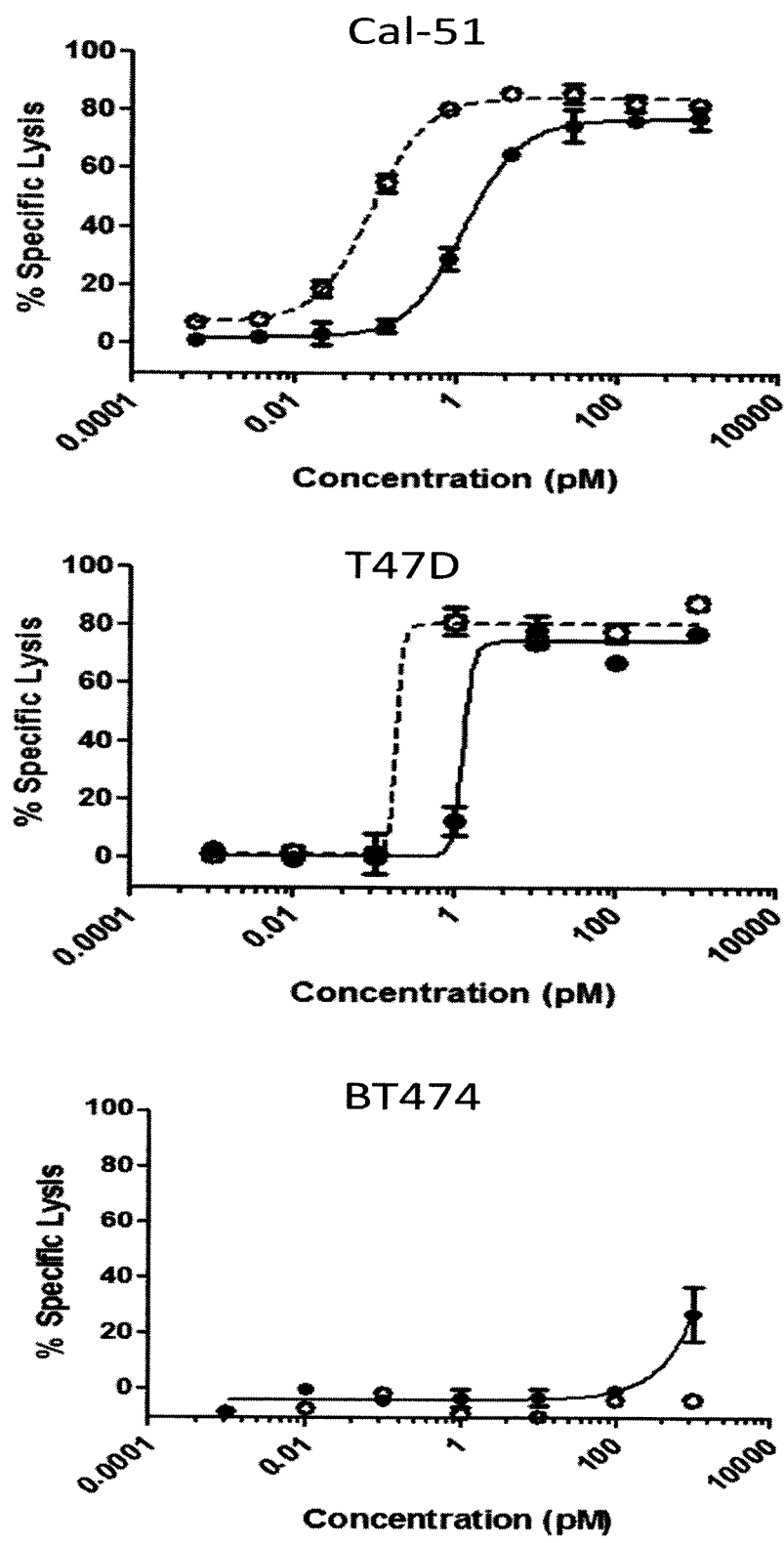
FIG. 9: Heterodimeric anti-FOLR1/CD3ε heterodimeric bispecific antibody (solidly filled circles and solid lines) or single chain anti-FOLR1/CD3ε molecule (open circles and dashed lines) induces lysis of FOLR1-expressing tumor cell lines. The x axis indicates the concentration of the heterodimeric anti-FOLR1/CD3ε bispecific antibody or anti-FOLR1/CD3ε single chain molecule (pM), and the y axis indicates the percent of tumor target cells lysed. Methods are described in Example 6. As indicated, data from the Cal-51, T47D, and BT474 cell lines are in the top, middle, and bottom panels, respectively.

Specific lysis of Cal-51 cells and T47D cells was observed with both anti-FOLR1/CD3ε heterodimeric bispecific antibody P136795.3 and the anti-FOLR1/CD3ε single chain bispecific molecule. FIG. 9. The $EC_{50}$ for P136795.3 was 1.208 pM and 1.26 pM in Cal-61 and T47D cells, respectively. The $EC_{50}$ for the anti-FOLR1/CD3ε single chain bispecific molecule was 0.087 pM and 0.19 pM in Cal-51 and T47D cells, respectively. There was minimal lysis of BT474, a cell line with undetectable levels of FOLR1 (FIG. 9), and this lysis was observed only at the highest P136795.3 concentration tested. Tumor target cells in the presence of the P136795.3, but absence of T cells, did not result in 7AAD uptake (data not shown). These observations suggest that both the anti-FOLR1/CD3ε heterodimeric bispecific antibody P136795.3 and the anti-FOLR1/CD3ε single chain bispecific molecule are highly specific and potent reagents capable of inducing tumor cell lysis by T cells.

Figure 10A:
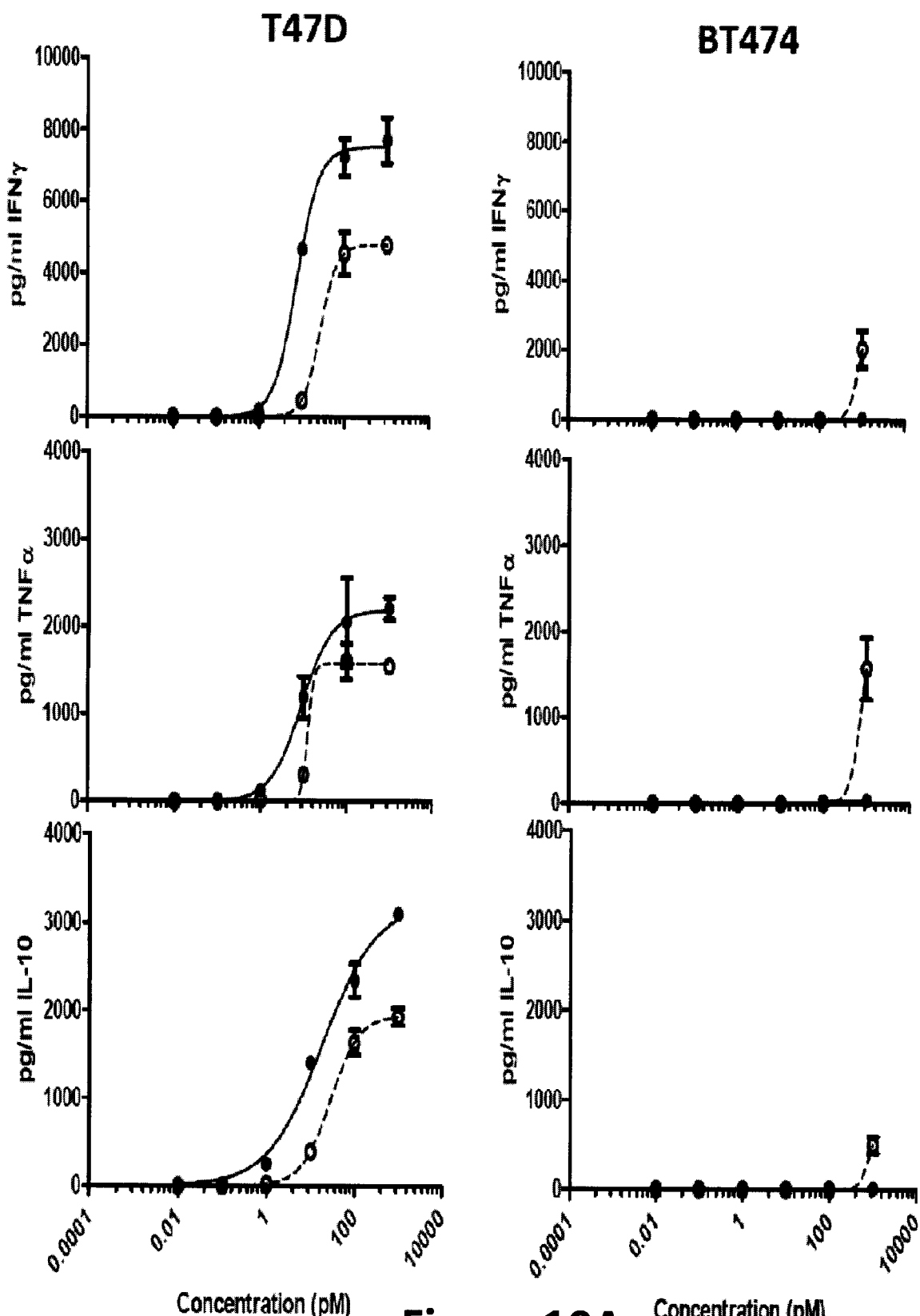
FIG. 10A shows data on interferon gamma (IFNγ, top), tumor necrosis factor alpha (TNFα, middle), and interleukin-10 (IL-10, bottom)
Figure 10B:
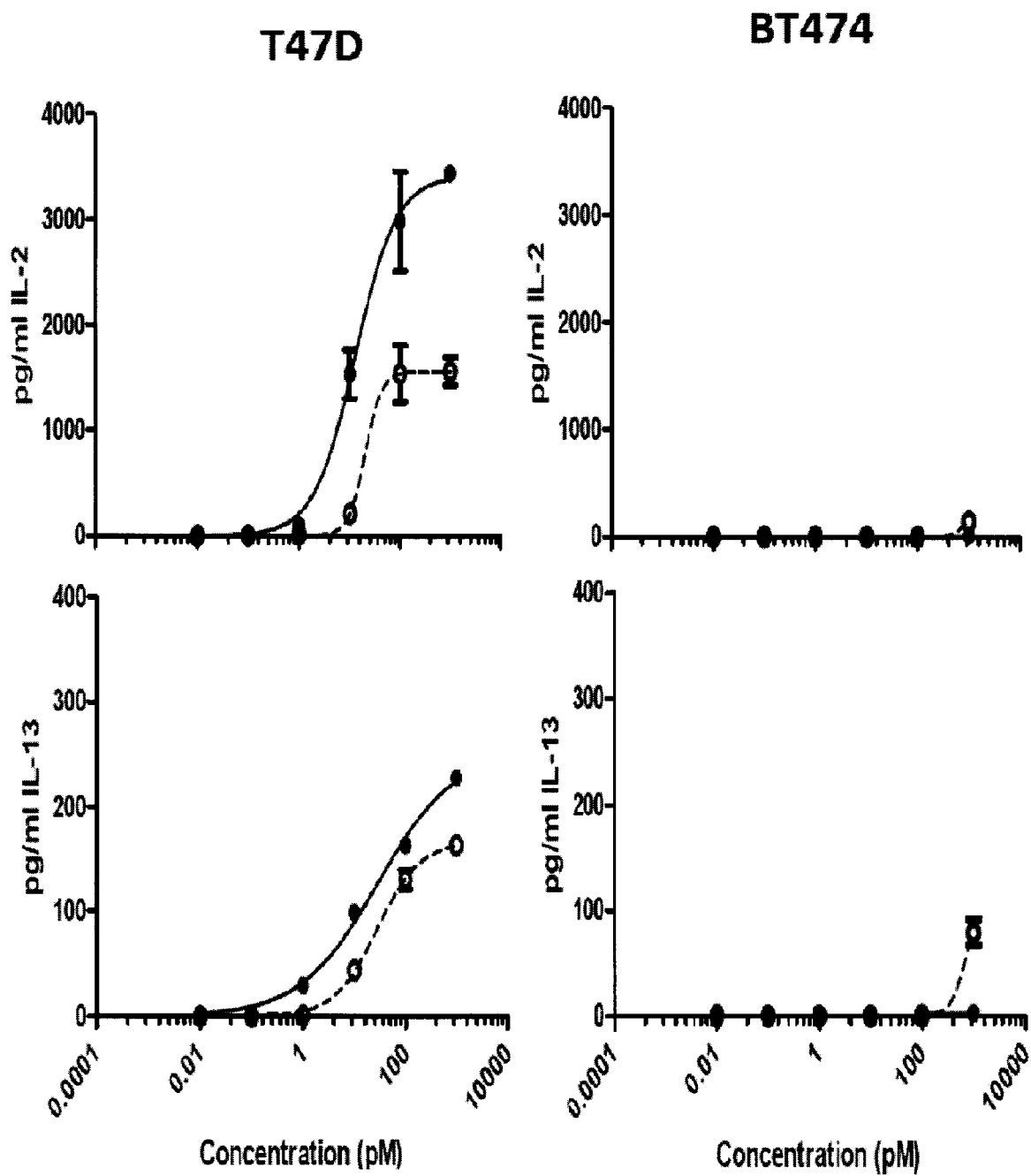
FIG. 10B shows data on interleukin-2 (IL-2, top) and interleukin-13 (IL-13, bottom).

The anti-FOLR1/CD3ε heterodimeric bispecific antibody P136795.3 was also tested to determine whether it could stimulate the release of various cytokines by T cells in the presence of a tumor cell line expressing FOLR1 (T47D) or in the presence of a cell line that does not express detectable FOLR1 (BT474). As a positive control, the single chain anti-FOLR1/CD3ε bispecific molecule was also tested in this assay. T cells were isolated as described above were incubated in culture medium for about 24 hours in the presence of either T47D cells or BT474 cells in the presence of various concentrations of P136795.3 or the single chain bispecific molecule. The results are shown in FIGS. 10A and 10B. In the presence of T47D cells, the highest cytokine concentrations were seen with IFN-γ, TNF-α, IL-10 and IL-2 (greater than 1000 pg/mL). Moderate levels of IL-13 were also observed. Cytokines were also observed in the presence of the FOLR1-negative cell line, BT474, but only at the highest tested concentration of the heterodimeric bispecific anti-FOLR1/CD3ε antibody P136795.3 (1000 pM). The $EC_{50}$'s for cytokine release in the presence of T47D cells are shown in Table 5 below.

TABLE 5

| $EC_{50}$'s for cytokine release | | |
|---|---|---|
| | $EC_{50}$ (pM) for heterodimeric anti-FOLR1/CD3ε in presence of T47D cells | $EC_{50}$ (pM) for single chain anti-FOLR1/CD3ε in presence of T47D cells |
| IFN-γ | 27.1 | 7.5 |
| TNF-α | 12.5 | 8.8 |
| IL-10 | 28.3 | 18.4 |
| IL-2 | 20.3 | 12.9 |
| IL-13 | 27.8 | 28.1 |

These results suggest that T cells respond to the presence of an anti-FOLR1/CD3ε heterodimeric bispecific antibody or single chain bispecific molecule by secreting cytokines only in the presence of target cells expressing FOLR1.

Example 7

HER2-Expressing Cancer Cell-Induced Cytokine Secretion by T Cells

Cell culture supernatants from the TDCC assays as described in Example 4 taken after 24 hours of incubation were assayed for production of various cytokines in the presence of tumor cells expressing HER2 on their cell surface (JIMT-1 cells) or a control cell that did not express the target cell protein (SHP77 cells). Cytokine production by T cells was measured in the presence of an anti-HER2/CD3ε heterodimeric bispecific antibody (P136797.3) or single chain bispecific molecule (having the amino acid sequence of SEQ ID NO:75) plus JIMT-1 cells or SHP77 cells. Production of interferon gamma (IFN-γ), tumor necrosis factor alpha (TNF-α), interleukin-10 (IL-10), interleukin-2 (IL-2), and interleukin-13 (IL-13) were measured using the Human TH1/TH2 (7-Plex) Ultra-Sensitive Kit (Catalog No. K15011C-4, Meso Scale Diagnostics, LLC., Rockville, Md.) and the Human Proinflammatory I (4-Plex) Ultra-Sensitive Kit (Catalog No. K15009C-4, Meso Scale Diagnostics, LLC., Rockville, Md.) according to the manufacturer's instructions. In the presence of HER2-expressing JIMT-1 cells, T cells treated with P136797.3 or the single chain bispecific molecule released cytokines. Table 6 below shows the $EC_K$, for the five cytokines assayed.

TABLE 6

Cytokine release by T cells in the presence
of JIMT-1 cells and anti- HER2/CDε bispecific

| | EC$_{50}$ JIMT-1 cells | |
|---|---|---|
| cytokine | heterodimeric anti-HER2/CD3ε | single chain anti-HER2/CD3ε |
| IFN-γ | 45.5 | 2.1 |
| TNF-α | 36.3 | 1.8 |
| IL-10 | 11.1 | 0.9 |
| IL-2 | 21.5 | 1.2 |
| IL-13 | 19.0 | 1.8 |

Figure 11A:
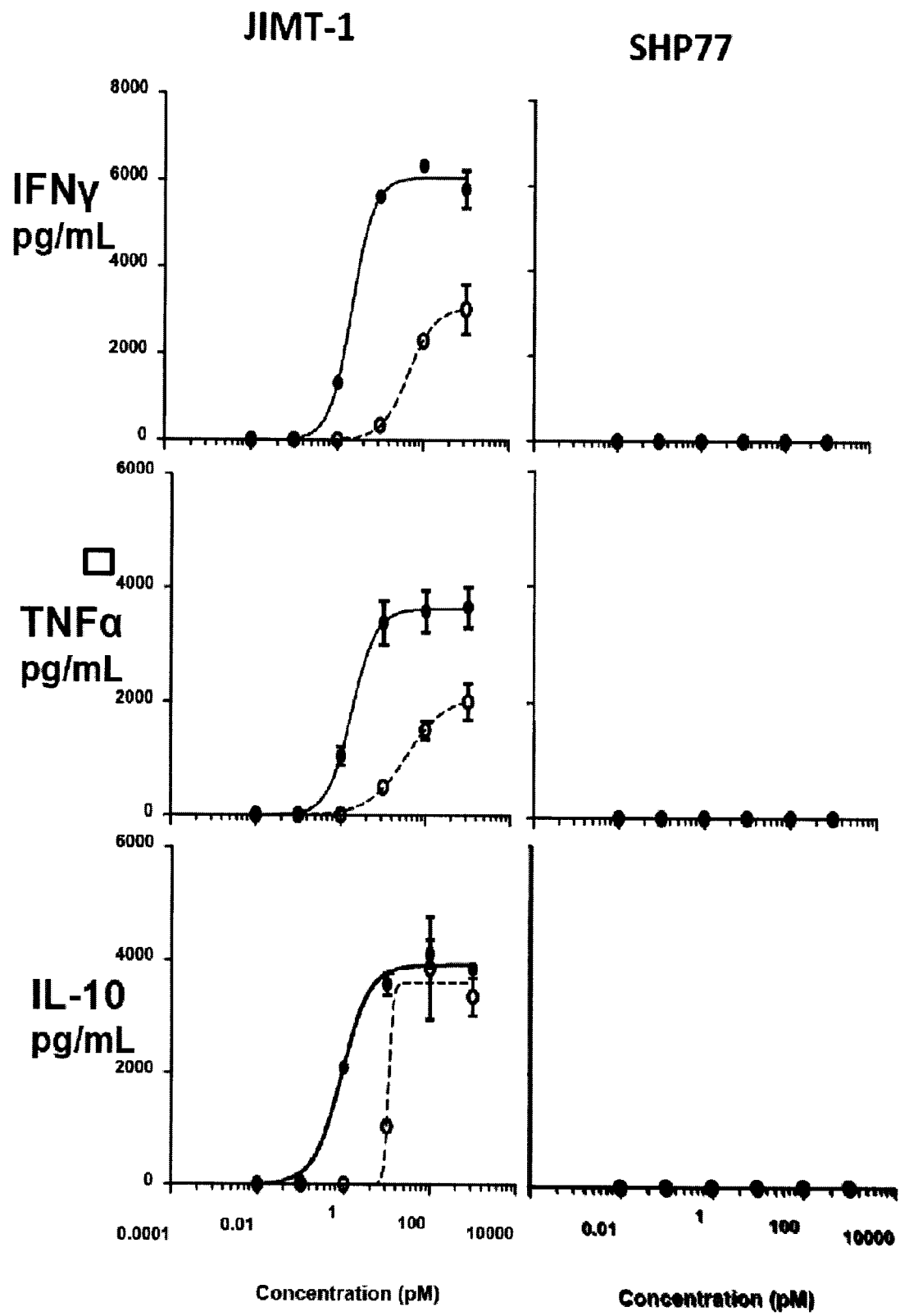
FIG. 11A shows data on IFNγ (top), TNFα (middle), and IL-10 (bottom)
Figure 11B:
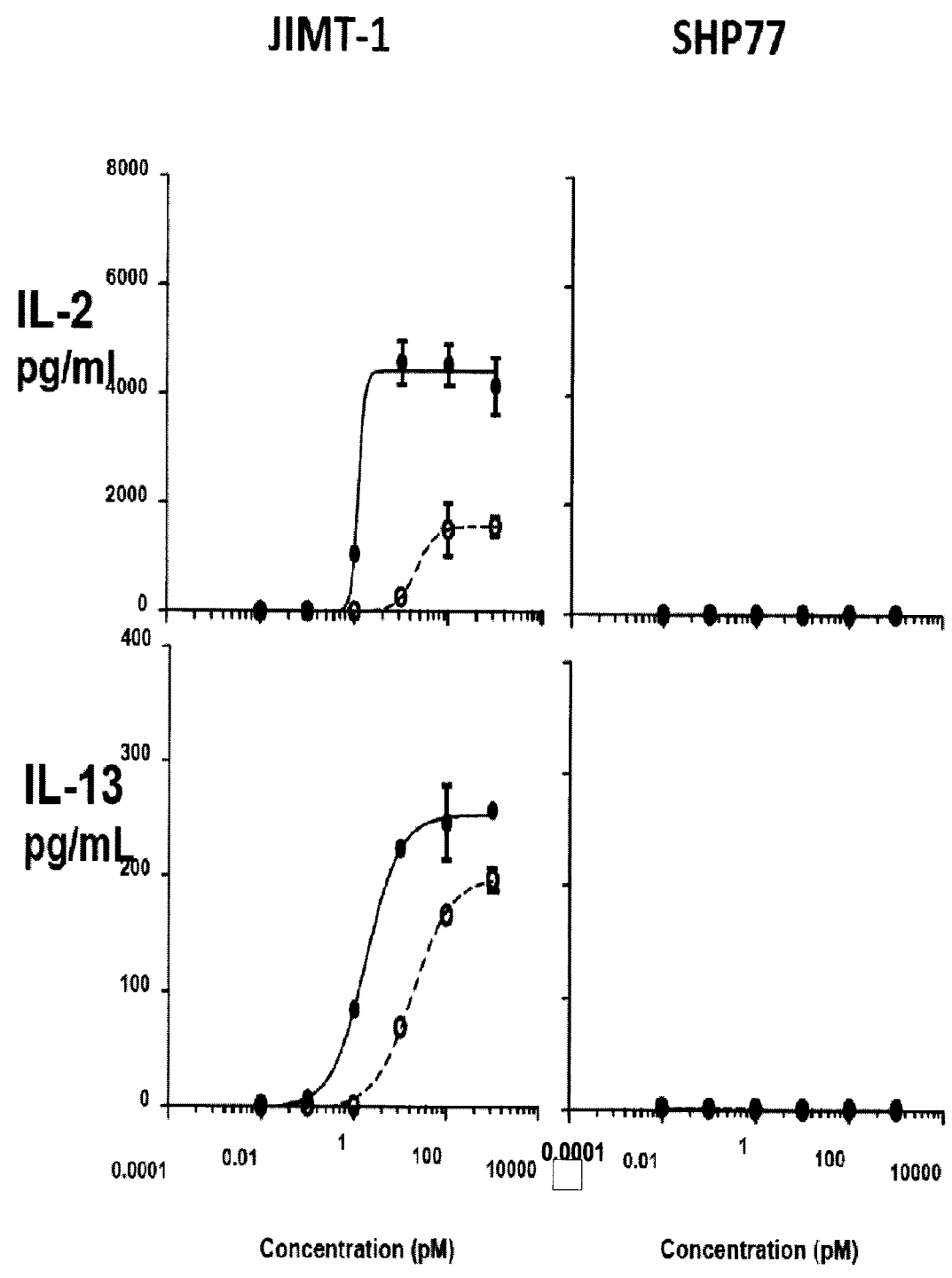
FIG. 11B shows data on IL-2 (top) and IL-13 (bottom).

FIGS. 11A and 11B show the titration curves for cytokine production by T cells in the presence of either HER2-expressing JIMT-1 cells or SHP77 cells (which do not express HER2) and varying concentration of P136797.3 or the single chain bispecific molecule. These data indicate that both the anti-HER2/CD3ε heterodimeric bispecific antibody and the anti-HER2/CD3ε single chain bispecific molecule can induce cytokine production in the presence of JIMT-1 cells, but not in the presence of SHP77 cells.

Figure 12:
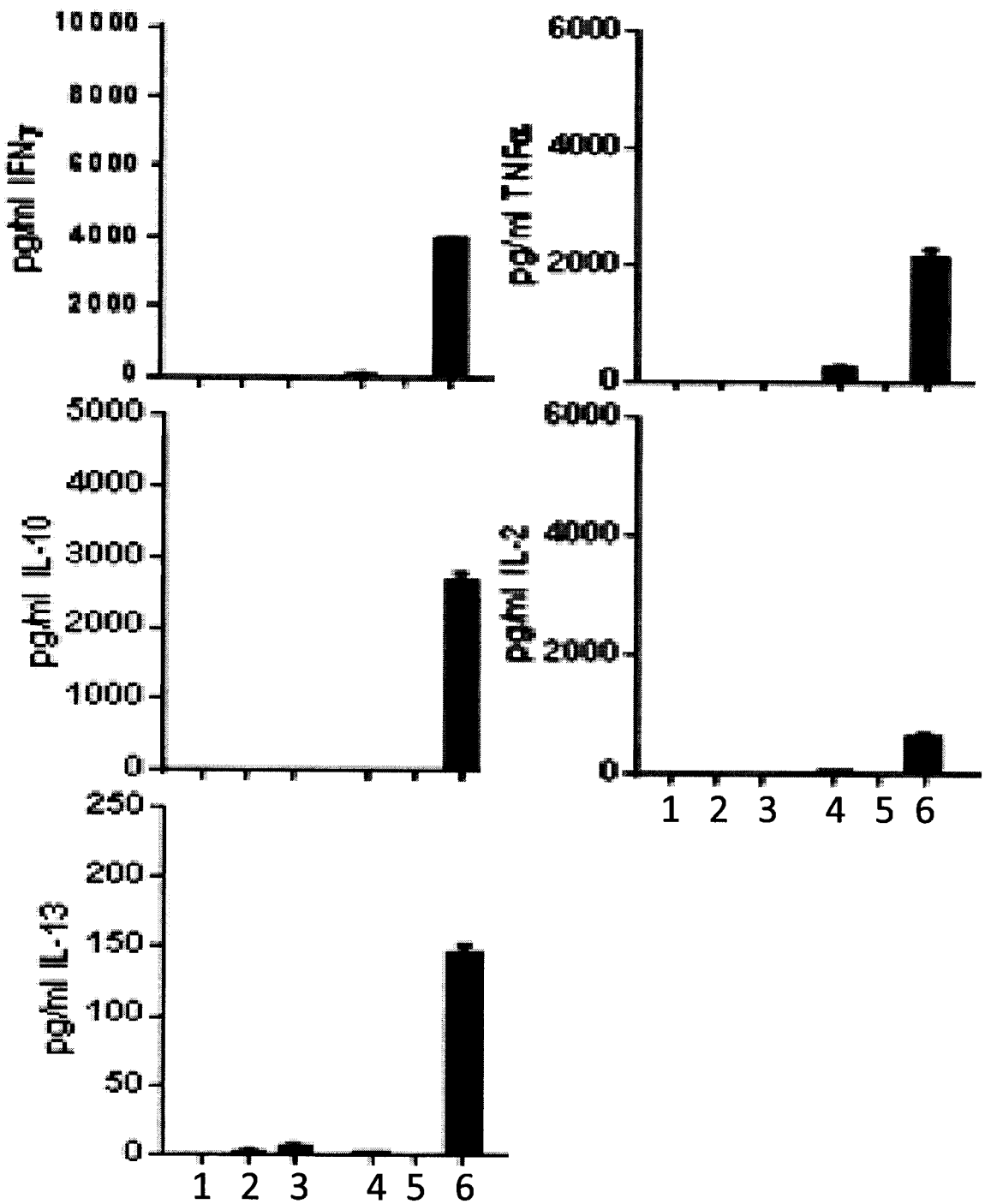
FIG. 12: Cytokine release requires both JIMT-1 cells and T cells plus the anti-HER2/CD3ε heterodimeric bispecific antibody. Methods are described in Example 7. The y axes indicate the levels of each cytokine detected. The cytokines assayed are indicated in each panel. As indicated on the x axes, samples contain (1) T cells alone without the bispecific, (2) JIMT-1 cells alone without the bispecific, (3) both T cells and JIMT-1 cells without the bispecific, (4) T cells alone with the bispecific, (5) JIMT-1 cells alone with the bispecific, and (6) both T cells and JIMT-1 cells with the bispecific.

To verify that the observed cytokine secretion was dependent on the presence of both cell types plus the bispecific, an additional experiment was done. Methods were as described above except that samples contained either (1) T cells alone, (2) JIMT-1 cells alone, or (3) both T cells and JIMT-1 cells in the presence or absence of the anti-HER2/CD3ε heterodimeric bispecific antibody. As shown in FIG. 12, the cytokines were secreted only in the presence of both cell types and the bispecific.

Example 8

In Vivo Activity of a Heterodimeric Bispecific Antibody

The experiment described below demonstrates the activity of a heterodimeric bispecific antibody in an in vivo cancer model system. Humanized mice were generated as follows. One to four days after birth, NOD.Cg-Prkdc$^{scid}$ Il2rg$^{tm1Wjl}$/SzJ mice (called NSG mice) were irradiated with a dose of 113 centi-Gray (cGY) using a gamma cell irradiator, and about 50,000 previously frozen human CD34$^+$ umbilical cord cells were injected into the liver. Starting at 5 weeks of age, animals received 3 weekly intraperitoneal injections of 9 μg of recombinant human IL-7 and 15 μg mouse anti-human IL-7 (a non-neutralizing half-life extending antibody). Blood levels of human T cells were analyzed for each mouse using flow cytometry at 11 weeks of age. Animals used in the study described below had human T cell levels ranging from 0.1% to 40% (relative to all live white blood cells). An additional group of non-humanized, age matched animals (called "control mice") was included as a control group in the study. These animals ("NSG control mice") were dosed with P56019.5 (an anti-MSLN/anti-CD3ε heterodimeric bispecific antibody) as described below.

For the tumor study, each mouse was implanted subcutaneously with about 10 million cells from a mesothelian-expressing human pancreatic tumor cell line, Capan-2. Treatments were administered intravenously starting nine days after the tumor cell implant. Animals received either (1) five daily injections starting at day 9 of 100 μg/mouse of P56019.5 (an anti-MSLN/anti-CD3ε heterodimeric bispecific antibody), a control bispecific antibody (anti-human EGFRviii/anti-human CD3ε), or Dulbecco's phosphate buffered saline (DPBS) or (2) two injections, spaced four days apart at 100 μg/mouse, of an anti-human MSLN IgG1 antibody having the same VH and VL regions present in P56019.5 starting at day 9. Tumor volumes were measured, and animals were euthanized when their tumor reached 2000 mm$^3$ or at the end of the study (Day 33). Analysis of the data after completion of the study showed a direct correlation between tumor regression and human T cell numbers, with an apparent minimum of 3% human T cells in the blood being required for activity. Therefore, animals with less than 3% were excluded from the final analysis for all humanized mouse groups resulting in a final animal number of 4 mice per treatment group.

Figure 13:
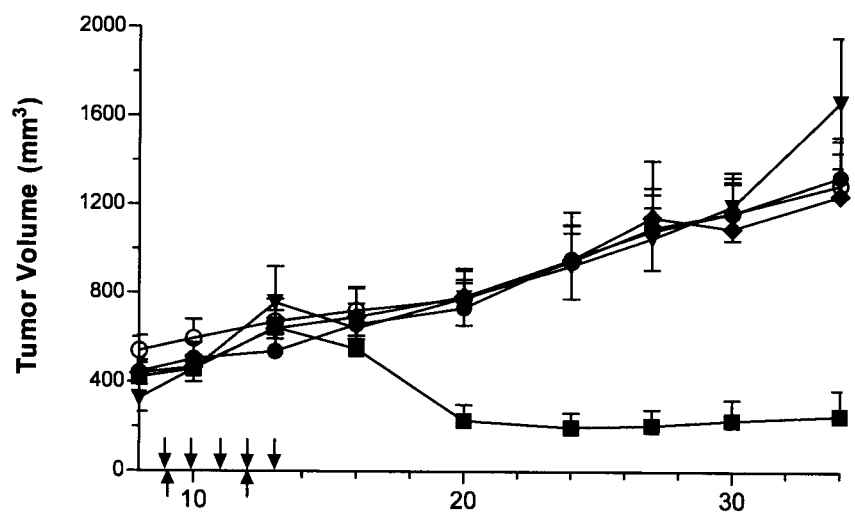
FIG. 13: In vivo inhibition of tumor growth by an anti-MSLN/CD3ε heterodimeric bispecific antibody. Methods are described in Example 8. The x axis shows the time (days) elapsed since tumor cells were implanted in the mice. The y axis shows the tumor volume (mm$^3$). Downward pointing arrows over the x axis indicate the times at which the anti-MSLN/CD3ε heterodimeric bispecific antibody, the control bispecific antibody, or Dulbecco's phosphate buffered saline (DPBS) was administered to the mice. Upward pointing arrows under the x axis indicate the times at which the anti-MSLN IgG1 antibody was administered. Symbols signify as follows: DPBS, open circles; P56019.5 (an anti-MSLN, anti-CD3ε heterodimeric bispecific antibody), solidly filled squares; control bispecific antibody (anti-human EGFRviii/anti-human CD3ε), solidly filled triangles; anti-human MSLN IgG1, solidly filled diamonds; and NSG control mice, solidly filled circles.

As shown in FIG. 13, implanted Capan-2 cells formed tumors in the "NSG control mice" (which were not humanized) despite treatment with P56019.5. Similarly, tumors formed in mice treated with the anti-human MSLN IgG1 antibody. The control anti-EGFRvIII/CD3ε bispecific antibody also could not inhibit the tumor growth. In contrast, tumor growth was significantly suppressed in the humanized mice that were treated with P56019.5 (the anti MSLN/CD3ε heterodimeric bispecific antibody). Thus, these data suggest that tumor growth inhibition was dependent on the presence of human T cells and the engagement of both tumor cells and T cells with a bispecific molecule. It further suggests that the T cell dependent suppression of tumor growth is mediated by the binding of mesothelin on Capan-2 cells. This study demonstrated that bispecific heterodimeric antibodies could induce T cell-mediated killing of target cells in vivo.

Example 9

Pharmacokinetic Properties of a Heterodimeric Bispecific Antibody

In the experiment described below, the single dose pharmacokinetic properties of a heterodimeric bispecific antibody were compared to those of a single chain bispecific molecule. The first and second polypeptide chains of an anti-HER2/CD3ε heterodimeric bispecific antibody (which was designated P136797.3) had the amino acid sequences of SEQ ID NO:20 and SEQ ID NO:21, respectively. The anti-HER2/CD3ε single chain bispecific antibody contained two VH/VL pairs joined by linker, and it had the amino acid sequence of SEQ ID NO:75.

The two test antibodies were injected at a concentration of 1 mg/kg either intravenously via the lateral tail vein in some NOD.SCID mice (obtained from Harlan Laboratories, Livermore, Calif.) or subcutaneously under the skin over the shoulders in others. Approximately 0.1 mL of whole blood was collected at each time point via retro-orbital sinus puncture. Upon clotting of whole blood, the samples were processed to obtain serum (0.040 mL per sample). Serum samples were analyzed by immunoassay using the technology Gyros AB (Warren, N.J.) to determine the serum concentrations of the single chain bispecific antibody and heterodimeric bispecific antibody. The assay employed anti-human Fc antibody to capture and detect the heterodimeric bispecific antibody (which contained an Fc region) and a CD3-mimicking peptide to capture the single chain heterodimeric molecule, which was detected with an anti-HIS antibody. Serum samples were collected at 0, 0.5, 2, 8, 24, 72, 120, 168, 240, 312, 384, and 480 hours after injection and maintained at −70° C. (±10° C.) prior to analysis. Pharmacokinetic parameters were estimated from serum concentrations by non-compartmental analysis using Phoenix® 6.3 software (Pharsight, Sunnyvale, Calif.).

Figure 14:
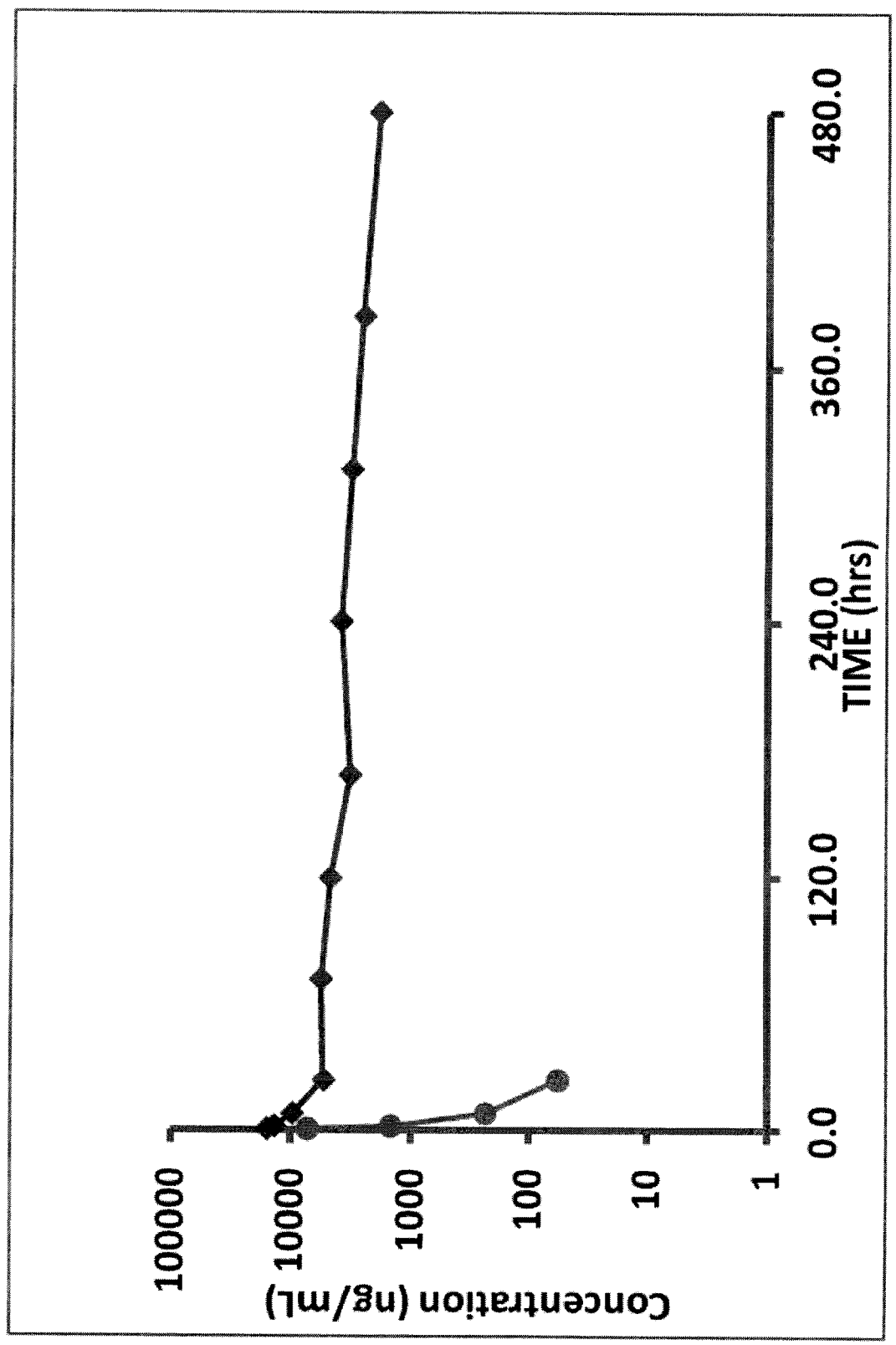
FIG. 14: Intravenous pharmacokinetic properties of a heterodimeric bispecific antibody and a single chain bispecific molecule. Methods are explained in Example 9. The x axis shows the time (hours) post injection of the antibodies, and the y axis shows the serum concentration of the antibodies (ng/mL). The filled circles connected by solid lines denote data from the injection of the single chain bispecific antibody. The filed diamonds connected by solid lines denote data from the injection of the heterodimeric bispecific antibody.
Figure 15:
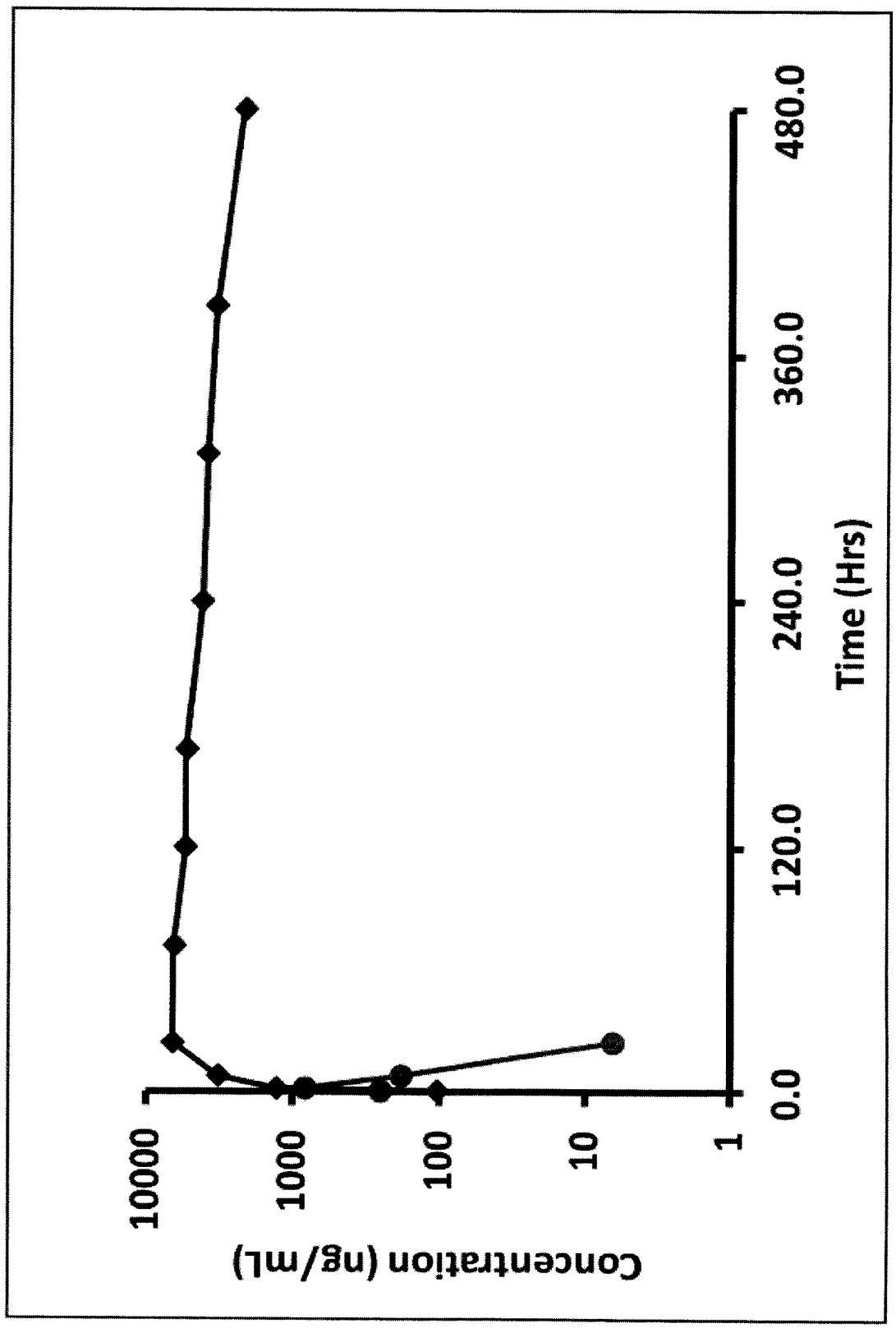
FIG. 15: Subcutaneous pharmacokinetic properties of a heterodimeric bispecific antibody. Methods are explained in Example 9. The x axis shows the time (hours) post injection of the antibodies, and the y axis shows the serum concentration of the antibodies (ng/mL). Symbols are as in FIG. 11.

The heterodimeric bispecific antibody showed extended serum half life (223 hours) compared to that of the single chain bispecific antibody (5 hours) when injected either subcutaneously or intravenously. FIGS. 14 and 15. Exposure to the single chain bispecific molecule was characterized by an area under the curve (AUC) of 19 hr*µg/mL, whereas the AUC of the heterodimeric bispecific antibody was 2541 hr*µg/mL. Thus, the heterodimeric bispecific antibody had favorable pharmacokinetic properties.

Example 10

In Vivo Inhibition of Tumor Growth by an Anti-FOLR1/CD3ε Heterodimeric Bispecific Antibody The experiment described below demonstrates the activity of a heterodimeric bispecific antibody in an in vivo cancer model system, using FOLR1-expressing NCI—N87, human gastric carcinoma cells. The anti-FOLR1/CD3ε heterodimeric bispecific antibody used in this experiment (PL-30056) has the general design illustrated in FIG. 1(4), and it comprises two polypeptide chains having the amino acid sequences of SEQ ID NOs:84 and 86. DNA constructs encoding these polypeptide chains were made essentially as described in Example 1, but could also be made synthetically. The amino acid sequence of the single chain anti-FOLR1/CD3ε single chain bispecific used in this experiment (PL-30055) is provided in SEQ ID NO:88.

Human pan-T cells were pre-activated and expanded in culture for use in this experiment by addition of anti-CD3/CD28/CD2 antibodies on days 0 and 14 of an 18-day culture period using a Miltenyi T cell activation/expansion kit according to the manufacturer's directions. To implant a human tumor in the mice, about $3 \times 10^6$ cells from a gastric carcinoma cell line that expresses FOLR1 (NCI—N87) in 50% MATRIGEL™ (BD Biosciences, catalog number 356237) were implanted subcutaneously into 8 week old female NSG mice (day 0). On day 10, $20 \times 10^6$ activated human pan-T cells were administered to each mouse by intraperitoneal (IP) injection. On days 11 and 18, an FcγR block consisting of 10 mg/mouse GAMMAGARD [Immune Globulin Infusion (Human)] 10% (Baxter) plus 0.2 mg/mouse anti-mu FcγRII/III (clone 2.4G2) was administered IP. One hour following the day 11 FcγR block animals (N=10/group) received either (1) daily IP injections of 0.05 mg/kg of a single chain anti-FOLR1/CD3ε bispecific molecule (having the amino acid sequence of SEQ ID NO:88) or (2) two IP injections, spaced 5 days apart of 1 mg/kg of an anti-FOLR1/CD3ε heterodimeric bispecific antibody (having the amino acid sequences of SEQ ID NOs:84 and 86) or 25 mM Lysine-hydrochloride, 0.002% Tween 80 in 0.9% NaCl, pH 7.0 (vehicle control). Tumor volumes were measured, and animals were euthanized when their tumor reached 2000 mm³ or at the end of the study (day 27).

Figure 16:
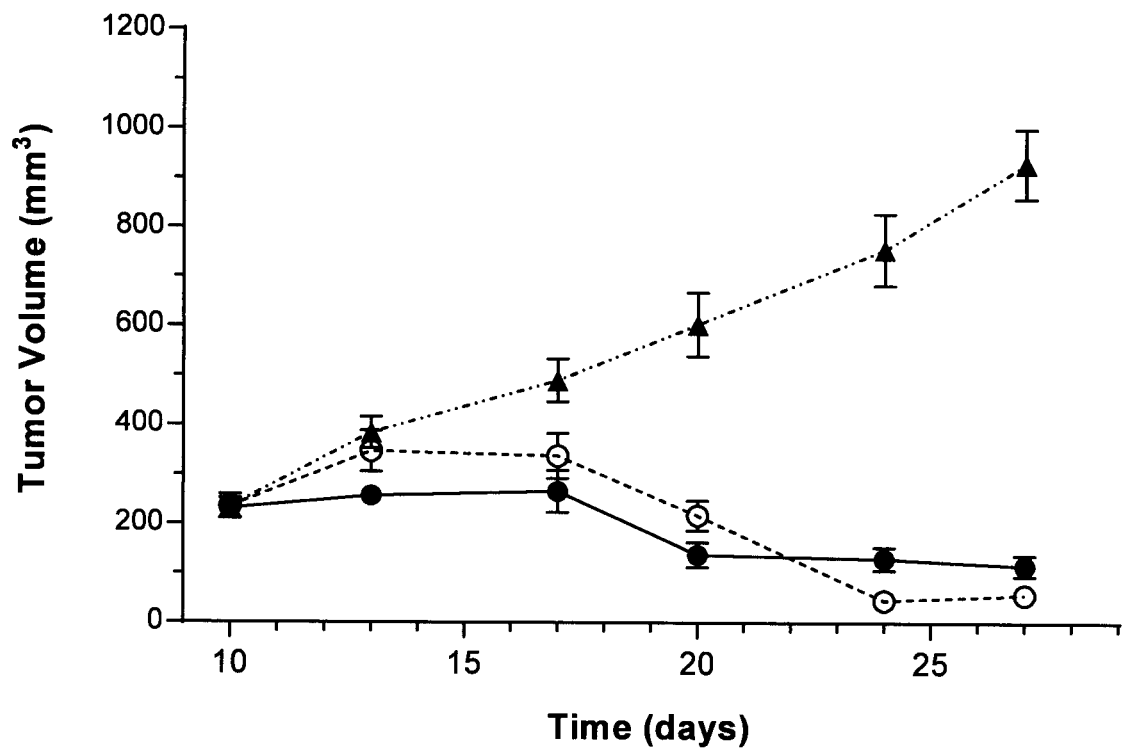
FIG. 16: In vivo inhibition of FOLR1-expressing tumor cells by an anti-FOLR1/CD3ε heterodimeric bispecific antibody. Methods are described in Example 10. The x axis shows the time (days) elapsed since the human tumor cells were implanted into the mice. The y axis shows tumor volume (mm³). Symbols signify as follows: Vehicle (25 mM Lysine-hydrochloride, 0.002% Tween 80 in 0.9% NaCl, pH 7.0), solidly filled triangle; anti-FOLR1/CD3ε single chain bispecific, solidly filled circles; and anti-FOLR1/CD3ε heterodimeric bispecific antibody, open circles.

As shown in FIG. 16, tumors grew in the vehicle-treated animals throughout the study. In contrast, tumor growth was significantly (p<0.0001) inhibited in the mice that were treated with the single chain anti-FOLR1/CD3ε bispecific molecule or the anti-FOLR1/CD3ε heterodimeric bispecific molecule as compared to the vehicle-treated mice. Throughout the experiment, there were no significant changes in body weight of treated or untreated mice (data not shown). These data suggest that the anti-FOLR1/CD3ε heterodimeric bispecific antibody can induce T cell-killing of target tumor cells in this in vivo system.

Example 11

In Vitro and In Vivo Activity of an Anti-CD33/CD3ε Heterodimeric Bispecific Antibody The experiment described below demonstrates the activity of a heterodimeric bispecific antibody in vitro and in an in vivo cancer model system, using the CD33-expressing leukemic cell line, Molm-13, or in a derivative thereof containing a luciferase gene, Molm-13-luciferase (Molm-13-luc). The amino acid sequences of the various single chain and heterodimeric bispecific antibodies used in this experiment are as follows: an anti-MEC/CD3ε single chain bispecific (P137424.7; used as a negative control) having the amino acid sequence of SEQ ID NO:90; an anti-CD33/CD3ε single chain bispecific (P138241.3) having the amino acid sequence of SEQ ID NO:92; and an anti-CD33/CD3ε heterodimeric bispecific antibody (PL-144537.6; which has the format illustrated in FIG. 1(6)) comprising the amino acid sequences of SEQ ID NO:94 and 96.

Figure 17:
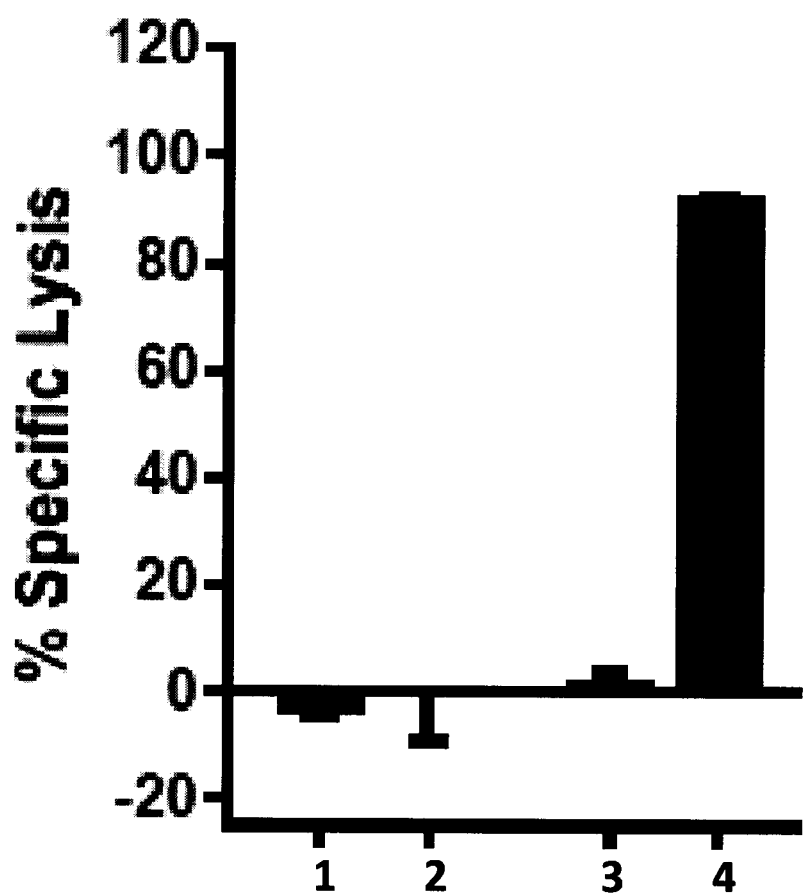
FIG. 17: Lysis of CD33-expressing tumor target cells in the presence of an anti-CD33/CD3ε heterodimeric bispecific antibody occurs in the presence, but not in the absence of T cells. Methods are described in Example 11. The y axis indicates the percent specific lysis of the Molm-13 cells. As indicated on the x axis, the various bars represent samples containing (1) Molm-13 cells only without the bispecific, (2) Molm-13 cell plus T cells without the bispecific, (3) Molm-13 cells only in the presence of the anti-CD33/CD3ε heterodimeric bispecific antibody, and (4) Molm-13 cells plus T cells in the presence of the anti-CD33/CD3ε heterodimeric bispecific antibody.

To determine whether the anti-CD33/CD3ε heterodimeric bispecific antibody could specifically lyse Molm-13 cells, a cytolysis assay was done as described in Example 2 using Molm-13 cells as target cells and pan T cells as effector cells. Samples contained either Molm-13 cells alone with or without the bispecific or both Molm-13 cells and pan T cells with or without the bispecific. As shown in FIG. 17, specific lysis was observed only in the sample containing both Molm-13 and pan T cells plus the bispecific. Thus, the bispecific can specifically lyse Molm-13 cells in the presence, but not in the absence, of effector T cells.

Molm-13-luc cells ($1 \times 10^6$), which luminesce in the presence of D-luciferin, were injected subcutaneously (SC) into the right flank of 10 week old female NSG mice (day 0). On the third day following tumor cell inoculation, $20 \times 10^6$ activated human pan-T cells (activated as explained in Example 10) were administered to each mouse by IP injection. On days 4 and 11, an FcγR block as described in Example 10 was administered by IP injection. One hour following the day 4 FcγR block, the mice (N=8/group) received one of the following treatments: (1) daily intraperitoneal injections of either 0.05 mg/kg of the anti-CD33/CD3ε single chain bispecific, 0.05 mg/kg of an anti-MEC/CD3ε single chain bispecific (SEQ ID NO:90; a negative control), or 25 mM lysine-hydrochloride, 0.002% Tween 80 in 0.9% NaCl, pH 7.0 (a vehicle control) for 10 days; or (2) two IP injections, spaced 5 days apart of 1 mg/kg anti-CD33/CD3ε heterodimeric bispecific antibody.

Bioluminescent imaging was performed on Monday, Wednesday, and Friday for two weeks after dosing began with an IVIS®-200 In Vivo Imaging System (Perkin Elmer). Nine minutes before imaging, mice were given 150 mg/kg D-luciferin by IP injection. Images were collected and analyzed using LIVING IMAGE® software 2.5 (Caliper Life Sciences). Naive animals (animals not inoculated with Molm-13-luc or human pan-T cells) were used as to measure baseline bioluminescence.

Figure 18:
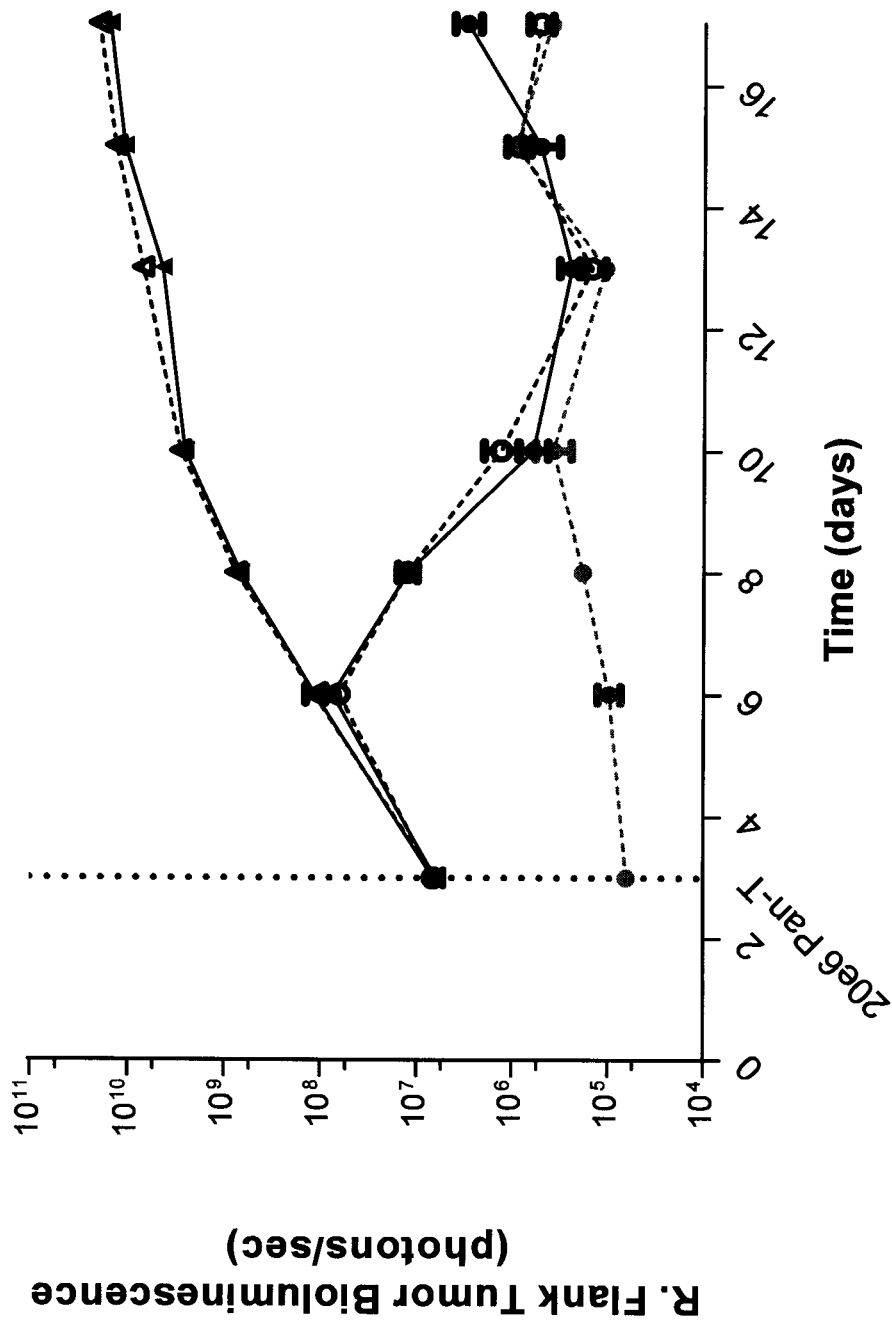
FIG. 18: In vivo inhibition of CD33-expressing Molm-13 tumor growth by anti-CD33/CD3ε heterodimeric bispecific antibody. Methods are described in Example 11. The x axis shows the time (days) elapsed since the tumor cells were implanted subcutaneously into the right flank of the mice. The y axis shows tumor bioluminescence. The vertical dotted line indicates the day on which human 20×10⁶ human T cells were administered to the mice. Symbols signify as follows: vehicle control (25 mM lysine-hydrochloride, 0.002% Tween 80 in 0.9% NaCl, pH 7.0), solidly filled triangles connected by solid lines; anti-MEC/CD3ε single chain bispecific, open triangles connected by dashed lines; anti-CD33/CD3ε single chain bispecific, solidly filled circles connected by solid lines; anti-CD33/CD3ε heterodimeric bispecific, open circles connected by dashed lines; and naïve animals, filled circles connected by dashed lines. The vertical dotted line indicates the day on which the mice received 20×10⁶ T cells by IP injection.

As shown in FIG. 18, in mice treated with vehicle or the negative control bispecific (anti-MEC/CD3ε single chain bispecific) and inoculated with Molm-13-luc cells followed by activated/expanded human Pan-T cells, the tumor burden increased throughout the course of the study. In contrast, tumor growth was significantly suppressed, as compared to tumor growth in mice that received the vehicle control, in the mice that were treated with the anti-CD33/CD3ε single chain bispecific (p<0.0001) or the anti-CD33/CD3ε heterodimeric bispecific antibody (p<0.0001). Throughout the experiment, there were no substantial changes in body weight of treated or untreated mice (data not shown). These data indicate that the anti-CD33/CD3ε heterodimeric bispecific antibody can induce killing of tumor target cells in vivo in this system.

Figure 19:
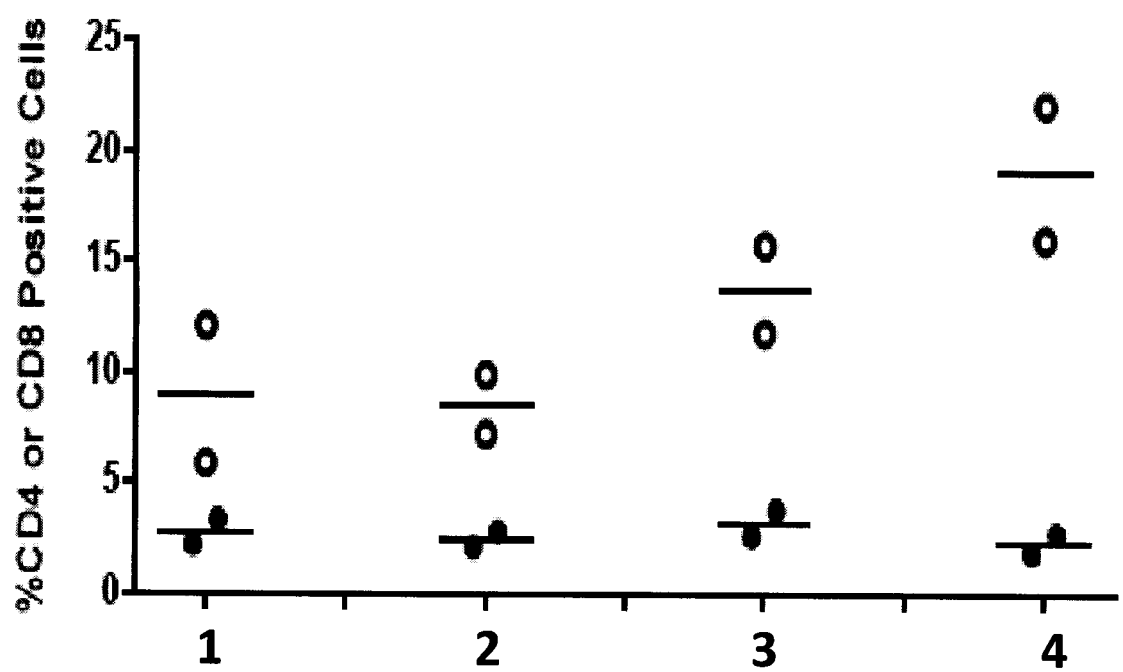
FIG. 19: In vivo expansion of CD8⁺ T cells by anti-CD33/CD3ε Fc-crossbody. Methods are described in Example 11. The x axis indicates the treatment received by the mice as follows: 1, vehicle (25 mM lysine-hydrochloride, 0.002% Tween 80 in 0.9% NaCl, pH 7.0); 2, anti-MEC/CD3ε single chain bispecific; 3, anti-CD33/CD3ε single chain bispecific; and 4, anti-CD33/CD3ε heterodimeric bispecific antibody. The y axis shows the percent human CD4⁺ (filled circles) or CD8⁺ (open circles) T cells relative to live white blood cells measured 24 hours after the final dose.

To determine if the heterodimeric bispecific antibody is capable of inducing human T cell proliferation in vivo, blood levels of human T cells were analyzed using flow cytometry 24 hours after the final dose of treatment, that is, on Day 11 for the single chain bispecifics and Day 14 for the heterodimeric bispecific antibody. Blood samples were stained with anti-human CD4 and anti-human CD8 to determine the percent of positive cells relative to live white blood cells (mouse and human). Results are shown in FIG. 19.

The levels of human CD4+ T cells remained constant across all treatments (vehicle, single chain bispecifics, and heterodimeric bispecific antibody), and the CD8+ T cells remained low in vehicle- and control single chain bispecific-treated animals. In contrast, the CD8+ T cells were expanded in animals treated with anti-CD33/CD3ε single chain or heterodimeric bispecific antibody, indicating that CD8+ T cells proliferate in vivo in response to the anti-CD33/CD3ε single chain bispecific or heterodimeric bispecific antibody.

Example 12

Dose Response of a Heterodimeric Bispecific Antibody in an In Vivo Cancer Model System Using CD33-Expressing Tumor Cells The experiment described below was designed to determine whether the extent of tumor inhibition by a heterodimeric bispecific antibody in an in vivo cancer model system was related to the dose of the antibody. The CD33-expressing cancer cell line, Molm-13-luc was used because it provides a luminescent signal upon addition of D-luciferin, thus facilitating quantitation of tumor growth in vivo.

The experiment was performed essentially as described in Example 11. As in Example 11, Molm-13-luc cells were injected on day 0, and activated human pan T cells were injected on day 3. As also explained in Example 11, an FcγR block was administered on days 4 and 11. One hour following the day 4 FcγR block, mice (N=8/group) received either two IP injections, spaced 5 days apart of 25 mM lysine-hydrochloride, 0.002% Tween 80 in 0.9% NaCl, pH 7.0 (vehicle control) or anti-CD33/CD3ε heterodimeric bispecific antibody at 1 mg/kg, 0.1 mg/kg, 0.03 mg/kg, 0.01 mg/kg, or 0.001 mg/kg. The anti-CD33/CD3 heterodimeric bispecific antibody was the same as that used in Example 11. Bioluminescent imaging was performed as described in Example 11.

Figure 20:
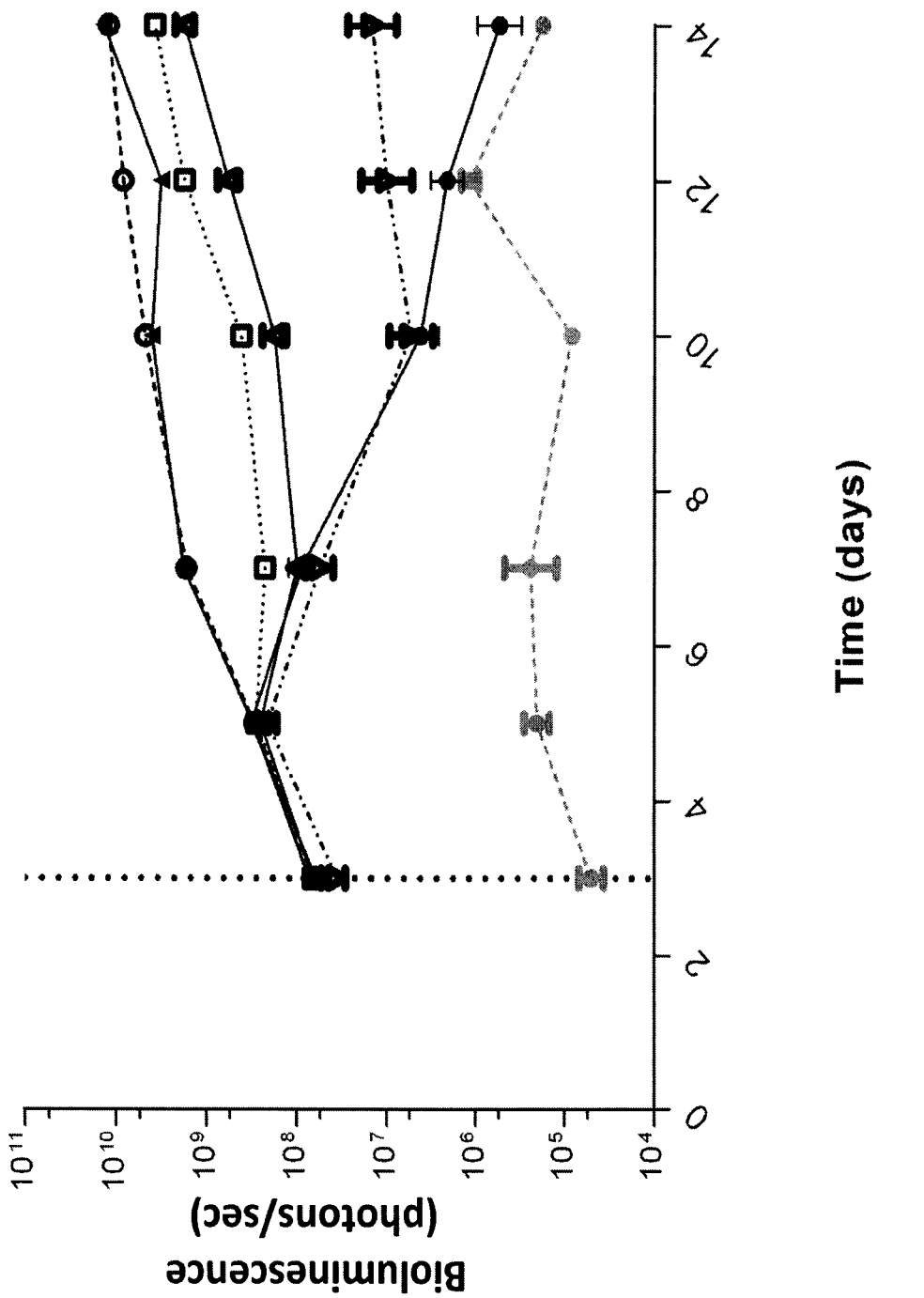
FIG. 20: In vivo dose response of tumor growth inhibition by anti-CD33/CD3ε heterodimeric bispecific antibody. Methods are described in Example 12. The x axis shows the time (days) elapsed since one million Molm-13-luc tumor cells were implanted subcutaneously into the right flank of each mouse. The y axis shows tumor bioluminescence. The vertical dotted line indicates the day on which human 20×10⁶ human T cells were administered to the mice. Symbols signify as follows: vehicle (25 mM lysine-hydrochloride, 0.002% Tween 80 in 0.9% NaCl, pH 7.0), open circles connected by dashed lines; 1 mg/kg anti-CD33/CD3ε heterodimeric bispecific antibody, filled circles connected by solid lines; 0.1 mg/kg anti-CD33/CD3ε heterodimeric bispecific antibody, open down-pointing triangles connected by dashed lines; 0.03 mg/kg anti-CD33/CD3ε heterodimeric bispecific antibody, open, up-pointing triangles connected by solid lines; 0.01 mg/kg anti-CD33/CD3ε heterodimeric bispecific antibody, open square connected by dashed lines; 0.001 mg/kg anti-CD33/CD3ε heterodimeric bispecific antibody, filled. Up-pointing triangles connected by solid lines; and naïve, filled circles connected by dashed lines.

As shown in FIG. 20, tumors grew throughout the study in vehicle-treated NSG mice (open circles connected by dashed lines). In contrast, a dose response of tumor growth supression was exhibited in mice treated with the anti-CD33/CD3ε heterodimeric bispecific antibody. Tumor growth inhibition as measured by bioluminescence was 99.99% with 1 mg/kg anti-CD33/CD3ε heterodimeric bispecific antibody (filled circles connected by solid lines), 99.88% with 0.1 mg/kg (open, down-pointing triangles connected by dashed lines), 85.5% with 0.03 mg/kg (open, up-pointing triangles connected by solid lines), 69.37% with 0.01 mg/kg (open squares connected by dashed lines), and ~11.88% with 0.001 mg/kg (filled, up-pointing triangles connected by solid lines). The $EC_{50}$ and $EC_{90}$ for anti-CD33/CD3ε heterodimeric bispecific antibody were 0.0012 mg/kg and 0.0463 mg/kg, respectively. Differences between the vehicle control and the heterodimeric bispecific antibody were significant for doses of 1 mg/kg, 0.1 mg/kg, 0.03 mg/kg, and 0.01 mg/kg (p<0.0001). Throughout the experiment, there were no significant changes in body weight of treated or untreated mice (data not shown). These data indicate that the anti-CD33/CD3ε heterodimeric bispecific antibody can potently induce killing of target cells in vivo in a dose dependent manner.

Example 13

Pharmacokinetics of an Anti-CD33/CD3ε Heterodimeric Bispecific Antibody in Cynomolgus Monkey The study was designed to evaluate the pharmacokinetic parameters of a single dose of an anti-CD33/CD3ε heterodimeric bispecific antibody comprising the amino acid sequences of SEQ ID NOs:94 and 96 at three different dose levels, 10, 100 and 200 µg/kg. Two animals per dose level were treated. The doses were administered by intravenous bolus injection. The serum pharmacokinetics were determined using an immunoassay from Meso Scale Discovery (Rockville, Md.) according to the manufacturer's instructions. Blood samples were taken at various time points, up to 168 hours post injection, and samples were processed to obtain serum. Pharmacokinetic parameters calculated from these results are shown in Table 7 below.

TABLE 7

Pharmacokinetic parameters of an anti-CD33/CD3ε heterodimeric bispecific antibody in cynomolgus monkey

| Dose (µg/kg) | Half life at beta phase ($T_{1/2\beta}$) (hour) | Area under the curve (AUC) (hr*pg/mL) | Total clearance (Cl) (mL/hr/kg) | Volume of distribution at steadystate ($V_{ss}$) (mL/kg) | Maximum drug concentration ($C_{max}$) (pg/mL) |
|---|---|---|---|---|---|
| 10 | 47.9 | 2,166,766 | 4.6 | 129 | 122,483 |
| 100 | 89.1 | 27,155,721 | 3.7 | 58 | 2,466,330 |
| 200* | 99.1 | 21,839,428 | 9.2 | 309 | 947,684 |

*PK parameters estimated from single animal.

As shown in Table 7, the half-lives determined at doses of 10, 100 and 200 µg/kg were, respectively, 47.9, 89.1 and 99.1 hours. Thus, the half-life was dose dependent. In general, the volume of distribution was low, as expected for an Fc-containing protein, ranging from 58-309 mL/kg. The clearance across doses ranged from 3.7 to 9.2 mL/hr/kg.

The 10 and 100 µg/kg doses appeared well tolerated with no clinical signs or symptoms upon dosing. By day 6 one animal from the 100 µg/kg dose had aspartate aminotransferase (AST) levels above baseline (which is an indication of tissue damage or disease) with no additional abnormal findings. One animal that received the 200 µg/kg dose did not tolerate the dose and expired by 12 hours after dosing.

Example 14

Cytolytic Synapse Formation in the Presence of the Anti-HER2/CD3ε Heterodimeric Bispecific Antibody An anti-HER2/CD3ε single chain bispecific having the amino acid sequence of SEQ ID NO:75 and an anti-HER2/CD3ε heterodimeric bispecific antibody comprising the amino acid sequences of SEQ ID NOs:20 and 21 were assayed to determine their ability to induce cytolytic synapse formation between T cells and JIMT-1 tumor cells that express HER2. JIMT-1 cells were distributed into 24-well poly-L-lysine-coated glass bottom culture plates ($0.5 \times 10^6$ cells/well in RPMI medium with 1% FCS and 2 g/L glucose). Following 1 hr incubation at 37° C., JIMT-1 cells adhering to the glass wells were gently washed with warm DPBS. Freshly isolated CD8$^+$ T cells ($1 \times 10^6$ from healthy donors), with or without the anti-HER2/CD3ε single chain or heterodimeric bispecific antibody at a concentration of 1 nM, were added to the JIMT-1 cells and allowed to incubate for an additional 20 minutes at 37° C. to generate cytolytic synapses.

Cells on the plate were washed with pre-warmed DPBS and immediately fixed with 3.7% parafomaldehyde for 10 minutes. The cells were then washed with DPBS and permeabilized with 0.1% TRITON™ X-100 for 5 minutes at room temperature. A mixture of primary antibodies (5 µg/ml anti-PKCθ and 0.4 µg/mL anti-CD45) were incubated with cells overnight at 4° C. and then washed 3 times. PCKθ is known to localize to immune synapses, while CD45 is expressed on the surface of T cells and is typically absent from the center of an immune synapse. A mixture of 8 µg/mL secondary antibodies (green (Alexa-Fluor-488) for anti-CD45 and red (Alexa-Fluor-647) for anti-PKCθ) were added for 3 hours at room temperature and then washed twice with DPBS. SlowFade® Gold anti-fade reagent with DAPI (nuclear stain) (Life Technologies #536939) was added directly to glass wells and plates stored at −70° C. protected from light.

Immunofluorescence confocal microscopy showed that CD45 was present on the surface of T cells (identified as the smaller cell type, with green CD45 staining), while PKCθ (red staining) gave a focused signal at the site of synapse formation between the JIMT-1 tumor cells (identified as the larger cell type) and T cells. Cytolytic synapses between the T cells and the JIMT-1 cells were observed in samples containing the anti-HER2/CD3ε single chain bispecific or the anti-HER2/CD3ε heterodimeric bispecific antibody, but not in samples that did not contain a bispecific (data not shown). These observations suggest that the observed cytolytic synapse formation was dependent on the presence of an anti-HER2/CD3ε bispecific and that both the single chain bispecific and the heterodimeric bispecific antibody can mediate immune synapse formation.

---

What is claimed is:

1. A heterodimeric bispecific antibody comprising
   (a) a first polypeptide chain comprising an amino acid sequence having the formula V1-L1-V2-L2-CH1, wherein V1 and V2 are immunoglobulin variable regions, L1 and L2 are linkers, L2 can be present or absent, and CH1 is a first immunoglobulin heavy chain constant region comprising SEQ ID NO: 70; and
   (b) a second polypeptide chain comprising an amino acid sequence having the formula V3-L3-V4-L4-CL, wherein V3 and V4 are immunoglobulin variable regions, L3 and L4 are linkers, L4 can be present or absent, and CL is an immunoglobulin light chain constant region comprising SEQ ID NO: 71 or 73;
   wherein either or both of the first polypeptide chain and the second polypeptide chain further comprise(s) an in vivo half life-extending moiety positioned C-terminally to the first polypeptide chain and/or the second polypeptide chain;
   wherein the half life-extending moiety is
   (i) an Fc polypeptide comprising any one of the amino acid sequences of SEQ ID NOS: 2-5 or a variant thereof containing no more than 10 amino acid substitutions, insertions, and/or deletions of a single amino acid per 100 amino acids;
   (ii) albumin or a fragment thereof;
   (iii) a fibronectin derivative comprising SEQ ID NO: 1, or a variant thereof containing no more than 10 amino acid substitutions, insertions, and/or deletions of a single amino acid per 100 amino acids, or a fragment thereof; or
   (iiii) polyethylene glycol (PEG);

wherein the heterodimeric bispecific antibody binds to a cancer antigen on a target cell and a cluster of differentiation 3 (CD3) epsilon protein on a T cell and mediates cytolysis of the target cell by the T cell in vivo;
   wherein V1, V2, V3, and V4 are selected from the group consisting of:
   (a) V1 and V2 are each heavy chain variable regions and V3 and V4 are each light chain variable regions, and V1 and V3 create a complete VH/VL antigen binding pair binding the cancer antigen on the target cell and V2 and V4 create a complete VH/VL antigen binding pair binding the CD3 epsilon protein on the T cell;
   (b) V1 and V2 are each light chain variable regions and V3 and V4 are each heavy chain variable regions, and V1 and V3 create a complete VH/VL antigen binding pair binding the CD3 epsilon protein on the T cell and V2 and V4 create a complete VH/VL antigen binding pair binding the cancer antigen on the target cell;
   (c) V1 and V3 are each heavy chain variable regions and V2 and V4 are each light chain variable regions, and V1 and V4 create a complete VH/VL antigen binding pair binding the cancer antigen on the target cell and V2 and V3 create a complete VH/VL antigen binding pair binding the CD3 epsilon protein on the T cell; and (d) V1 and V3 are each light chain variable regions and V2 and V4 are each heavy chain variable regions, and V1 and V4 create a complete VH/VL antigen binding pair binding the CD3 epsilon protein on the T cell and V2 and V3 create a complete VH/VL antigen binding pair binding the cancer antigen on the target cell; and wherein L1 and L3 are each no more than 10 amino acids long;

wherein when L2 and/or L4 are present, L2 and L4 are each no more than 10 amino acids long;

wherein the VH region binding the CD3 epsilon protein comprises the heavy chain CDR1, CDR2, and CDR3 sequences in SEQ ID NO: 42, 44, or 82; and wherein the VL region binding the CD3 epsilon protein comprises the light chain CDR1, CDR2, and CDR3 sequences in SEQ ID NO: 43, 45, or 83.

2. The heterodimeric bispecific antibody of claim 1, wherein L2 and L4 are absent.

3. The heterodimeric bispecific antibody of claim 1, wherein both the first polypeptide chain and the second polypeptide chain comprise the half life-extending moiety.

4. The heterodimeric bispecific antibody of claim 1, wherein the target cell is a cancer cell.

5. The heterodimeric bispecific antibody of claim 1, wherein the heterodimeric bispecific antibody can mediate increased expression of CD25 and CD69 on the T cell in the presence of the target cell, but not in the absence of the target cell.

6. The heterodimeric bispecific antibody of claim 3, wherein the Fc polypeptide of the first polypeptide and the second polypeptide chains is human IgG Fc polypeptide.

7. The heterodimeric bispecific antibody of claim 6, wherein the human IgG Fc polypeptide is human IgG1 Fc polypeptide, human IgG2 Fc polypeptide, or human IgG4 Fc polypeptide.

8. The heterodimeric bispecific antibody of claim 1, wherein the first polypeptide chain and the second polypeptide chain each comprise an Fc polypeptide, and wherein each Fc polypeptide comprises at least one charge pair substitution.

9. The heterodimeric bispecific antibody of claim 8, wherein (a) the Fc polypeptide of the first polypeptide chain comprises the charge pair substitutions E356K, E356R, D356R, or D356K and D399K or D399R, and the Fc polypeptide of the second polypeptide chain comprises the charge pair substitutions R409D, R409E, K409E, or K409D and N392D, N392E, K392E, or K392D; or (b) the Fc polypeptide of the second polypeptide chain-comprises the charge pair substitutions E356K, E356R, D356R, or D356K and D399K or D399R, and the Fc polypeptide of the first polypeptide chain comprises the charge pair substitutions R409D, R409E, K409E, or K409D and N392D, N392E, K392E, or K392D;

(c) the Fc polypeptide of the first and/or second polypeptide chains comprises one or more alteration(s) that inhibit(s) Fc gamma receptor (FcγR) binding;

(d) the Fc polypeptide of the first and/or second polypeptide chains comprises an alteration that extends half life; or (e) the Fc polypeptide of the first and/or second polypeptides comprises an alteration that enhances antibody-dependent cell-mediated cytotoxicity (ADCC).

10. The heterodimeric bispecific antibody of claim 9, wherein the one or more alteration(s) that inhibit(s) Fc gamma receptor (FcγR) binding comprise the alterations L234A, L235A, and/or any substitution at position 297.

11. The heterodimeric bispecific antibody of claim 9, wherein the Fc alteration that extends half life comprises an insertion between residues 384 and 385 according to the EU numbering system, and wherein the insertion comprises the amino acid sequence of any one of SEQ ID NOs: 54-65.

12. The heterodimeric bispecific antibody of claim 1, wherein V1, V2, V3, and V4 comprise the amino acid sequences of:

(a) SEQ ID NO:46 or 49, SEQ ID NO:43, SEQ ID NO:42, and SEQ ID NO:48, respectively;

(b) SEQ ID NO:43, SEQ ID NO:46 or 49, SEQ ID NO:48, and SEQ ID NO:42, respectively;

(c) SEQ ID NO:50, SEQ ID NO:46 or 49, SEQ ID NO:48, and SEQ ID NO:51, respectively; or (d) SEQ ID NO:44, SEQ ID NO:52, SEQ ID NO:53, and SEQ ID NO:45, respectively.

13. The heterodimeric bispecific antibody of claim 1, wherein the heterodimeric bispecific antibody comprises the amino acid sequence set forth in SEQ ID NO: 82 or 83.

14. The heterodimeric bispecific antibody of claim 1, wherein the fibronectin derivative comprises the amino acid sequence set forth in SEQ ID NO: 1.

15. The antibody of claim 1, wherein L1 and L3 are 5-10 amino acids long.

16. A composition comprising the heterodimeric bispecific antibody of claim 1 and a pharmaceutically acceptable carrier.

17. A nucleic acid encoding the first polypeptide chain or the second polypeptide chain of the heterodimeric bispecific antibody of claim 1.

18. A vector comprising the nucleic acid of claim 17.

19. A host cell containing the nucleic acid of claim 17.

20. A method of making a first polypeptide chain and a second polypeptide chain of a heterodimeric bispecific antibody comprising culturing the host cell of claim 19 under conditions to express the nucleic acid encoding the first polypeptide chain and the second polypeptide chain of the heterodimeric bispecific antibody, and recovering the first polypeptide chain or the second polypeptide chain of the antibody from the cell culture.

21. A heterodimeric bispecific antibody comprising (a) a first polypeptide chain comprising an amino acid sequence having the formula V1-L1-V2-L2-CH1, wherein V1 and V2 are immunoglobulin variable regions, L1 and L2 are linkers, L2 can be present or absent, and CH1 is a first immunoglobulin heavy chain constant region comprising SEQ ID NO: 70; and (b) a second polypeptide chain comprising an amino acid sequence having the formula V3-L3-V4-L4-CL, wherein V3 and V4 are immunoglobulin variable regions, L3 and L4 are linkers, L4 can be present or absent, and CL is an immunoglobulin light chain constant region comprising SEQ ID NO: 71 or 73;

wherein one of V1 and V4 is an immunoglobulin heavy chain variable (VH) region and the other is an immunoglobulin light chain variable (VL) region, and V1 and V4 can bind to a cancer antigen on a target cell or a cluster of differentiation 3 (CD3) epsilon protein on a T cell when they are part of an IgG and/or an scFv antibody;

wherein one of V2 and V3 is a VH region and the other is a VL region, and V2 and V3 can bind to the cancer antigen on the target cell or the CD3 epsilon protein on the T cell when they are part of an IgG and/or an scFv antibody;

wherein when V1 and V4 bind the cancer antigen V2 and V3 bind the CD3 epsilon protein, and when V1 and V4 bind the CD3 epsilon protein V2 and V3 bind the cancer antigen;

wherein either or both of the first polypeptide chain and the second polypeptide chain further comprise(s) an in vivo half life-extending moiety positioned C-terminally to the first polypeptide chain and/or the second polypeptide-chain;

wherein the half life-extending moiety is
  (i) an Fc polypeptide comprising any one of the amino acid sequences of SEQ ID NOS: 2-5 or a variant thereof containing no more than 10 amino acid substitutions, insertions, and/or deletions of a single amino acid per 100 amino acids;
  (ii) albumin or a fragment thereof;
  (iii) a fibronectin derivative comprising SEQ ID NO: 1, or a variant thereof containing no more than 10 amino acid substitutions, insertions, and/or deletions of a single amino acid per 100 amino acids, or a fragment thereof; or
  (iiii) polyethylene glycol (PEG);

wherein the heterodimeric bispecific antibody binds to the cancer antigen and the CD3 epsilon protein and mediates cytolysis of the target cell by the T cell in vivo;

wherein L1 and L3 are each no more than 10 amino acids long;

wherein when L2 and/or L4 are present, L2 and L4 are each no more than 10 amino acids long;

wherein the VH region binding the CD3 epsilon protein comprises the heavy chain CDR1, CDR2, and CDR3 sequences in SEQ ID NO: 42, 44, or 82; and wherein the VL region binding the CD3 epsilon protein comprises the light chain CDR1, CDR2, and CDR3 sequences in SEQ ID NO: 43, 45, or 83.

22. The antibody of claim 21, wherein L1 and L3 are 5-10 amino acids long.

23. A heterodimeric bispecific antibody comprising
  (a) a first polypeptide chain comprising an amino acid sequence having the formula V1-L1-V2-CH1, wherein V1 and V2 are immunoglobulin variable regions, L1 is a linker no more than 10 amino acids long, and CH1 is a first immunoglobulin heavy chain constant region comprising SEQ ID NO: 70; and
  (b) a second polypeptide chain comprising an amino acid sequence having the formula V3-L3-V4-CL, wherein V3 and V4 are immunoglobulin variable regions, L3 is a linker no more than 10 amino acids long, and CL is an immunoglobulin light chain constant region comprising SEQ ID NO: 71 or 73;

wherein either or both of the first polypeptide chain and the second polypeptide chain further comprise(s) an in vivo half life-extending moiety positioned C-terminally to the first polypeptide chain and/or the second polypeptide chain;

wherein the half life-extending moiety is
  (i) an Fc polypeptide comprising any one of the amino acid sequences of SEQ ID NOS: 2-5 or a variant thereof containing no more than 10 amino acid substitutions, insertions, and/or deletions of a single amino acid per 100 amino acids;
  (ii) albumin or a fragment thereof;
  (iii) a fibronectin derivative comprising SEQ ID NO: 1, or a variant thereof containing no more than 10 amino acid substitutions, insertions, and/or deletions of a single amino acid per 100 amino acids, or a fragment thereof; or
  (iiii) polyethylene glycol (PEG);

wherein the heterodimeric bispecific antibody binds to a cancer antigen on a target cell and a cluster of differentiation 3 (CD3) epsilon protein on a T cell and mediates cytolysis of the target cell by the T cell in vivo;

wherein V1, V2, V3, and V4 are selected from the group consisting of:
  (a) V1 and V2 are each heavy chain variable regions and V3 and V4 are each light chain variable regions, and V1 and V3 create a complete VH/VL antigen binding pair binding the cancer antigen on the target cell and V2 and V4 create a complete VH/VL antigen binding pair binding the CD3 epsilon protein on the T cell;
  (b) V1 and V2 are each light chain variable regions and V3 and V4 are each heavy chain variable regions, and V1 and V3 create a complete VH/VL antigen binding pair binding the CD3 epsilon protein on the T cell and V2 and V4 create a complete VH/VL antigen binding pair binding the cancer antigen on the target cell;
  (c) V1 and V3 are each heavy chain variable regions and V2 and V4 are each light chain variable regions, and V1 and V4 create a complete VH/VL antigen binding pair binding the cancer antigen on the target cell and V2 and V3 create a complete VH/VL antigen binding pair binding the CD3 epsilon protein on the T cell; and
  (d) V1 and V3 are each light chain variable regions and V2 and V4 are each heavy chain variable regions, and V1 and V4 create a complete VH/VL antigen binding pair binding the CD3 epsilon protein on the T cell and V2 and V3 create a complete VH/VL antigen binding pair binding the cancer antigen on the target cell; and wherein the VH region binding the CD3 epsilon protein comprises the heavy chain CDR1, CDR2, and CDR3 sequences in SEQ ID NO: 42, 44, or 82; and wherein the VL region binding the CD3 epsilon protein comprises the light chain CDR1, CDR2, and CDR3 sequences in SEQ ID NO: 43, 45, or 83.

24. The antibody of claim 23, wherein L1 and L3 are 5-10 amino acids long.

* * * * *

SEQUENCE LISTING

```
<160> NUMBER OF SEQ ID NOS: 97

<210> SEQ ID NO 1
<211> LENGTH: 91
<212> TYPE: PRT
<213> ORGANISM: Homo sapiens

<400> SEQUENCE: 1

Val Pro Arg Asp Leu Glu Val Val Ala Ala Thr Pro Thr Ser Leu Leu
1               5                   10                  15

Ile Ser Trp Asp Ala Pro His His Gly Val Ala Tyr Tyr Arg Ile Thr
                20                  25                  30

Tyr Gly Glu Thr Gly Gly Asn Ser Pro Val Gln Glu Phe Thr Val Pro
            35                  40                  45

Gly Ser Lys Ser Thr Ala Thr Ile Ser Gly Leu Lys Pro Gly Val Asp
        50                  55                  60

Tyr Thr Ile Asn Val Tyr Ala Val Leu Ala Tyr Pro Arg Gly Tyr Pro
65                  70                  75                  80

Leu Ser Lys Pro Ile Ser Ile Asn Tyr Arg Thr
                85                  90

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
```

```
                1               5                  10                 15
            Pro Glu Leu Leu Gly Gly Pro Ser Val Phe Leu Phe Pro Pro Lys Pro
                            20                  25                  30

Lys Asp Thr Leu Met Ile Ser Arg Thr Pro Glu Val Thr Cys Val Val
                            35                  40                  45

Val Asp Val Ser His Glu Asp Pro Glu Val Lys Phe Asn Trp Tyr Val
                50                  55                  60

Asp Gly Val Glu Val His Asn Ala Lys Thr Lys Pro Arg Glu Glu Gln
             65                  70                  75                  80

Tyr Asn Ser Thr Tyr Arg Val Val Ser Val Leu Thr Val Leu His Gln
                            85                  90                  95

Asp Trp Leu Asn Gly Lys Glu Tyr Lys Cys Lys Val Ser Asn Lys Ala
                            100                 105                 110

Leu Pro Ala Pro Ile Glu Lys Thr Ile Ser Lys Ala Lys Gly Gln Pro
                            115                 120                 125

Arg Glu Pro Gln Val Tyr Thr Leu Pro Pro Ser Arg Glu Glu Met Thr
                130                 135                 140

Lys Asn Gln Val Ser Leu Thr Cys Leu Val Lys Gly Phe Tyr Pro Ser
            145                 150                 155                 160

Asp Ile Ala Val Glu Trp Glu Ser Asn Gly Gln Pro Glu Asn Asn Tyr
                            165                 170                 175

Lys Thr Thr Pro Pro Val Leu Asp Ser Asp Gly Ser Phe Phe Leu Tyr
                            180                 185                 190

Ser Lys Leu Thr Val Asp Lys Ser Arg Trp Gln Gln Gly Asn Val Phe
                            195                 200                 205

Ser Cys Ser Val Met His Glu Ala Leu His Asn His Tyr Thr Gln Lys
                            210                 215                 220

Ser Leu Ser Leu Ser Pro Gly Lys
            225                 230

<210> SEQ ID NO 3
            <211> LENGTH: 228
            <212> TYPE: PRT
            <213> ORGANISM: Homo sapiens

<400> SEQUENCE: 3

Glu Arg Lys Cys Cys Val Glu Cys Pro Pro Cys Pro Ala Pro Pro Val
            1               5                   10                  15

Ala Gly Pro Ser Val Phe Leu Phe Pro Pro Lys Pro Lys Asp Thr Leu
                            20                  25                  30

Met Ile Ser Arg Thr Pro Glu Val Thr Cys Val Val Val Asp Val Ser
                            35                  40                  45

His Glu Asp Pro Glu Val Gln Phe Asn Trp Tyr Val Asp Gly Met Glu
                50                  55                  60

Val His Asn Ala Lys Thr Lys Pro Arg Glu Glu Gln Phe Asn Ser Thr
             65                  70                  75                  80

Phe Arg Val Val Ser Val Leu Thr Val Val His Gln Asp Trp Leu Asn
                            85                  90                  95

Gly Lys Glu Tyr Lys Cys Lys Val Ser Asn Lys Gly Leu Pro Ala Pro
                            100                 105                 110

Ile Glu Lys Thr Ile Ser Lys Thr Lys Gly Gln Pro Arg Glu Pro Gln
                            115                 120                 125

Val Tyr Thr Leu Pro Pro Ser Arg Glu Glu Met Thr Lys Asn Gln Val
                130                 135                 140
```

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 4
<211> LENGTH: 279
<212> TYPE: PRT
<213> ORGANISM: Homo sapiens

<400> SEQUENCE: 4

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
        50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
    195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
    275
```

```
<210> SEQ ID NO 5
<211> LENGTH: 229
<212> TYPE: PRT
<213> ORGANISM: Homo sapiens

<400> SEQUENCE: 5

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 6
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80
```

```
Ser Leu Lys Leu Ser Ser Val Thr Ala Ala Asp Thr Ala Val Tyr Tyr
            85                  90                  95

Cys Ala Arg Glu Asp Thr Met Thr Gly Leu Asp Val Trp Gly Gln Gly
            100                 105                 110

Thr Leu Val Thr Val Ser Ser Ala Ser Thr Lys Gly Pro Glu Val Gln
            115                 120                 125

Leu Val Glu Ser Gly Gly Gly Leu Val Lys Pro Gly Val Ser Leu Arg
            130                 135                 140

Leu Ser Cys Ala Ala Ser Gly Phe Thr Phe Ser Arg Tyr Ser Met Asn
145                 150                 155                 160

Trp Val Arg Gln Ala Pro Gly Lys Gly Leu Glu Trp Val Ser Ser Ile
                165                 170                 175

Ser Ser Ser Gly Thr Tyr Ile Lys Tyr Ala Asp Ser Val Lys Gly Arg
            180                 185                 190

Phe Thr Ile Ser Arg Asp Asn Ala Lys Asn Ser Leu Asn Leu Gln Met
            195                 200                 205

Asn Ser Leu Arg Ala Glu Asp Thr Ala Val Tyr Tyr Cys Ala Arg Asp
210                 215                 220

Arg Asp Arg Tyr Pro Leu Asp Tyr Trp Gly Gln Gly Thr Leu Val Thr
225                 230                 235                 240

Val Ser Ser Ala Ser Thr Lys Gly Pro Ser Val Phe Pro Leu Ala Pro
                245                 250                 255

Cys Ser Arg Ser Thr Ser Glu Ser Thr Ala Ala Leu Gly Cys Leu Val
                260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
290                 295                 300

Leu Tyr Ser Leu Ser Ser Val Val Thr Val Pro Ser Ser Asn Phe Gly
305                 310                 315                 320

Thr Gln Thr Tyr Thr Cys Asn Val Asp His Lys Pro Ser Asn Thr Lys
                325                 330                 335

Val Asp Lys Thr Val Gly Gly Gly Ser Ala Ala Ala Val Pro Arg
            340                 345                 350

Asp Leu Glu Val Val Ala Ala Thr Pro Thr Ser Leu Leu Ile Ser Trp
355                 360                 365

Asp Ala Pro His His Gly Val Ala Tyr Tyr Arg Ile Thr Tyr Gly Glu
            370                 375                 380

Thr Gly Gly Asn Ser Pro Val Gln Glu Phe Thr Val Pro Gly Ser Lys
385                 390                 395                 400

Ser Thr Ala Thr Ile Ser Gly Leu Lys Pro Gly Val Asp Tyr Thr Ile
                405                 410                 415

Asn Val Tyr Ala Val Leu Ala Tyr Pro Arg Gly Tyr Pro Leu Ser Lys
            420                 425                 430

Pro Ile Ser Ile Asn Tyr Arg Thr Asp Tyr Lys Asp Asp Asp Asp Lys
            435                 440                 445

Gly Ser Ser His His His His His His
    450                 455

<210> SEQ ID NO 7
<211> LENGTH: 327
<212> TYPE: PRT
<213> ORGANISM: Artificial Sequence
<220> FEATURE:
<223> OTHER INFORMATION: Synthetic polypeptide
```

-continued

```
<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Arg Thr Val Ala Ala Pro
            100                 105                 110

Ser Ser Tyr Glu Leu Thr Gln Pro Pro Ser Val Ser Val Ser Pro Gly
        115                 120                 125

Gln Thr Ala Arg Ile Thr Cys Ser Gly Asp Ala Leu Pro Lys Lys Tyr
    130                 135                 140

Ala Tyr Trp Tyr Gln Gln Lys Ser Gly Gln Ala Pro Val Leu Val Ile
145                 150                 155                 160

Tyr Glu Ala Thr Lys Arg Pro Ser Gly Ile Pro Glu Arg Phe Ser Gly
                165                 170                 175

Ser Ser Ser Gly Thr Met Ala Thr Leu Thr Leu Ser Gly Ala Gln Val
            180                 185                 190

Glu Asp Glu Ala Asp Tyr Tyr Cys Tyr Ser Thr Asp Ser Thr Asn Tyr
        195                 200                 205

His Trp Val Phe Gly Gly Thr Lys Leu Thr Val Leu Gly Gln Pro
    210                 215                 220

Lys Ala Ala Pro Ser Val Thr Leu Phe Pro Pro Ser Ser Glu Glu Leu
225                 230                 235                 240

Gln Ala Asn Lys Ala Thr Leu Val Cys Leu Ile Ser Asp Phe Tyr Pro
                245                 250                 255

Gly Ala Val Thr Val Ala Trp Lys Ala Asp Ser Ser Pro Val Lys Ala
            260                 265                 270

Gly Val Glu Thr Thr Thr Pro Ser Lys Gln Ser Asn Asn Lys Tyr Ala
        275                 280                 285

Ala Ser Ser Tyr Leu Ser Leu Thr Pro Glu Gln Trp Lys Ser His Arg
    290                 295                 300

Ser Tyr Ser Cys Gln Val Thr His Glu Gly Ser Thr Val Glu Lys Thr
305                 310                 315                 320

Val Ala Pro Thr Glu Cys Ser
                325

<210> SEQ ID NO 8
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 8

Asp Ile Lys Leu Gln Gln Ser Gly Ala Glu Leu Ala Arg Pro Gly Ala
1               5                   10                  15
```

```
Ser Val Lys Met Ser Cys Lys Thr Ser Gly Tyr Thr Phe Thr Arg Tyr
             20                  25                  30
Thr Met His Trp Val Lys Gln Arg Pro Gly Gln Gly Leu Glu Trp Ile
         35                  40                  45
Gly Tyr Ile Asn Pro Ser Arg Gly Tyr Thr Asn Tyr Asn Gln Lys Phe
     50                  55                  60
Lys Asp Lys Ala Thr Leu Thr Thr Asp Lys Ser Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Tyr Tyr Asp Asp His Tyr Ser Leu Asp Tyr Trp Gly Gln Gly
             100                 105                 110
Thr Thr Leu Thr Val Ser Ser Ala Ser Thr Lys Gly Pro Gln Val Gln
         115                 120                 125
Leu Gln Glu Ser Gly Pro Gly Leu Val Lys Pro Ser Glu Thr Leu Ser
     130                 135                 140
Leu Thr Cys Thr Val Ser Gly Gly Ser Ile Ile Ser His Tyr Trp Ser
145                 150                 155                 160
Trp Ile Arg Gln Pro Pro Gly Lys Gly Leu Glu Trp Ile Gly Tyr Ile
                 165                 170                 175
Tyr Tyr Ser Gly Ser Thr Asn Tyr Asn Pro Ser Leu Lys Ser Arg Val
             180                 185                 190
Thr Ile Ser Val Asp Thr Ser Lys Asn Gln Phe Ser Leu Lys Leu Thr
         195                 200                 205
Ser Val Thr Ala Ala Asp Thr Ala Val Tyr Tyr Cys Ala Arg Asp Gly
     210                 215                 220
Trp Ser Ala Phe Asp Tyr Trp Gly Gln Gly Thr Leu Val Thr Val Ser
225                 230                 235                 240
Ser Ala Ser Thr Lys Gly Pro Ser Val Phe Pro Leu Ala Pro Cys Ser
                 245                 250                 255
Arg Ser Thr Ser Glu Ser Thr Ala Ala Leu Gly Cys Leu Val Lys Asp
             260                 265                 270
Tyr Phe Pro Glu Pro Val Thr Val Ser Trp Asn Ser Gly Ala Leu Thr
         275                 280                 285
Ser Gly Val His Thr Phe Pro Ala Val Leu Gln Ser Ser Gly Leu Tyr
     290                 295                 300
Ser Leu Ser Ser Val Val Thr Val Pro Ser Ser Asn Phe Gly Thr Gln
305                 310                 315                 320
Thr Tyr Thr Cys Asn Val Asp His Lys Pro Ser Asn Thr Lys Val Asp
                 325                 330                 335
Lys Thr Val Gly Gly Gly Ser Ala Ala Ala Val Pro Arg Asp Leu
             340                 345                 350
Glu Val Val Ala Ala Thr Pro Thr Ser Leu Leu Ile Ser Trp Asp Ala
         355                 360                 365
Pro His His Gly Val Ala Tyr Tyr Arg Ile Thr Tyr Gly Glu Thr Gly
     370                 375                 380
Gly Asn Ser Pro Val Gln Glu Phe Thr Val Pro Gly Ser Lys Ser Thr
385                 390                 395                 400
Ala Thr Ile Ser Gly Leu Lys Pro Gly Val Asp Tyr Thr Ile Asn Val
                 405                 410                 415
Tyr Ala Val Leu Ala Tyr Pro Arg Gly Tyr Pro Leu Ser Lys Pro Ile
             420                 425                 430
Ser Ile Asn Tyr Arg Thr Asp Tyr Lys Asp Asp Asp Asp Lys Gly Ser
```

```
                435                 440                 445
Ser His His His His His
    450                 455

<210> SEQ ID NO 9
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 9

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Asp Ile Gln Met Thr Gln Ser Pro Ser Ser Leu Ser Ala Ser Val Gly
        115                 120                 125

Asp Arg Val Thr Ile Thr Cys Arg Ala Ser Gln Gly Ile Arg Asn Ala
    130                 135                 140

Leu Gly Trp Tyr Gln Gln Lys Pro Gly Lys Ala Pro Lys Arg Leu Ile
145                 150                 155                 160

Tyr Ala Ala Ser Ser Leu Gln Ser Gly Val Pro Ser Arg Phe Ser Gly
                165                 170                 175

Ser Gly Ser Gly Thr Glu Phe Thr Leu Thr Ile Ser Ser Leu Gln Pro
            180                 185                 190

Glu Asp Phe Ala Thr Tyr Tyr Cys Leu Gln His Asn Ser Tyr Pro Arg
        195                 200                 205

Thr Phe Gly Gln Gly Thr Lys Val Glu Ile Arg Arg Thr Val Ala Ala
    210                 215                 220

Pro Ser Val Phe Ile Phe Pro Pro Ser Asp Glu Gln Leu Lys Ser Gly
225                 230                 235                 240

Thr Ala Ser Val Val Cys Leu Leu Asn Asn Phe Tyr Pro Arg Glu Ala
                245                 250                 255

Lys Val Gln Trp Lys Val Asp Asn Ala Leu Gln Ser Gly Asn Ser Gln
            260                 265                 270

Glu Ser Val Thr Glu Gln Asp Ser Lys Asp Ser Thr Tyr Ser Leu Ser
        275                 280                 285

Ser Thr Leu Thr Leu Ser Lys Ala Asp Tyr Glu Lys His Lys Val Tyr
    290                 295                 300

Ala Cys Glu Val Thr His Gln Gly Leu Ser Ser Pro Val Thr Lys Ser
305                 310                 315                 320

Phe Asn Arg Gly Glu Cys
                325
```

```
<210> SEQ ID NO 10
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 10
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Val |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Arg | Tyr |
| | | | 20 | | | | | 25 | | | | | 30 | | |
| Gly | Met | Asn | Trp | Val | Arg | Gln | Ala | Pro | Gly | Lys | Gly | Leu | Glu | Trp | Val |
| | | 35 | | | | | 40 | | | | | 45 | | | |
| Ser | Ser | Ile | Ser | Ser | Ser | Gly | Thr | Tyr | Ile | Lys | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Ser | Leu | Asn |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Asp | Arg | Asp | Arg | Tyr | Pro | Leu | Asp | Tyr | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Gln | Val | Gln | Leu |
| | | 115 | | | | | 120 | | | | | 125 | | | |
| Gln | Glu | Ser | Gly | Pro | Gly | Leu | Val | Lys | Pro | Ser | Glu | Thr | Leu | Ser | Leu |
| | 130 | | | | | 135 | | | | | 140 | | | | |
| Thr | Cys | Thr | Val | Ser | Gly | Gly | Ser | Ile | Ile | Ser | His | Tyr | Trp | Ser | Trp |
| 145 | | | | | 150 | | | | | 155 | | | | | 160 |
| Ile | Arg | Gln | Pro | Pro | Gly | Lys | Gly | Leu | Glu | Trp | Ile | Gly | Tyr | Ile | Tyr |
| | | | | 165 | | | | | 170 | | | | | 175 | |
| Tyr | Ser | Gly | Ser | Thr | Asn | Tyr | Asn | Pro | Ser | Leu | Lys | Ser | Arg | Val | Thr |
| | | | 180 | | | | | 185 | | | | | 190 | | |
| Ile | Ser | Val | Asp | Thr | Ser | Lys | Asn | Gln | Phe | Ser | Leu | Lys | Leu | Thr | Ser |
| | | 195 | | | | | 200 | | | | | 205 | | | |
| Val | Thr | Ala | Ala | Asp | Thr | Ala | Val | Tyr | Tyr | Cys | Ala | Arg | Asp | Gly | Trp |
| | 210 | | | | | 215 | | | | | 220 | | | | |
| Ser | Ala | Phe | Asp | Tyr | Trp | Gly | Gln | Gly | Thr | Leu | Val | Thr | Val | Ser | Ser |
| 225 | | | | | 230 | | | | | 235 | | | | | 240 |
| Ala | Ser | Thr | Lys | Gly | Pro | Ser | Val | Phe | Pro | Leu | Ala | Pro | Cys | Ser | Arg |
| | | | | 245 | | | | | 250 | | | | | 255 | |
| Ser | Thr | Ser | Glu | Ser | Thr | Ala | Ala | Leu | Gly | Cys | Leu | Val | Lys | Asp | Tyr |
| | | | 260 | | | | | 265 | | | | | 270 | | |
| Phe | Pro | Glu | Pro | Val | Thr | Val | Ser | Trp | Asn | Ser | Gly | Ala | Leu | Thr | Ser |
| | | 275 | | | | | 280 | | | | | 285 | | | |
| Gly | Val | His | Thr | Phe | Pro | Ala | Val | Leu | Gln | Ser | Ser | Gly | Leu | Tyr | Ser |
| | 290 | | | | | 295 | | | | | 300 | | | | |
| Leu | Ser | Ser | Val | Val | Thr | Val | Pro | Ser | Ser | Asn | Phe | Gly | Thr | Gln | Thr |
| 305 | | | | | 310 | | | | | 315 | | | | | 320 |
| Tyr | Thr | Cys | Asn | Val | Asp | His | Lys | Pro | Ser | Asn | Thr | Lys | Val | Asp | Lys |
| | | | | 325 | | | | | 330 | | | | | 335 | |
| Thr | Val | Gly | Gly | Gly | Ser | Ala | Ala | Ala | Val | Pro | Arg | Asp | Leu | Glu |
| | | | 340 | | | | | 345 | | | | | 350 | | |
| Val | Val | Ala | Ala | Thr | Pro | Thr | Ser | Leu | Leu | Ile | Ser | Trp | Asp | Ala | Ile |
| | | 355 | | | | | 360 | | | | | 365 | | | |
| Gly | Leu | Tyr | Pro | Tyr | Tyr | Tyr | Arg | Ile | Thr | Tyr | Gly | Glu | Thr | Gly | Gly |

```
                    370                 375                 380
Asn Ser Pro Val Gln Glu Phe Thr Val Pro Gly Ser Lys Ser Thr Ala
385                 390                 395                 400

Thr Ile Ser Gly Leu Lys Pro Gly Val Asp Tyr Thr Ile Thr Val Tyr
                405                 410                 415

Ala Val Ser Gly Ile Phe Gly Trp Asn Ser Lys Pro Ile Ser Ile
                420                 425                 430

Asn Tyr Arg Thr Gly Ser Ser Asp Tyr Lys Asp Asp Asp Lys Gly
                435                 440                 445

Ser Ser His His His His His His
    450                 455

<210> SEQ ID NO 11
<211> LENGTH: 328
<212> TYPE: PRT
<213> ORGANISM: Artificial Sequence
<220> FEATURE:
<223> OTHER INFORMATION: Synthetic polypeptide

<400> SEQUENCE: 11

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Ala Thr Lys Arg Pro Ser Gly Ile Pro Glu Arg Phe Ser Gly Ser
50                  55                  60

Ser Ser Gly Thr Met Ala Thr Leu Thr Leu Ser Gly Ala Gln Val Glu
65                  70                  75                  80

Asp Glu Ala Asp Tyr Tyr Cys Tyr Ser Thr Asp Ser Thr Asn Tyr His
                85                  90                  95

Trp Val Phe Gly Gly Gly Thr Lys Leu Thr Val Leu Gly Thr Val Ala
            100                 105                 110

Ala Pro Asp Ile Gln Met Thr Gln Ser Pro Ser Ser Leu Ser Ala Ser
        115                 120                 125

Val Gly Asp Arg Val Thr Ile Thr Cys Arg Ala Ser Gln Gly Ile Arg
130                 135                 140

Asn Ala Leu Gly Trp Tyr Gln Gln Lys Pro Gly Lys Ala Pro Lys Arg
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Glu Phe Thr Leu Thr Ile Ser Ser Leu
            180                 185                 190

Gln Pro Glu Asp Phe Ala Thr Tyr Tyr Cys Leu Gln His Asn Ser Tyr
        195                 200                 205

Pro Arg Thr Phe Gly Gln Gly Thr Lys Val Glu Ile Arg Arg Thr Val
210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
            260                 265                 270

Ser Gln Glu Ser Val Thr Glu Gln Asp Ser Lys Asp Ser Thr Tyr Ser
```

```
                        275                 280                 285
Leu Ser Ser Thr Leu Thr Leu Ser Lys Ala Asp Tyr Glu Lys His Lys
            290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325
```

<210> SEQ ID NO 12
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 12

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Leu Val Thr Val Ser Ser Gly Gly Gly Ser Gly Gly Gly Gly Ser
        115                 120                 125

Ser Ser Ser Tyr Glu Leu Thr Gln Pro Pro Ser Val Ser Val Ser Pro
    130                 135                 140

Gly Gln Thr Ala Arg Ile Thr Cys Ser Gly Asp Ala Leu Pro Lys Lys
145                 150                 155                 160

Tyr Ala Tyr Trp Tyr Gln Gln Lys Ser Gly Gln Ala Pro Val Leu Val
                165                 170                 175

Ile Tyr Glu Ala Thr Lys Arg Pro Ser Gly Ile Pro Glu Arg Phe Ser
            180                 185                 190

Gly Ser Ser Ser Gly Thr Met Ala Thr Leu Thr Leu Ser Gly Ala Gln
        195                 200                 205

Val Glu Asp Glu Ala Asp Tyr Tyr Cys Tyr Ser Thr Asp Ser Thr Asn
    210                 215                 220

Tyr His Trp Val Phe Gly Gly Gly Thr Lys Leu Thr Val Leu Gly Ala
225                 230                 235                 240

Ser Thr Lys Gly Pro Ser Val Phe Pro Leu Ala Pro Cys Ser Arg Ser
                245                 250                 255

Thr Ser Glu Ser Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
        275                 280                 285

Val His Thr Phe Pro Ala Val Leu Gln Ser Ser Gly Leu Tyr Ser Leu
    290                 295                 300

Ser Ser Val Val Thr Val Pro Ser Ser Asn Phe Gly Thr Gln Thr Tyr
```

```
305                 310                 315                 320
Thr Cys Asn Val Asp His Lys Pro Ser Asn Thr Lys Val Asp Lys Thr
                325                 330                 335

Val Gly Gly Gly Ser Ala Ala Val Pro Arg Asp Leu Glu Val
            340                 345                 350

Val Ala Ala Thr Pro Thr Ser Leu Leu Ile Ser Trp Asp Ala Pro His
            355                 360                 365

His Gly Val Ala Tyr Tyr Arg Ile Thr Tyr Gly Glu Thr Gly Gly Asn
    370                 375                 380

Ser Pro Val Gln Glu Phe Thr Val Pro Gly Ser Lys Ser Thr Ala Thr
385                 390                 395                 400

Ile Ser Gly Leu Lys Pro Gly Val Asp Tyr Thr Ile Asn Val Tyr Ala
                405                 410                 415

Val Leu Ala Tyr Pro Arg Gly Tyr Pro Leu Ser Lys Pro Ile Ser Ile
            420                 425                 430

Asn Tyr Arg Thr Asp Tyr Lys Asp Asp Asp Lys Gly Ser Ser His
            435                 440                 445

His His His His His
    450

<210> SEQ ID NO 13
<211> LENGTH: 341
<212> TYPE: PRT
<213> ORGANISM: Artificial Sequence
<220> FEATURE:
<223> OTHER INFORMATION: Synthetic polypeptide

<400> SEQUENCE: 13

Glu Val Gln Leu Val Glu Ser Gly Gly Gly Leu Val Lys Pro Gly Val
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Gly Thr Tyr Ile Lys Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Ala Arg Asp Arg Asp Arg Tyr Pro Leu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Ser Ile Asn Asn Tyr
145                 150                 155                 160

Leu Asn Trp Tyr Gln Gln Lys Pro Gly Lys Ala Pro Thr Leu Leu Ile
                165                 170                 175

Tyr Ala Ala Ser Ser Leu Gln Ser Gly Val Pro Ser Arg Phe Ser Gly
            180                 185                 190

Ser Arg Ser Gly Thr Asp Phe Thr Leu Thr Ile Ser Ser Leu Gln Pro
        195                 200                 205

Glu Asp Phe Ala Ala Tyr Phe Cys Gln Gln Thr Tyr Ser Asn Pro Thr
```

```
                    210                 215                 220
Phe Gly Gln Gly Thr Lys Val Glu Val Lys Arg Thr Val Ala Ala Pro
225                 230                 235                 240

Ser Val Phe Ile Phe Pro Pro Ser Asp Glu Gln Leu Lys Ser Gly Thr
            245                 250                 255

Ala Ser Val Val Cys Leu Leu Asn Asn Phe Tyr Pro Arg Glu Ala Lys
                260                 265                 270

Val Gln Trp Lys Val Asp Asn Ala Leu Gln Ser Gly Asn Ser Gln Glu
            275                 280                 285

Ser Val Thr Glu Gln Asp Ser Lys Asp Ser Thr Tyr Ser Leu Ser Ser
290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340

<210> SEQ ID NO 14
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 14

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Ala Thr Lys Arg Pro Ser Gly Ile Pro Glu Arg Phe Ser Gly Ser
    50                  55                  60

Ser Ser Gly Thr Met Ala Thr Leu Thr Leu Ser Gly Ala Gln Val Glu
65                  70                  75                  80

Asp Glu Ala Asp Tyr Tyr Cys Tyr Ser Thr Asp Ser Thr Asn Tyr His
                85                  90                  95

Trp Val Phe Gly Gly Gly Thr Lys Leu Thr Val Leu Gly Gly Gly Gly
                100                 105                 110

Gly Ser Gly Gly Gly Gly Ser Gln Val Gln Leu Gln Glu Ser Gly Pro
            115                 120                 125

Gly Leu Val Lys Pro Ser Gln Thr Leu Ser Leu Thr Cys Thr Val Ser
130                 135                 140

Gly Gly Ser Ile Asn Asn Asn Tyr Tyr Trp Thr Trp Ile Arg Gln
145                 150                 155                 160

His Pro Gly Lys Gly Leu Glu Trp Ile Gly Tyr Ile Tyr Tyr Ser Gly
                165                 170                 175

Ser Thr Phe Tyr Asn Pro Ser Leu Lys Ser Arg Val Thr Ile Ser Val
            180                 185                 190

Asp Thr Ser Lys Thr Gln Phe Ser Leu Lys Leu Ser Ser Val Thr Ala
        195                 200                 205

Ala Asp Thr Ala Val Tyr Tyr Cys Ala Arg Glu Asp Thr Met Thr Gly
    210                 215                 220

Leu Asp Val Trp Gly Gln Gly Thr Thr Val Thr Val Ser Ser Ala Ser
```

```
                225                 230                 235                 240

Thr Lys Gly Pro Ser Val Phe Pro Leu Ala Pro Cys Ser Arg Ser Thr
                245                 250                 255

Ser Glu Ser Thr Ala Ala Leu Gly Cys Leu Val Lys Asp Tyr Phe Pro
                260                 265                 270

Glu Pro Val Thr Val Ser Trp Asn Ser Gly Ala Leu Thr Ser Gly Val
                275                 280                 285

His Thr Phe Pro Ala Val Leu Gln Ser Ser Gly Leu Tyr Ser Leu Ser
                290                 295                 300

Ser Val Val Thr Val Pro Ser Ser Asn Phe Gly Thr Gln Thr Tyr Thr
305                 310                 315                 320

Cys Asn Val Asp His Lys Pro Ser Asn Thr Lys Val Asp Lys Thr Val
                325                 330                 335

Gly Gly Gly Gly Ser Ala Ala Val Pro Arg Asp Leu Glu Val Val
                340                 345                 350

Ala Ala Thr Pro Thr Ser Leu Leu Ile Ser Trp Asp Ala Pro His His
                355                 360                 365

Gly Val Ala Tyr Tyr Arg Ile Thr Tyr Gly Glu Thr Gly Gly Asn Ser
                370                 375                 380

Pro Val Gln Glu Phe Thr Val Pro Gly Ser Lys Ser Thr Ala Thr Ile
385                 390                 395                 400

Ser Gly Leu Lys Pro Gly Val Asp Tyr Thr Ile Asn Val Tyr Ala Val
                405                 410                 415

Leu Ala Tyr Pro Arg Gly Tyr Pro Leu Ser Lys Pro Ile Ser Ile Asn
                420                 425                 430

Tyr Arg Thr Asp Tyr Lys Asp Asp Asp Lys Gly Ser His His
                435                 440                 445

His His His His
        450

<210> SEQ ID NO 15
<211> LENGTH: 341
<212> TYPE: PRT
<213> ORGANISM: Artificial Sequence
<220> FEATURE:
<223> OTHER INFORMATION: Synthetic polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
                20                  25                  30

Leu Asn Trp Tyr Gln Gln Lys Pro Gly Lys Ala Pro Thr Leu Leu Ile
            35                  40                  45

Tyr Ala Ala Ser Ser Leu Gln Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Gly Gly Gly Gly Ser Gly
                100                 105                 110

Gly Gly Gly Ser Glu Val Gln Leu Val Glu Ser Gly Gly Gly Leu Val
            115                 120                 125

Lys Pro Gly Val Ser Leu Arg Leu Ser Cys Ala Ala Ser Gly Phe Thr
```

```
                130                 135                 140
Phe Ser Arg Tyr Ser Met Asn Trp Val Arg Gln Ala Pro Gly Lys Gly
145                 150                 155                 160

Leu Glu Trp Val Ser Ser Ile Ser Ser Gly Thr Tyr Ile Lys Tyr
                165                 170                 175

Ala Asp Ser Val Lys Gly Arg Phe Thr Ile Ser Arg Asp Asn Ala Lys
                180                 185                 190

Asn Ser Leu Asn Leu Gln Met Asn Ser Leu Arg Ala Glu Asp Thr Ala
                195                 200                 205

Val Tyr Tyr Cys Ala Arg Asp Arg Asp Arg Tyr Pro Leu Asp Tyr Trp
                210                 215                 220

Gly Gln Gly Thr Leu Val Thr Val Ser Ser Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
                260                 265                 270

Val Gln Trp Lys Val Asp Asn Ala Leu Gln Ser Gly Asn Ser Gln Glu
                275                 280                 285

Ser Val Thr Glu Gln Asp Ser Lys Asp Ser Thr Tyr Ser Leu Ser Ser
                290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
                340

<210> SEQ ID NO 16
<211> LENGTH: 581
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
                20                  25                  30

Asn Tyr Tyr Trp Thr Trp Ile Arg Gln His Pro Gly Lys Gly Leu Glu
                35                  40                  45

Trp Ile Gly Tyr Ile Tyr Tyr Ser Gly Ser Thr Phe Tyr Asn Pro Ser
            50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
                100                 105                 110

Thr Leu Val Thr Val Ser Ser Gly Gly Gly Gly Ser Gly Gly Gly Gly
                115                 120                 125

Ser Ser Ser Tyr Glu Leu Thr Gln Pro Pro Ser Val Ser Val Ser Pro
                130                 135                 140

Gly Gln Thr Ala Arg Ile Thr Cys Ser Gly Asp Ala Leu Pro Lys Lys
```

```
             145                 150                 155                 160
Tyr Ala Tyr Trp Tyr Gln Gln Lys Ser Gly Gln Ala Pro Val Leu Val
                165                 170                 175

Ile Tyr Glu Ala Thr Lys Arg Pro Ser Gly Ile Pro Glu Arg Phe Ser
            180                 185                 190

Gly Ser Ser Ser Gly Thr Met Ala Thr Leu Thr Leu Ser Gly Ala Gln
                195                 200                 205

Val Glu Asp Glu Ala Asp Tyr Tyr Cys Tyr Ser Thr Asp Ser Thr Asn
            210                 215                 220

Tyr His Trp Val Phe Gly Gly Thr Lys Leu Thr Val Leu Gly Ala
225                 230                 235                 240

Ser Thr Lys Gly Pro Ser Val Phe Pro Leu Ala Pro Cys Ser Arg Ser
                245                 250                 255

Thr Ser Glu Ser Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
                275                 280                 285

Val His Thr Phe Pro Ala Val Leu Gln Ser Ser Gly Leu Tyr Ser Leu
            290                 295                 300

Ser Ser Val Val Thr Val Pro Ser Ser Asn Phe Gly Thr Gln Thr Tyr
305                 310                 315                 320

Thr Cys Asn Val Asp His Lys Pro Ser Asn Thr Lys Val Asp Lys Thr
                325                 330                 335

Val Ala Ala Ala Glu Pro Lys Ser Ser Asp Lys Thr His Thr Cys Pro
            340                 345                 350

Pro Cys Pro Ala Pro Glu Leu Leu Gly Gly Pro Ser Val Phe Leu Phe
                355                 360                 365

Pro Pro Lys Pro Lys Asp Thr Leu Met Ile Ser Arg Thr Pro Glu Val
            370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
            435                 440                 445

Ser Asn Lys Gln Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Lys Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Lys Ser Asp Gly Ser
            515                 520                 525

Phe Phe Leu Tyr Ser Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys Ala Ala Ala His
                565                 570                 575
```

His His His His His
                580

<210> SEQ ID NO 17
<211> LENGTH: 576
<212> TYPE: PRT
<213> ORGANISM: Artificial Sequence
<220> FEATURE:
<223> OTHER INFORMATION: Synthetic polypeptide

<400> SEQUENCE: 17

Glu Val Gln Leu Val Glu Ser Gly Gly Gly Leu Val Lys Pro Gly Val
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Gly Thr Tyr Ile Lys Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Ala Arg Asp Arg Asp Arg Tyr Pro Leu Asp Tyr Trp Gly Gln Gly Thr
            100                 105                 110

Leu Val Thr Val Ser Ser Gly Gly Gly Ser Gly Gly Gly Gly Ser
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Ser Ile Asn Asn Tyr
145                 150                 155                 160

Leu Asn Trp Tyr Gln Gln Lys Pro Gly Lys Ala Pro Thr Leu Leu Ile
                165                 170                 175

Tyr Ala Ala Ser Ser Leu Gln Ser Gly Val Pro Ser Arg Phe Ser Gly
            180                 185                 190

Ser Arg Ser Gly Thr Asp Phe Thr Leu Thr Ile Ser Ser Leu Gln Pro
        195                 200                 205

Glu Asp Phe Ala Ala Tyr Phe Cys Gln Gln Thr Tyr Ser Asn Pro Thr
    210                 215                 220

Phe Gly Gln Gly Thr Lys Val Glu Val Lys Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys Ala Ala Ala Glu Pro Lys Ser Ser Asp Lys Thr
            340                 345                 350

His Thr Cys Pro Pro Cys Pro Ala Pro Glu Leu Leu Gly Gly Pro Ser
            355                 360                 365

Val Phe Leu Phe Pro Pro Lys Pro Lys Asp Thr Leu Met Ile Ser Arg
370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
            405                 410                 415

Lys Thr Lys Pro Arg Glu Glu Gln Tyr Asn Ser Thr Tyr Arg Val Val
            420                 425                 430

Ser Val Leu Thr Val Leu His Gln Asp Trp Leu Asn Gly Lys Glu Tyr
            435                 440                 445

Lys Cys Lys Val Ser Asn Lys Ala Leu Pro Ala Pro Ile Glu Lys Thr
            450                 455                 460

Ile Ser Lys Ala Lys Gly Gln Pro Arg Glu Pro Gln Val Tyr Thr Leu
465                 470                 475                 480

Pro Pro Ser Arg Glu Glu Met Thr Lys Asn Gln Val Ser Leu Thr Cys
            485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Asp Thr Thr Pro Pro Val Leu Asp
            515                 520                 525

Ser Asp Gly Ser Phe Phe Leu Tyr Ser Asp Leu Thr Val Asp Lys Ser
            530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
            565                 570                 575

<210> SEQ ID NO 18
<211> LENGTH: 470
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Val Glu Ser Gly Gly Gly Leu Val Lys Pro Gly Val
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
            35                  40                  45

Ser Ser Ile Ser Ser Ser Gly Thr Tyr Ile Lys Tyr Ala Asp Ser Val
            50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
            85                  90                  95

Ala Arg Asp Arg Asp Arg Tyr Pro Leu Asp Tyr Trp Gly Gln Gly Thr
            100                 105                 110

Leu Val Thr Val Ser Ser Gly Gly Gly Gly Ser Gly Gly Gly Gly Ser
            115                 120                 125

Asp Ile Gln Met Thr Gln Ser Pro Ser Ser Leu Ser Ala Ser Val Gly
            130                 135                 140

Asp Arg Val Thr Ile Thr Cys Arg Ala Ser Gln Ser Ile Asn Asn Tyr
145                 150                 155                 160

Leu Asn Trp Tyr Gln Gln Lys Pro Gly Lys Ala Pro Thr Leu Leu Ile
            165                 170                 175

Tyr Ala Ala Ser Ser Leu Gln Ser Gly Val Pro Ser Arg Phe Ser Gly
        180                 185                 190

Ser Arg Ser Gly Thr Asp Phe Thr Leu Thr Ile Ser Ser Leu Gln Pro
    195                 200                 205

Glu Asp Phe Ala Ala Tyr Phe Cys Gln Gln Thr Tyr Ser Asn Pro Thr
210                 215                 220

Phe Gly Gln Gly Thr Lys Val Glu Val Lys Arg Ala Ala Ala Glu Pro
225                 230                 235                 240

Lys Ser Ser Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asn
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Asp Thr
                405                 410                 415

Thr Pro Pro Val Leu Asp Ser Asp Gly Ser Phe Phe Leu Tyr Ser Asp
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 19
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 19

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

```
Asn Tyr Tyr Trp Thr Trp Ile Arg Gln His Pro Gly Lys Gly Leu Glu
            35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Leu Val Thr Val Ser Gly Gly Gly Ser Gly Gly Gly Gly
            115                 120                 125

Ser Ser Ser Tyr Glu Leu Thr Gln Pro Pro Ser Val Ser Val Ser Pro
130                 135                 140

Gly Gln Thr Ala Arg Ile Thr Cys Ser Gly Asp Ala Leu Pro Lys Lys
145                 150                 155                 160

Tyr Ala Tyr Trp Tyr Gln Gln Lys Ser Gly Gln Ala Pro Val Leu Val
                165                 170                 175

Ile Tyr Glu Ala Thr Lys Arg Pro Ser Gly Ile Pro Glu Arg Phe Ser
            180                 185                 190

Gly Ser Ser Ser Gly Thr Met Ala Thr Leu Thr Leu Ser Gly Ala Gln
            195                 200                 205

Val Glu Asp Glu Ala Asp Tyr Tyr Cys Tyr Ser Thr Asp Ser Thr Asn
210                 215                 220

Tyr His Trp Val Phe Gly Gly Gly Thr Lys Leu Thr Val Leu Gly Ala
225                 230                 235                 240

Ala Ala Glu Pro Lys Ser Ser Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gln Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Lys Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Lys Leu Thr Val Asp Lys Ser Arg Trp Gln Gln Gly Asn
            435                 440                 445
```

```
Val Phe Ser Cys Ser Val Met His Glu Ala Leu His Asn His Tyr Thr
450                 455                 460
Gln Lys Ser Leu Ser Leu Ser Pro Gly Lys Ala Ala His His His
465                 470                 475                 480
His His His

<210> SEQ ID NO 20
<211> LENGTH: 580
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Asn Ser Tyr
                20                  25                  30
Ala Met Asn Trp Val Arg Gln Ala Pro Gly Lys Gly Leu Glu Trp Val
            35                  40                  45
Ala Arg Ile Arg Ser Lys Tyr Asn Asn Tyr Ala Thr Tyr Tyr Ala Asp
50                  55                  60
Ser Val Lys Gly Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Val Ser Trp Trp
            100                 105                 110
Ala Tyr Trp Gly Gln Gly Thr Leu Val Thr Val Ser Ser Gly Gly Gly
        115                 120                 125
Gly Ser Gly Gly Gly Gly Ser Glu Leu Val Met Thr Gln Thr Pro Ser
130                 135                 140
Ser Leu Ser Ala Ser Leu Gly Asp Arg Val Thr Ile Ser Cys Arg Ala
145                 150                 155                 160
Ser Gln Asp Ile Ser Asn Tyr Leu Asn Trp Tyr Gln Gln Lys Pro Asp
                165                 170                 175
Gly Thr Val Lys Leu Leu Ile Tyr Tyr Thr Ser Arg Leu His Ser Gly
            180                 185                 190
Val Pro Ser Arg Phe Ser Gly Ser Gly Ser Gly Thr Asp Tyr Ser Leu
        195                 200                 205
Thr Ile Ser Asn Leu Glu Gln Glu Asp Ile Ala Thr Tyr Phe Cys Gln
210                 215                 220
Gln Gly Asn Thr Leu Pro Leu Thr Phe Gly Ala Gly Thr Lys Leu Glu
225                 230                 235                 240
Ile Lys Ala Ser Thr Lys Gly Pro Ser Val Phe Pro Leu Ala Pro Cys
                245                 250                 255
Ser Arg Ser Thr Ser Glu Ser Thr Ala Ala Leu Gly Cys Leu Val Lys
            260                 265                 270
Asp Tyr Phe Pro Glu Pro Val Thr Val Ser Trp Asn Ser Gly Ala Leu
        275                 280                 285
Thr Ser Gly Val His Thr Phe Pro Ala Val Leu Gln Ser Ser Gly Leu
290                 295                 300
Tyr Ser Leu Ser Ser Val Val Thr Val Pro Ser Ser Asn Phe Gly Thr
305                 310                 315                 320
Gln Thr Tyr Thr Cys Asn Val Asp His Lys Pro Ser Asn Thr Lys Val
```

```
                    325                 330                 335
Asp Lys Thr Val Gly Gly Gly Ser Ala Ala Glu Pro Lys Ser
                340                 345                 350

Ser Asp Lys Thr His Thr Cys Pro Pro Cys Pro Ala Pro Glu Ala Ala
                355                 360                 365

Gly Gly Pro Ser Val Phe Leu Phe Pro Pro Lys Pro Lys Asp Thr Leu
            370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
            435                 440                 445

Gly Lys Glu Tyr Lys Cys Lys Val Ser Asn Lys Ala Leu Pro Ala Pro
        450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Asp Thr Thr Pro
            515                 520                 525

Pro Val Leu Asp Ser Asp Gly Ser Phe Phe Leu Tyr Ser Asp Leu Thr
        530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 21
<211> LENGTH: 590
<212> TYPE: PRT
<213> ORGANISM: Artificial Sequence
<220> FEATURE:
<223> OTHER INFORMATION: Synthetic polypeptide

<400> SEQUENCE: 21

Glu Val Gln Leu Leu Glu Gln Ser Gly Ala Glu Leu Val Arg Pro Gly
1               5                   10                  15

Ala Leu Val Lys Leu Ser Cys Lys Ala Ser Gly Phe Lys Ile Lys Asp
            20                  25                  30

Tyr Phe Val Asn Trp Val Lys Gln Arg Pro Glu Gln Gly Leu Glu Trp
        35                  40                  45

Ile Gly Trp Ile Asp Pro Glu Asn Asp Asn Ser Leu Tyr Gly Pro Asn
    50                  55                  60

Phe Gln Asp Lys Ala Ser Ile Thr Ala Asp Thr Ser Ser Asn Thr Gly
65                  70                  75                  80

Tyr Leu Gln Leu Ser Gly Leu Thr Ser Glu Asp Thr Ala Val Tyr Tyr
                85                  90                  95

Cys Ala Leu Tyr Tyr Gly Ser Arg Gly Asp Ala Met Asp Tyr Trp Gly
```

```
                100                 105                 110
Gln Gly Thr Thr Val Thr Val Ser Ser Gly Gly Gly Ser Gly Gly
            115                 120                 125

Gly Gly Ser Gln Thr Val Val Thr Gln Glu Pro Ser Leu Thr Val Ser
            130                 135                 140

Pro Gly Gly Thr Val Thr Leu Thr Cys Gly Ser Ser Thr Gly Ala Val
145                 150                 155                 160

Thr Ser Gly Asn Tyr Pro Asn Trp Val Gln Gln Lys Pro Gly Gln Ala
                165                 170                 175

Pro Arg Gly Leu Ile Gly Gly Thr Lys Phe Leu Ala Pro Gly Thr Pro
            180                 185                 190

Ala Arg Phe Ser Gly Ser Leu Leu Gly Gly Lys Ala Ala Leu Thr Leu
            195                 200                 205

Ser Gly Val Gln Pro Glu Asp Glu Ala Glu Tyr Tyr Cys Val Leu Trp
            210                 215                 220

Tyr Ser Asn Arg Trp Val Phe Gly Gly Gly Thr Lys Leu Thr Val Leu
225                 230                 235                 240

Gly Gln Pro Lys Ala Ala Pro Ser Val Thr Leu Phe Pro Pro Ser Ser
                245                 250                 255

Glu Glu Leu Gln Ala Asn Lys Ala Thr Leu Val Cys Leu Ile Ser Asp
            260                 265                 270

Phe Tyr Pro Gly Ala Val Thr Val Ala Trp Lys Ala Asp Ser Ser Pro
            275                 280                 285

Val Lys Ala Gly Val Glu Thr Thr Thr Pro Ser Lys Gln Ser Asn Asn
            290                 295                 300

Lys Tyr Ala Ala Ser Ser Tyr Leu Ser Leu Thr Pro Glu Gln Trp Lys
305                 310                 315                 320

Ser His Arg Ser Tyr Ser Cys Gln Val Thr His Glu Gly Ser Thr Val
                325                 330                 335

Glu Lys Thr Val Ala Pro Thr Glu Cys Ser Ala Ala Ala Glu Pro Lys
            340                 345                 350

Ser Ser Asp Lys Thr His Thr Cys Pro Pro Cys Pro Ala Pro Glu Ala
            355                 360                 365

Ala Gly Gly Pro Ser Val Phe Leu Phe Pro Pro Lys Pro Lys Asp Thr
            370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
            435                 440                 445

Asn Gly Lys Glu Tyr Lys Cys Lys Val Ser Asn Lys Ala Leu Pro Ala
450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Lys Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
            515                 520                 525
```

```
Pro Pro Val Leu Lys Ser Asp Gly Ser Phe Phe Leu Tyr Ser Lys Leu
    530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
            565                 570                 575

Leu Ser Pro Gly Lys Ala Ala Ala His His His His His His
            580                 585                 590
```

<210> SEQ ID NO 22
<211> LENGTH: 583
<212> TYPE: PRT
<213> ORGANISM: Artificial Sequence
<220> FEATURE:
<223> OTHER INFORMATION: Synthetic polypeptide

<400> SEQUENCE: 22

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gln Ser Val Leu Thr Gln Pro Pro Ser
    130                 135                 140

Val Ser Glu Ala Pro Arg Gln Arg Val Thr Ile Ser Cys Ser Gly Ser
145                 150                 155                 160

Ser Ser Asn Ile Gly Asn Asn Ala Val Asn Trp Tyr Gln Gln Leu Pro
                165                 170                 175

Gly Lys Ala Pro Lys Leu Leu Ile Tyr Tyr Asp Asp Met Leu Ser Ser
            180                 185                 190

Gly Val Ser Asp Arg Phe Ser Gly Ser Lys Ser Gly Thr Ser Ala Ser
        195                 200                 205

Leu Ala Ile Ser Gly Leu Gln Ser Glu Asp Glu Ala Asp Tyr Tyr Cys
    210                 215                 220

Ala Ala Trp Asp Asp Ser Leu Asn Gly Val Val Phe Gly Gly Gly Thr
225                 230                 235                 240

Lys Leu Thr Val Leu Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300
```

```
Ser Gly Leu Tyr Ser Leu Ser Ser Val Val Thr Val Pro Ser Ser Asn
305                 310                 315                 320

Phe Gly Thr Gln Thr Tyr Thr Cys Asn Val Asp His Lys Pro Ser Asn
            325                 330                 335

Thr Lys Val Asp Lys Thr Val Gly Gly Gly Ser Ala Ala Ala Glu
        340                 345                 350

Pro Lys Ser Ser Asp Lys Thr His Thr Cys Pro Pro Cys Pro Ala Pro
            355                 360                 365

Glu Ala Ala Gly Gly Pro Ser Val Phe Leu Phe Pro Pro Lys Pro Lys
        370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Ala Leu
450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Asp
            515                 520                 525

Thr Thr Pro Pro Val Leu Asp Ser Asp Gly Ser Phe Phe Leu Tyr Ser
530                 535                 540

Asp Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 23
<211> LENGTH: 587
<212> TYPE: PRT
<213> ORGANISM: Artificial Sequence
<220> FEATURE:
<223> OTHER INFORMATION: Synthetic polypeptide

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80
```

```
Ser Leu Lys Leu Ser Ser Val Thr Ala Ala Asp Thr Ala Val Tyr Tyr
                85                  90                  95

Cys Ala Arg Gly Ser Ser Trp Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gln Thr Val Val Thr Gln Glu Pro Ser Leu Thr Val Ser Pro Gly Gly
    130                 135                 140

Thr Val Thr Leu Thr Cys Gly Ser Ser Thr Gly Ala Val Thr Ser Gly
145                 150                 155                 160

Asn Tyr Pro Asn Trp Val Gln Gln Lys Pro Gly Gln Ala Pro Arg Gly
                165                 170                 175

Leu Ile Gly Gly Thr Lys Phe Leu Ala Pro Gly Thr Pro Ala Arg Phe
            180                 185                 190

Ser Gly Ser Leu Leu Gly Gly Lys Ala Ala Leu Thr Leu Ser Gly Val
        195                 200                 205

Gln Pro Glu Asp Glu Ala Glu Tyr Tyr Cys Val Leu Trp Tyr Ser Asn
    210                 215                 220

Arg Trp Val Phe Gly Gly Gly Thr Lys Leu Thr Val Leu Gly Gln Pro
225                 230                 235                 240

Lys Ala Ala Pro Ser Val Thr Leu Phe Pro Pro Ser Ser Glu Glu Leu
                245                 250                 255

Gln Ala Asn Lys Ala Thr Leu Val Cys Leu Ile Ser Asp Phe Tyr Pro
            260                 265                 270

Gly Ala Val Thr Val Ala Trp Lys Ala Asp Ser Ser Pro Val Lys Ala
        275                 280                 285

Gly Val Glu Thr Thr Thr Pro Ser Lys Gln Ser Asn Asn Lys Tyr Ala
    290                 295                 300

Ala Ser Ser Tyr Leu Ser Leu Thr Pro Glu Gln Trp Lys Ser His Arg
305                 310                 315                 320

Ser Tyr Ser Cys Gln Val Thr His Glu Gly Ser Thr Val Glu Lys Thr
                325                 330                 335

Val Ala Pro Thr Glu Cys Ser Ala Ala Ala Pro Lys Ser Ser Asp
            340                 345                 350

Lys Thr His Thr Cys Pro Pro Cys Pro Ala Pro Glu Ala Ala Gly Gly
        355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
        435                 440                 445

Glu Tyr Lys Cys Lys Val Ser Asn Lys Ala Leu Pro Ala Pro Ile Glu
    450                 455                 460

Lys Thr Ile Ser Lys Ala Lys Gly Gln Pro Arg Glu Pro Gln Val Tyr
465                 470                 475                 480

Thr Leu Pro Pro Ser Arg Lys Glu Met Thr Lys Asn Gln Val Ser Leu
                485                 490                 495
```

```
Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
        515                 520                 525

Leu Lys Ser Asp Gly Ser Phe Phe Leu Tyr Ser Lys Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys Ala Ala Ala His His His His His His
            580                 585
```

<210> SEQ ID NO 24
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 24

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Pro Gly Asn Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Gln Lys Glu Trp Arg Leu Ile Phe Asp Tyr Trp Gly Gln
            100                 105                 110

Gly Thr Leu Val Thr Val Ser Ser Ala Ser Thr Lys Gly Pro Gln Val
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ile Ser His Tyr Trp
145                 150                 155                 160

Ser Trp Ile Arg Gln Pro Pro Gly Lys Gly Leu Glu Trp Ile Gly Tyr
                165                 170                 175

Ile Tyr Tyr Ser Gly Ser Thr Asn Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Thr Ser Val Thr Ala Ala Asp Thr Ala Val Tyr Tyr Cys Ala Arg Asp
    210                 215                 220

Gly Trp Ser Ala Phe Asp Tyr Trp Gly Gln Gly Thr Leu Val Thr Val
225                 230                 235                 240

Ser Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270
```

```
Asp Tyr Phe Pro Glu Pro Val Thr Val Ser Trp Asn Ser Gly Ala Leu
            275                 280                 285
Thr Ser Gly Val His Thr Phe Pro Ala Val Leu Gln Ser Ser Gly Leu
        290                 295                 300
Tyr Ser Leu Ser Ser Val Val Thr Val Pro Ser Ser Asn Phe Gly Thr
305                 310                 315                 320
Gln Thr Tyr Thr Cys Asn Val Asp His Lys Pro Ser Asn Thr Lys Val
            325                 330                 335
Asp Lys Thr Val Gly Gly Gly Ser Ala Ala Val Pro Arg Asp
        340                 345                 350
Leu Glu Val Val Ala Ala Thr Pro Thr Ser Leu Leu Ile Ser Trp Asp
            355                 360                 365
Ala Pro His His Gly Val Ala Tyr Tyr Arg Ile Thr Tyr Gly Glu Thr
        370                 375                 380
Gly Gly Asn Ser Pro Val Gln Glu Phe Thr Val Pro Gly Ser Lys Ser
385                 390                 395                 400
Thr Ala Thr Ile Ser Gly Leu Lys Pro Gly Val Asp Tyr Thr Ile Asn
            405                 410                 415
Val Tyr Ala Val Leu Ala Tyr Pro Arg Gly Tyr Pro Leu Ser Lys Pro
        420                 425                 430
Ile Ser Ile Asn Tyr Arg Thr Asp Tyr Lys Asp Asp Asp Lys Gly
            435                 440                 445
Ser Ser His His His His His His
        450                 455

<210> SEQ ID NO 25
<211> LENGTH: 327
<212> TYPE: PRT
<213> ORGANISM: Artificial Sequence
<220> FEATURE:
<223> OTHER INFORMATION: Synthetic polypeptide

<400> SEQUENCE: 25

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Ala Ala Phe Thr Leu Thr Ile Ser Ser Leu Gln Pro
65                  70                  75                  80
Glu Asp Phe Ala Thr Tyr Phe Cys Gln Gln Ala Asn Ser Phe Pro Leu
            85                  90                  95
Thr Phe Ala Gly Gly Thr Lys Val Asp Ile Lys Arg Thr Val Ala Ala
        100                 105                 110
Pro Asp Ile Gln Met Thr Gln Ser Pro Ser Ser Leu Ser Ala Ser Val
    115                 120                 125
Gly Asp Arg Val Thr Ile Thr Cys Arg Ala Ser Gln Gly Ile Arg Asn
130                 135                 140
Ala Leu Gly Trp Tyr Gln Gln Lys Pro Gly Lys Ala Pro Lys Arg Leu
145                 150                 155                 160
Ile Tyr Ala Ala Ser Ser Leu Gln Ser Gly Val Pro Ser Arg Phe Ser
            165                 170                 175
```

Gly Ser Gly Ser Gly Thr Glu Phe Thr Leu Thr Ile Ser Ser Leu Gln
            180                 185                 190

Pro Glu Asp Phe Ala Thr Tyr Tyr Cys Leu Gln His Asn Ser Tyr Pro
        195                 200                 205

Arg Thr Phe Gly Gln Gly Thr Lys Val Glu Ile Arg Arg Thr Val Ala
    210                 215                 220

Ala Pro Ser Val Phe Ile Phe Pro Pro Ser Asp Glu Gln Leu Lys Ser
225                 230                 235                 240

Gly Thr Ala Ser Val Cys Leu Leu Asn Asn Phe Tyr Pro Arg Glu
            245                 250                 255

Ala Lys Val Gln Trp Lys Val Asp Asn Ala Leu Gln Ser Gly Asn Ser
        260                 265                 270

Gln Glu Ser Val Thr Glu Gln Asp Ser Lys Asp Ser Thr Tyr Ser Leu
    275                 280                 285

Ser Ser Thr Leu Thr Leu Ser Lys Ala Asp Tyr Glu Lys His Lys Val
290                 295                 300

Tyr Ala Cys Glu Val Thr His Gln Gly Leu Ser Ser Pro Val Thr Lys
305                 310                 315                 320

Ser Phe Asn Arg Gly Glu Cys
            325

<210> SEQ ID NO 26
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
            85                  90                  95

Cys Ala Arg Glu Asp Thr Met Thr Gly Leu Asp Val Trp Gly Gln Gly
        100                 105                 110

Thr Leu Val Thr Val Ser Ser Gly Gly Gly Ser Gly Gly Gly Gly
            115                 120                 125

Ser Asp Ile Gln Met Thr Gln Ser Pro Ser Ser Val Ser Ala Ser Val
130                 135                 140

Gly Asp Arg Val Thr Ile Thr Cys Arg Ala Ser Gln Gly Ile Ser Ser
145                 150                 155                 160

Trp Leu Ala Trp Tyr Gln Gln Lys Pro Gly Lys Ala Pro Lys Leu Leu
            165                 170                 175

Ile Tyr Ala Ala Ser Ser Leu Gln Ser Gly Val Pro Ser Arg Phe Ser
        180                 185                 190

Gly Ser Gly Ser Gly Ala Ala Phe Thr Leu Thr Ile Ser Ser Leu Gln
    195                 200                 205

```
Pro Glu Asp Phe Ala Thr Tyr Phe Cys Gln Gln Ala Asn Ser Phe Pro
    210                 215                 220

Leu Thr Phe Ala Gly Gly Thr Lys Val Asp Ile Lys Arg Ala Ser Thr
225                 230                 235                 240

Lys Gly Pro Ser Val Phe Pro Leu Ala Pro Cys Ser Arg Ser Thr Ser
                245                 250                 255

Glu Ser Thr Ala Ala Leu Gly Cys Leu Val Lys Asp Tyr Phe Pro Glu
                260                 265                 270

Pro Val Thr Val Ser Trp Asn Ser Gly Ala Leu Thr Ser Gly Val His
            275                 280                 285

Thr Phe Pro Ala Val Leu Gln Ser Ser Gly Leu Tyr Ser Leu Ser Ser
    290                 295                 300

Val Val Thr Val Pro Ser Ser Asn Phe Gly Thr Gln Thr Tyr Thr Cys
305                 310                 315                 320

Asn Val Asp His Lys Pro Ser Asn Thr Lys Val Asp Lys Thr Val Gly
                325                 330                 335

Gly Gly Gly Ser Ala Ala Ala Val Pro Arg Asp Leu Glu Val Val Ala
            340                 345                 350

Ala Thr Pro Thr Ser Leu Leu Ile Ser Trp Asp Ala Pro His His Gly
    355                 360                 365

Val Ala Tyr Tyr Arg Ile Thr Tyr Gly Glu Thr Gly Gly Asn Ser Pro
370                 375                 380

Val Gln Glu Phe Thr Val Pro Gly Ser Lys Ser Thr Ala Thr Ile Ser
385                 390                 395                 400

Gly Leu Lys Pro Gly Val Asp Tyr Thr Ile Asn Val Tyr Ala Val Leu
                405                 410                 415

Ala Tyr Pro Arg Gly Tyr Pro Leu Ser Lys Pro Ile Ser Ile Asn Tyr
            420                 425                 430

Arg Thr Asp Tyr Lys Asp Asp Asp Lys Gly Ser Ser His His His
            435                 440                 445

His His His
    450

<210> SEQ ID NO 27
<211> LENGTH: 343
<212> TYPE: PRT
<213> ORGANISM: Artificial Sequence
<220> FEATURE:
<223> OTHER INFORMATION: Synthetic polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Pro Gly Asn Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Gln Lys Glu Trp Arg Leu Ile Phe Asp Tyr Trp Gly Gln
            100                 105                 110
```

```
Gly Thr Leu Val Thr Val Ser Gly Gly Gly Gly Ser Gly Gly Gly
            115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Ser Ile Asn
145                 150                 155                 160

Asn Tyr Leu Asn Trp Tyr Gln Gln Lys Pro Gly Lys Ala Pro Thr Leu
                165                 170                 175

Leu Ile Tyr Ala Ala Ser Ser Leu Gln Ser Gly Val Pro Ser Arg Phe
            180                 185                 190

Ser Gly Ser Arg Ser Gly Thr Asp Phe Thr Leu Thr Ile Ser Ser Leu
        195                 200                 205

Gln Pro Glu Asp Phe Ala Ala Tyr Phe Cys Gln Gln Thr Tyr Ser Asn
    210                 215                 220

Pro Thr Phe Gly Gln Gly Thr Lys Val Glu Val Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
    290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
            340

<210> SEQ ID NO 28
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 28

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Ala Phe Thr Leu Thr Ile Ser Ser Leu Gln Pro
65                  70                  75                  80

Glu Asp Phe Ala Thr Tyr Phe Cys Gln Gln Ala Asn Ser Phe Pro Leu
                85                  90                  95

Thr Phe Ala Gly Gly Thr Lys Val Asp Ile Lys Arg Gly Gly Gly Gly
            100                 105                 110

Ser Gly Gly Gly Gly Ser Gln Val Gln Leu Gln Glu Ser Gly Pro Gly
        115                 120                 125
```

Leu Val Lys Pro Ser Gln Thr Leu Ser Leu Thr Cys Thr Val Ser Gly
            130                 135                 140

Gly Ser Ile Asn Asn Asn Tyr Tyr Trp Thr Trp Ile Arg Gln His
145                 150                 155                 160

Pro Gly Lys Gly Leu Glu Trp Ile Gly Tyr Ile Tyr Tyr Ser Gly Ser
                165                 170                 175

Thr Phe Tyr Asn Pro Ser Leu Lys Ser Arg Val Thr Ile Ser Val Asp
            180                 185                 190

Thr Ser Lys Thr Gln Phe Ser Leu Lys Leu Ser Ser Val Thr Ala Ala
        195                 200                 205

Asp Thr Ala Val Tyr Tyr Cys Ala Arg Glu Asp Thr Met Thr Gly Leu
    210                 215                 220

Asp Val Trp Gly Gln Gly Thr Thr Val Thr Val Ser Ser Ala Ser Thr
225                 230                 235                 240

Lys Gly Pro Ser Val Phe Pro Leu Ala Pro Cys Ser Arg Ser Thr Ser
                245                 250                 255

Glu Ser Thr Ala Ala Leu Gly Cys Leu Val Lys Asp Tyr Phe Pro Glu
            260                 265                 270

Pro Val Thr Val Ser Trp Asn Ser Gly Ala Leu Thr Ser Gly Val His
        275                 280                 285

Thr Phe Pro Ala Val Leu Gln Ser Ser Gly Leu Tyr Ser Leu Ser Ser
    290                 295                 300

Val Val Thr Val Pro Ser Ser Asn Phe Gly Thr Gln Thr Tyr Thr Cys
305                 310                 315                 320

Asn Val Asp His Lys Pro Ser Asn Thr Lys Val Asp Lys Thr Val Gly
                325                 330                 335

Gly Gly Gly Ser Ala Ala Ala Val Pro Arg Asp Leu Glu Val Val Ala
            340                 345                 350

Ala Thr Pro Thr Ser Leu Leu Ile Ser Trp Asp Ala Pro His His Gly
        355                 360                 365

Val Ala Tyr Tyr Arg Ile Thr Tyr Gly Glu Thr Gly Gly Asn Ser Pro
    370                 375                 380

Val Gln Glu Phe Thr Val Pro Gly Ser Lys Ser Thr Ala Thr Ile Ser
385                 390                 395                 400

Gly Leu Lys Pro Gly Val Asp Tyr Thr Ile Asn Val Tyr Ala Val Leu
                405                 410                 415

Ala Tyr Pro Arg Gly Tyr Pro Leu Ser Lys Pro Ile Ser Ile Asn Tyr
            420                 425                 430

Arg Thr Asp Tyr Lys Asp Asp Asp Lys Gly Ser Ser His His His His
        435                 440                 445

His His His
    450

<210> SEQ ID NO 29
<211> LENGTH: 343
<212> TYPE: PRT
<213> ORGANISM: Artificial Sequence
<220> FEATURE:
<223> OTHER INFORMATION: Synthetic polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

```
Leu Asn Trp Tyr Gln Gln Lys Pro Gly Lys Ala Pro Thr Leu Leu Ile
         35                  40                  45

Tyr Ala Ala Ser Ser Leu Gln Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Ala Tyr Phe Cys Gln Gln Thr Tyr Ser Asn Pro Thr
                 85                  90                  95

Phe Gly Gln Gly Thr Lys Val Glu Val Lys Gly Gly Gly Gly Ser Gly
                100                 105                 110

Gly Gly Gly Ser Gln Val Gln Leu Val Glu Ser Gly Gly Gly Val Val
            115                 120                 125

Gln Pro Gly Arg Ser Leu Arg Leu Ser Cys Ala Ala Ser Gly Phe Thr
        130                 135                 140

Phe Ser Ser Tyr Gly Met His Trp Val Arg Gln Ala Pro Gly Lys Gly
145                 150                 155                 160

Leu Glu Trp Val Ala Val Ile Ser Tyr Pro Gly Asn Thr Lys Tyr Tyr
                165                 170                 175

Ala Asp Ser Val Lys Gly Arg Phe Thr Ile Ser Arg Asp Asn Ser Lys
            180                 185                 190

Asn Thr Leu Tyr Leu Gln Met Asn Ser Leu Arg Ala Glu Asp Thr Ala
        195                 200                 205

Val Tyr Phe Cys Ala Arg Asp Gln Lys Glu Trp Arg Leu Ile Phe Asp
210                 215                 220

Tyr Trp Gly Gln Gly Thr Leu Val Thr Val Ser Ser Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
            340

<210> SEQ ID NO 30
<211> LENGTH: 463
<212> TYPE: PRT
<213> ORGANISM: Artificial Sequence
<220> FEATURE:
<223> OTHER INFORMATION: Synthetic polypeptide

<400> SEQUENCE: 30

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45
```

```
Ala Val Ile Ser Tyr Pro Gly Asn Thr Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Arg Asp Gln Lys Glu Trp Arg Leu Ile Phe Asp Tyr Trp Gly Gln
                100                 105                 110

Gly Thr Leu Val Thr Val Ser Ser Gly Gly Gly Ser Gly Gly Gly
            115                 120                 125

Gly Ser Gln Val Gln Leu Gln Glu Ser Gly Pro Gly Leu Val Lys Pro
    130                 135                 140

Ser Gln Thr Leu Ser Leu Thr Cys Thr Val Ser Gly Gly Ser Ile Asn
145                 150                 155                 160

Asn Asn Asn Tyr Tyr Trp Thr Trp Ile Arg Gln His Pro Gly Lys Gly
                165                 170                 175

Leu Glu Trp Ile Gly Tyr Ile Tyr Tyr Ser Gly Ser Thr Phe Tyr Asn
                180                 185                 190

Pro Ser Leu Lys Ser Arg Val Thr Ile Ser Val Asp Thr Ser Lys Thr
                195                 200                 205

Gln Phe Ser Leu Lys Leu Ser Ser Val Thr Ala Ala Asp Thr Ala Val
    210                 215                 220

Tyr Tyr Cys Ala Arg Glu Asp Thr Met Thr Gly Leu Asp Val Trp Gly
225                 230                 235                 240

Gln Gly Thr Thr Val Thr Val Ser Ser Ala Ser Thr Lys Gly Pro Ser
                245                 250                 255

Val Phe Pro Leu Ala Pro Cys Ser Arg Ser Thr Ser Glu Ser Thr Ala
                260                 265                 270

Ala Leu Gly Cys Leu Val Lys Asp Tyr Phe Pro Glu Pro Val Thr Val
            275                 280                 285

Ser Trp Asn Ser Gly Ala Leu Thr Ser Gly Val His Thr Phe Pro Ala
    290                 295                 300

Val Leu Gln Ser Ser Gly Leu Tyr Ser Leu Ser Ser Val Val Thr Val
305                 310                 315                 320

Pro Ser Ser Asn Phe Gly Thr Gln Thr Tyr Thr Cys Asn Val Asp His
                325                 330                 335

Lys Pro Ser Asn Thr Lys Val Asp Lys Thr Val Gly Gly Gly Gly Ser
                340                 345                 350

Ala Ala Ala Val Pro Arg Asp Leu Glu Val Val Ala Thr Pro Thr
            355                 360                 365

Ser Leu Leu Ile Ser Trp Asp Ala Pro His His Gly Val Ala Tyr Tyr
    370                 375                 380

Arg Ile Thr Tyr Gly Glu Thr Gly Gly Asn Ser Pro Val Gln Glu Phe
385                 390                 395                 400

Thr Val Pro Gly Ser Lys Ser Thr Ala Thr Ile Ser Gly Leu Lys Pro
                405                 410                 415

Gly Val Asp Tyr Thr Ile Asn Val Tyr Ala Val Leu Ala Tyr Pro Arg
                420                 425                 430

Gly Tyr Pro Leu Ser Lys Pro Ile Ser Ile Asn Tyr Arg Thr Asp Tyr
            435                 440                 445

Lys Asp Asp Asp Asp Lys Gly Ser Ser His His His His His His
    450                 455                 460
```

<210> SEQ ID NO 31
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 31

```
Asp Ile Gln Met Thr Gln Ser Pro Ser Ser Val Ser Ala Ser Val Gly
1               5                  10                   15

Asp Arg Val Thr Ile Thr Cys Arg Ala Ser Gln Gly Ile Ser Ser Trp
            20                  25                   30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Ala Ala Phe Thr Leu Thr Ile Ser Ser Leu Gln Pro
65                  70                  75                  80

Glu Asp Phe Ala Thr Tyr Phe Cys Gln Gln Ala Asn Ser Phe Pro Leu
                85                  90                  95

Thr Phe Ala Gly Gly Thr Lys Val Asp Ile Lys Arg Gly Gly Gly Gly
            100                 105                 110

Ser Gly Gly Gly Gly Ser Asp Ile Gln Met Thr Gln Ser Pro Ser Ser
        115                 120                 125

Leu Ser Ala Ser Val Gly Asp Arg Val Thr Ile Thr Cys Arg Ala Ser
130                 135                 140

Gln Ser Ile Asn Asn Tyr Leu Asn Trp Tyr Gln Gln Lys Pro Gly Lys
145                 150                 155                 160

Ala Pro Thr Leu Leu Ile Tyr Ala Ala Ser Ser Leu Gln Ser Gly Val
                165                 170                 175

Pro Ser Arg Phe Ser Gly Ser Arg Ser Gly Thr Asp Phe Thr Leu Thr
            180                 185                 190

Ile Ser Ser Leu Gln Pro Glu Asp Phe Ala Ala Tyr Phe Cys Gln Gln
        195                 200                 205

Thr Tyr Ser Asn Pro Thr Phe Gly Gln Gly Thr Lys Val Glu Val Lys
210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255

Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330
```

<210> SEQ ID NO 32
<211> LENGTH: 1371
<212> TYPE: DNA
<213> ORGANISM: Artificial Sequence
<220> FEATURE:
<223> OTHER INFORMATION: Synthetic polynucleotide

<400> SEQUENCE: 32

```
caggtgcagc tgcaggagtc gggcccagga ctggtgaagc cttcacagac cctgtccctc        60
acctgcactg tctctggtgg ctccatcaac aataataatt actactggac ctggatccgc       120
cagcacccag ggaagggcct ggagtggatt gggtacatct attacagtgg gagcaccttc       180
tacaacccgt ccctcaagag tcgagttacc atatcagtcg acacgtctaa gacccagttc       240
tccctgaagt tgagctctgt gactgccgcg gacacggccg tgtattactg tgcgagagag       300
gatacgatga cgggcctgga cgtctggggc caagggaccc tggtcaccgt ctcctcagcc       360
tctacaaagg gtcctgaggt gcagctggtg gagtctgggg gaggcctggt caagcctggg       420
gtgtccctga gactctcctg tgcagcctct ggattcacct cagtagata tagcatgaac       480
tgggtccgcc aggctccagg aaggggctg gagtgggtct catccattag tagtagtggt        540
acttacataa agtacgcaga ctcagtgaag gccgattca ccatctccag agacaacgcc        600
aagaactcac tgaatctgca aatgaacagc ctgagagccg aggacacggc tgtgtattat       660
tgtgcgagag atcgggaccg gtatcccctt gactactggg gccagggaac cctggtcact       720
gtctcctcag ctagcaccaa gggcccatcg gtcttccccc tggcgccctg ctccaggagc       780
acctccgaga gcacagcggc cctgggctgc ctggtcaagg actacttccc cgaaccggtg       840
acggtgtcgt ggaactcagg cgctctgacc agcggcgtgc acaccttccc agctgtccta       900
cagtcctcag gactctactc cctcagcagc gtggtgaccg tgccctccag caacttcggc       960
acccagacct acacctgcaa cgtagatcac aagcccagca acaccaaggt ggacaagaca      1020
gttggcggag gtggctctgc ggccgccgtt ccacgtgatt tggaagttgt tgcagcaact      1080
ccaactagtc tgctgatcag ctgggatgcg ccgcatcatg tgttgctta ttatcgcatt       1140
acgtacggcg aaaccggcgg caacagcccg gtgcaggaat tcacggtacc gggcagcaaa      1200
agcaccgcga ccatttccgg actgaaaccg gcgtggatt ataccattaa cgtgtatgcg       1260
gtgctggctt acccgcgtgg ttacccgctg agcaaaccga ttagcattaa ttatcggacc      1320
gactacaaag acgatgacga caagggcagt tctcaccatc accatcacca c              1371
```

<210> SEQ ID NO 33
<211> LENGTH: 981
<212> TYPE: DNA
<213> ORGANISM: Artificial Sequence
<220> FEATURE:
<223> OTHER INFORMATION: Synthetic polynucleotide

<400> SEQUENCE: 33

```
gacatccaga tgacccagtc tccatcctcc ctgtctgcat ctgtaggaga cagagtcacc        60
atcacttgcc gggctagtca gagcattaac aactatttaa attggtatca gcagaaacca       120
gggaaagccc ctacgctcct gatctatgct gcatccagtt tgcaaagtgg ggtcccatca       180
aggttcagtg gcagtagatc tgggacagat ttcactctca ccatcagcag tctgcaacct       240
gaagattttg cagcttactt ctgtcaacag acttacagta cccgacgtt cggccaaggg        300
accaaggtgg aagtcaaacg tacggtggct gcaccaagct cctatgagct gacacagcca       360
cccctcggtgt cagtgtcccc aggacaaacg gccaggatca cctgctctgg agatgcattg       420
ccaaaaaat atgcttattg gtaccagcag aagtcaggcc aggcccctgt gctggtcatc       480
tatgaggcca ccaaacgacc ctccgggatc cctgagagat tctctggctc cagctcaggg      540
acaatggcca ccttgactct cagtggggcc caggtggagg atgaagctga ctactactgt       600
```

| | |
|---|---|
| tactcaacag acagcactaa ttatcattgg gtgttcggcg agggaccaa gctgaccgtc | 660 |
| ctaggccaac cgaaagcggc gccctcggtc actctgttcc cgccctcctc tgaggagctt | 720 |
| caagccaaca aggccacact ggtgtgtctc ataagtgact tctacccggg agccgtgaca | 780 |
| gtggcctgga aggcagatag cagccccgtc aaggcgggag tggagaccac cacaccctcc | 840 |
| aaacaaagca acaacaagta cgcggccagc agctatctga gcctgacgcc tgagcagtgg | 900 |
| aagtcccaca gaagctacag ctgccaggtc acgcatgaag ggagcaccgt ggagaagaca | 960 |
| gtggccccta cagaatgttc a | 981 |

<210> SEQ ID NO 34
<211> LENGTH: 1359
<212> TYPE: DNA
<213> ORGANISM: Artificial Sequence
<220> FEATURE:
<223> OTHER INFORMATION: Synthetic polynucleotide

<400> SEQUENCE: 34

| | |
|---|---|
| caggtgcagc tgcaggagtc gggcccagga ctggtgaagc cttcacagac cctgtccctc | 60 |
| acctgcactg tctctggtgg ctccatcaac aataataatt actactggac ctggatccgc | 120 |
| cagcacccag ggaagggcct ggagtggatt gggtacatct attacagtgg gagccacttc | 180 |
| tacaacccgt ccctcaagag tcgagttacc atatcagtcg acacgtctaa gacccagttc | 240 |
| tccctgaagt tgagctctgt gactgccgcg gacacggccg tgtattactg tgcgagagag | 300 |
| gatacgatga cgggcctgga cgtctggggc caagggaccc tggtcaccgt ctcctcagga | 360 |
| ggcggcggtt caggcggagg tggctctagc tcctatgagc tgacacagcc accctcggtg | 420 |
| tcagtgtccc caggacaaac ggccaggatc acctgctctg agatgcatt gccaaaaaaa | 480 |
| tatgcttatt ggtaccagca gaagtcaggc caggcccctg tgctggtcat ctatgaggcc | 540 |
| accaaacgac cctccgggat ccctgagaga ttctctggct ccagctcagg acaatggcc | 600 |
| accttgactc tcagtggggc ccaggtggag gatgaagctg actactactg ttactcaaca | 660 |
| gacagcacta attatcattg ggtgttcggc ggagggacca agctgaccgt cctaggcgct | 720 |
| agcaccaagg gcccatcggt cttccccctg gcgccctgct ccaggagcac ctccgagagc | 780 |
| acagcggccc tgggctgcct ggtcaaggac tacttccccg aaccggtgac ggtgtcgtgg | 840 |
| aactcaggcg ctctgaccag cggcgtgcac accttcccag ctgtcctaca gtcctcagga | 900 |
| ctctactccc tcagcagcgt ggtgaccgtg ccctccagca cttcggcac ccagacctac | 960 |
| acctgcaacg tagatcacaa gcccagcaac accaaggtgg acaagacagt tggcggaggt | 1020 |
| ggctctgcgg ccgccgttcc acgtgatttg gaagttgttg cagcaactcc aactagtctg | 1080 |
| ctgatcagct gggatgcgcc gcatcatggt gttgcttatt atcgcattac gtacggcgaa | 1140 |
| accggcggca acagcccggt gcaggaattc acggtaccgg gcagcaaaag caccgcgacc | 1200 |
| atttccggac tgaaaccggg cgtggattat accattaacg tgtatgcggt gctggcttac | 1260 |
| ccgcgtggtt acccgctgag caaaccgatt agcattaatt atcggaccga ctacaaagac | 1320 |
| gatgacgaca agggcagttc tcaccatcac catcaccac | 1359 |

<210> SEQ ID NO 35
<211> LENGTH: 1023
<212> TYPE: DNA
<213> ORGANISM: Artificial Sequence
<220> FEATURE:
<223> OTHER INFORMATION: Synthetic polynucleotide

<400> SEQUENCE: 35

```
gaggtgcagc tggtggagtc tgggggaggc ctggtcaagc ctggggtgtc cctgagactc      60
tcctgtgcag cctctggatt caccttcagt agatatggca tgaactgggt ccgccaggct     120
ccagggaagg ggctggagtg ggtctcatcc attagtagta gtggtactta cataaagtac     180
gcagactcag tgaagggccg attcaccatc tccagagaca cgccaagaa ctcactgaat      240 ctgcaaatga acagcctgag agccgaggac acggctgtgt attattgtgc gagagatcgg     300
gaccggtatc cccttgacta ctggggccag ggaaccctgg tcactgtctc ctcaggaggc     360
ggcggttcag gcggaggtgg ctctgacatc cagatgaccc agtctccatc ctccctgtct     420
gcatctgtag gagacagagt caccatcact tgccgggcta gtcagagcat taacaactat     480
ttaaattggt atcagcagaa accagggaaa gcccctacgc tcctgatcta tgctgcatcc     540
agtttgcaaa gtgggtccc atcaaggttc agtggcagta gatctgggac agatttcact     600
ctcaccatca gcagtctgca acctgaagat tttgcagctt acttctgtca acagacttac     660
agtaacccga cgttcggcca agggaccaag gtggaagtca aacgaactgt ggctgcacca     720
tctgtcttca tcttcccgcc atctgatgag cagttgaaat ctggaactgc tagcgttgtg     780
tgcctgctga taacttcta tcccagagag gccaaagtac agtggaaggt ggataacgcc      840
ctccaatcgg gtaactccca ggagagtgtc acagagcagg acagcaagga cagcacctac     900
agcctcagca gcaccctgac gctgagcaaa gcagactacg agaaacacaa agtctacgcc     960
tgcgaagtca cccatcaggg cctgagctcg cccgtcacaa agagcttcaa cagggggagag    1020 tgt                                                                   1023

<210> SEQ ID NO 36
<211> LENGTH: 1356
<212> TYPE: DNA
<213> ORGANISM: Artificial Sequence
<220> FEATURE:
<223> OTHER INFORMATION: Synthetic polynucleotide

<400> SEQUENCE: 36
tcctatgagc tgacacagcc accctcggtg tcagtgtccc caggacaaac ggccaggatc       60
acctgctctg gagatgcatt gccaaaaaaa tatgcttatt ggtaccagca gaagtcaggc     120
caggcccctg tgctggtcat ctatgaggcc accaaacgac cctccgggat ccctgagaga     180
ttctctggct ccagctcagg gacaatggcc accttgactc tcagtggggc ccaggtggag     240
gatgaagctg actactactg ttactcaaca gacagcacta attatcattg ggtgttcggc     300
ggagggacca agctgaccgt cctaggcgga ggcggcggtt caggcggagg tggctctcag     360
gtgcagctgc aggagtcggg cccaggactg gtgaagcctt cacagaccct gtccctcacc     420
tgcactgtct ctggtggctc catcaacaat aataattact actggacctg gatccgccag     480
cacccaggga agggcctgga gtggattggg tacatctatt acagtgggag caccttctac     540
aacccgtccc tcaagagtcg agttaccata tcagtcgaca cgtctaagac ccagttctcc     600
ctgaagttga gctctgtgac tgccgcggac acggccgtgt attactgtgc gagagaggat     660
acgatgacgg gctggacgt ctggggccaa gggaccacgg tcaccgtctc ctcagctagc      720
accaagggcc catcggtctt ccccctggcg ccctgctcca ggagcacctc cgagagcaca     780
gcggccctgg gctgcctggt caaggactac ttccccgaac cggtgacggt gtcgtggaac     840
tcaggcgctc tgaccagcgg cgtgcacacc ttcccagctg tcctacagtc ctcaggactc     900
tactccctca gcagcgtggt gaccgtgccc tccagcaact tcggcaccca gacctacacc     960
```

| | |
|---|---|
| tgcaacgtag atcacaagcc cagcaacacc aaggtggaca agacagttgg cggaggtggc | 1020 |
| tctgcggccg ccgttccacg tgatttggaa gttgttgcag caactccaac tagtctgctg | 1080 |
| atcagctggg atgcgccgca tcatggtgtt gcttattatc gcattacgta cggcgaaacc | 1140 |
| ggcggcaaca gcccggtgca ggaattcacg gtacccggca gcaaaagcac cgcgaccatt | 1200 |
| tccggactga aaccgggcgt ggattatacc attaacgtgt atgcggtgct ggcttacccg | 1260 |
| cgtggttacc cgctgagcaa accgattagc attaattatc ggaccgacta caaagacgat | 1320 |
| gacgacaagg gcagttctca ccatcaccat caccac | 1356 |

<210> SEQ ID NO 37
<211> LENGTH: 1023
<212> TYPE: DNA
<213> ORGANISM: Artificial Sequence
<220> FEATURE:
<223> OTHER INFORMATION: Synthetic polynucleotide

<400> SEQUENCE: 37

| | |
|---|---|
| gacatccaga tgacccagtc tccatcctcc ctgtctgcat ctgtaggaga cagagtcacc | 60 |
| atcacttgcc gggctagtca gagcattaac aactatttaa attggtatca gcagaaacca | 120 |
| gggaaagccc ctacgctcct gatctatgct gcatccagtt tgcaaagtgg ggtcccatca | 180 |
| aggttcagtg gcagtagatc tgggacagat ttcactctca ccatcagcag tctgcaacct | 240 |
| gaagattttg cagcttactt ctgtcaacag acttacagta cccgacgtt cggccaaggg | 300 |
| accaaggtgg aagtcaaagg aggcggcggt tcaggcggag gtggctctga ggtgcagctg | 360 |
| gtggagtctg ggggaggcct ggtcaagcct ggggtgtccc tgagactctc ctgtgcagcc | 420 |
| tctggattca ccttcagtag atatagcatg aactgggtcc gccaggctcc agggaagggg | 480 |
| ctggagtggg tctcatccat tagtagtagt ggtacttaca taaagtacgc agactcagtg | 540 |
| aagggccgat tcaccatctc cagagacaac gccaagaact cactgaatct gcaaatgaac | 600 |
| agcctgagag ccgaggacac ggctgtgtat tattgtgcga gatcggga ccggtatccc | 660 |
| cttgactact ggggccaggg aaccctggtc actgtctcct cacgtacggt ggctgcacca | 720 |
| tctgtcttca tcttcccgcc atctgatgag cagttgaaat ctggaactgc ctctgttgtg | 780 |
| tgcctgctga ataacttcta tcccagagag gccaaagtac agtggaaggt ggataacgcc | 840 |
| ctccaatcgg gtaactccca ggagagtgtc acagagcagg acagcaagga cagcacctac | 900 |
| agcctcagca gcaccctgac gctgagcaaa gcagactacg agaaacacaa agtctacgcc | 960 |
| tgcgaagtca cccatcaggg cctgagctcg cccgtcacaa agagcttcaa caggggagag | 1020 |
| tgt | 1023 |

<210> SEQ ID NO 38
<211> LENGTH: 1749
<212> TYPE: DNA
<213> ORGANISM: Artificial Sequence
<220> FEATURE:
<223> OTHER INFORMATION: Synthetic polynucleotide

<400> SEQUENCE: 38

| | |
|---|---|
| gaggtgcagc tggtcgagtc tggaggagga ttggtgcagc ctggagggtc attgaaactc | 60 |
| tcatgtgcag cctctggatt caccttcaat agctacgcca tgaactgggt ccgccaggct | 120 |
| ccaggaaagg gtttggaatg ggttgctcgc ataagaagta aatataataa ttatgcaaca | 180 |
| tattatgccg attcagtgaa aggcaggttc accatctcca gagatgattc aaaaaacact | 240 |
| gcctatctac aaatgaacaa cttgaaaact gaggacactg ccgtgtacta ctgtgtgaga | 300 |

```
catgggaact tcggtaatag ctacgtttcc tggtgggctt actggggcca agggactctg      360
gtcaccgtct cctcaggagg cggcggttca ggcggaggtg gctctcagtc tgtgctgact      420
cagccaccct cggtgtctga agcccccagg cagagggtca ccatctcctg ttctggaagc      480
agctccaaca tcggaaataa tgctgtaaac tggtaccagc agctcccagg aaaggctccc      540
aaactcctca tctattatga tgatatgttg tcttcagggg tctcggaccg attttctggc      600
tccaagtctg gcacctcagc ctccctggcc atcagtgggc tccagtctga ggatgaggct      660
gattattact gtgcagcatg ggatgacagc ctgaatggtg tggtattcgg cggagggacc      720
aagctgaccg tcctagctag caccaagggc ccatcggtct tccccctggc gccctgctcc      780
aggagcacct ccgagagcac agcggccctg ggctgcctgg tcaaggacta cttccccgaa      840
ccggtgacgg tgtcgtggaa ctcaggcgct ctgaccagcg gcgtgcacac cttcccagct      900
gtcctacagt cctcaggact ctactccctc agcagcgtgg tgaccgtgcc ctccagcaac      960
ttcggcaccc agacctacac ctgcaacgta gatcacaagc ccagcaacac caaggtggac     1020
aagacagttg gcggaggtgg ctctgcggcc gcagagccca atcttctga caaaactcac     1080 acatgcccac cgtgcccagc acctgaagca gctgggggac cgtcagtctt cctcttcccc     1140
ccaaaaccca aggacaccct catgatctcc cggacccctg aggtcacatg cgtggtggtg     1200
gacgtgagcc acgaagaccc tgaggtcaag ttcaactggt acgtggacgg cgtggaggtg     1260
cataatgcca agacaaagcc gcgggaggag cagtacaaca gcacgtaccg tgtggtcagc     1320
gtcctcaccg tcctgcacca ggactggctg aatggcaagg agtacaagtg caaggtctcc     1380
aacaaagccc tcccagcccc catcgagaaa accatctcca aagccaaagg cagccccga     1440 gaaccacagg tgtacaccct gcccccatcc cgggaggaga tgaccaagaa ccaggtcagc     1500
ctgacctgcc tggtcaaagg cttctatccc agcgacatcg ccgtggagtg ggagagcaat     1560
gggcagccgg agaacaacta cgacaccacg cctcccgtgc tggactccga cggctccttc     1620
ttcctctata gcgacctcac cgtggacaag agcaggtggc agcaggggaa cgtcttctca     1680
tgctccgtga tgcatgaggc tctgcacaac cactacacgc agaagagcct ctccctgtct     1740
ccgggtaaa                                                            1749
```

<210> SEQ ID NO 39
<211> LENGTH: 1761
<212> TYPE: DNA
<213> ORGANISM: Artificial Sequence
<220> FEATURE:
<223> OTHER INFORMATION: Synthetic polynucleotide

<400> SEQUENCE: 39

```
caggtgcagc tgcaggagtc gggcccagga ctggtgaagc cttcacagac cctgtccctc       60
acctgcactg tctctggtgg ctccatcagc agtggtgctt actactggac ctggatccgc      120
cagcacccag ggaagggcct ggagtggatt gggtacatct attacagtgg gagcacctac      180
tacaacccgt ccctcaagag tcgagttagc atatcaatag acacgtctaa gaaccagttc      240
tccctgaagc tgagctctgt gactgccgcg gacacggccg tgtattactg tgcgcgaggc      300
agcagcagct ggttcgacta ctggggccag ggaaccctgg tcaccgtctc ctcaggaggc      360
ggcggttcag gcggaggtgg ctctcagact gttgtgactc aggaaccttc actcaccgta      420
tcacctggtg aacagtcac actcacttgt ggctcctcga ctgggggctgt acatctggc      480 aactacccaa actgggtcca acaaaaacca ggtcaggcac ccgtggtctt aataggtggg     540
```

-continued

```
actaagttcc tcgccccgg tactcctgcc agattctcag gctccctgct tggaggcaag    600
gctgccctca ccctctcagg ggtacagcca gaggatgagg cagaatatta ctgtgttcta    660
tggtacagca accgctgggt gttcggtgga ggaaccaaac tgactgtcct aggtcagccc    720
aaggctgccc cctcggtcac tctgttcccg ccctcctctg aggagcttca agccaacaag    780
gccacactgg tgtgtctcat aagtgacttc tacccgggag ccgtgacagt ggcctggaag    840
gcagatagca gccccgtcaa ggcgggagtg gagaccacca cccctccaa acaaagcaac    900 aacaagtacg cggccagcag ctatctgagc ctgacgcctg agcagtggaa gtcccacaga    960
agctacagct gccaggtcac gcatgaaggg agcaccgtgg agaagacagt ggcccctaca   1020
gaatgttcag cggccgcaga gcccaaatct tctgacaaaa ctcacacatg cccccgtgc   1080 ccagcacctg aagcagctgg ggaccgtca gtcttcctct tccccccaaa acccaaggac   1140
accctcatga tctcccggac ccctgaggtc acatgcgtgg tggtggacgt gagccacgaa   1200
gaccctgagg tcaagttcaa ctggtacgtg gacggcgtgg aggtgcataa tgccaagaca   1260
aagccgcgag aggagcagta caacagcacg taccgtgtg tcagcgtcct caccgtcctg   1320
caccaggact ggctgaatgg caaggagtac aagtgcaagg tctccaacaa agccctccca   1380
gcccccatcg agaaaaccat ctccaaagcc aaggggcagc cccgagaacc acaggtgtac   1440
accctgcccc catcccggaa ggagatgacc aagaaccagg tcagcctgac ctgcctggtc   1500
aaaggcttct atcccagcga catcgccgtg gagtgggaga gcaatgggca gccggagaac   1560
aactacaaga ccacgcctcc cgtgctgaag tccgacggct ccttcttcct ctatagcaag   1620
ctcaccgtgg acaagagcag gtggcagcag gggaacgtct tctcatgctc cgtgatgcat   1680
gaggctctgc acaaccacta cacgcagaag agcctctccc tgtctccggg taaagctgca   1740
gcgcatcacc accaccatca c                                            1761
```

<210> SEQ ID NO 40
<211> LENGTH: 186
<212> TYPE: PRT
<213> ORGANISM: Homo sapiens

<400> SEQUENCE: 40

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
    130                 135                 140

Ala Gly Ala Gly Gly Arg Gln Arg Gly Gln Asn Lys Glu Arg Pro Pro
145                 150                 155                 160

```
Pro Val Pro Asn Pro Asp Tyr Glu Pro Ile Arg Lys Gly Gln Arg Asp
                165                 170                 175

Leu Tyr Ser Gly Leu Asn Gln Arg Ile
            180                 185

<210> SEQ ID NO 41
<211> LENGTH: 177
<212> TYPE: PRT
<213> ORGANISM: Macaca fascicularis

<400> SEQUENCE: 41

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Gly Asp Ser
        35                  40                  45

Gly Asp Gln Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Ala Val Ala Thr Ile Val Ile Val Asp Ile Cys Ile Thr Leu
            100                 105                 110

Gly Leu Leu Leu Leu Val Tyr Tyr Trp Ser Lys Asn Arg Lys Ala Lys
        115                 120                 125

Ala Lys Pro Val Thr Arg Gly Ala Gly Ala Gly Gly Arg Gln Arg Gly
    130                 135                 140

Gln Asn Lys Glu Arg Pro Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 42
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 42

Glu Val Gln Leu Val Glu Ser Gly Gly Gly Leu Val Lys Pro Gly Val
1               5                   10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Thr Tyr Ile Lys Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Ala Arg Asp Arg Asp Arg Tyr Pro Leu Asp Tyr Trp Gly Gln Gly Thr
```

Leu Val Thr Val Ser Ser
            115

<210> SEQ ID NO 43
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 43

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Ala Thr Lys Arg Pro Ser Gly Ile Pro Glu Arg Phe Ser Gly Ser
    50                  55                  60

Ser Ser Gly Thr Met Ala Thr Leu Thr Leu Ser Gly Ala Gln Val Glu
65                  70                  75                  80

Asp Glu Ala Asp Tyr Tyr Cys Tyr Ser Thr Asp Ser Thr Asn Tyr His
                85                  90                  95

Trp Val Phe Gly Gly Gly Thr Lys Leu Thr Val Leu Gly
            100                 105

<210> SEQ ID NO 44
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 44

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser
        115                 120                 125

<210> SEQ ID NO 45
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 45

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 46
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 46

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 47

Glu Val Gln Leu Val Glu Ser Gly Gly Gly Leu Val Lys Pro Gly Val
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Gly Thr Tyr Ile Lys Tyr Ala Asp Ser Val
50                  55                  60

Lys Gly Arg Phe Thr Ile Ser Arg Asp Asn Ala Lys Asn Ser Leu Asn 65                  70                  75                  80
Leu Gln Met Asn Ser Leu Arg Ala Glu Asp Thr Ala Val Tyr Tyr Cys
                85                  90                  95

Ala Arg Asp Arg Asp Arg Tyr Pro Leu Asp Tyr Trp Gly Gln Gly Thr
                100                 105                 110

Leu Val Thr Val Ser Ser
        115

<210> SEQ ID NO 48
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
                20                  25                  30

Leu Asn Trp Tyr Gln Gln Lys Pro Gly Lys Ala Pro Thr Leu Leu Ile
            35                  40                  45

Tyr Ala Ala Ser Ser Leu Gln Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Arg
                100                 105

<210> SEQ ID NO 49
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 49

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
                20                  25                  30

Asn Tyr Tyr Trp Thr Trp Ile Arg Gln His Pro Gly Lys Gly Leu Glu
            35                  40                  45

Trp Ile Gly Tyr Ile Tyr Tyr Ser Gly Ser Thr Phe Tyr Asn Pro Ser
        50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
                100                 105                 110

Thr Thr Val Thr Val Ser Ser
        115

<210> SEQ ID NO 50
<211> LENGTH: 108

```
<212> TYPE: PRT
<213> ORGANISM: Artificial Sequence
<220> FEATURE:
<223> OTHER INFORMATION: Synthetic polypeptide

<400> SEQUENCE: 50

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Ala Phe Thr Leu Thr Ile Ser Ser Leu Gln Pro
65                  70                  75                  80

Glu Asp Phe Ala Thr Tyr Phe Cys Gln Gln Ala Asn Ser Phe Pro Leu
                85                  90                  95

Thr Phe Ala Gly Gly Thr Lys Val Asp Ile Lys Arg
            100                 105

<210> SEQ ID NO 51
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 51

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Pro Gly Asn Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Gln Lys Glu Trp Arg Leu Ile Phe Asp Tyr Trp Gly Gln
            100                 105                 110

Gly Thr Leu Val Thr Val Ser Ser
        115                 120

<210> SEQ ID NO 52
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 52

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
```

```
                35                  40                  45

Ile Tyr Tyr Asp Asp Met Leu Ser Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Val Val Phe Gly Gly Gly Thr Lys Leu Thr Val Leu
                100                 105                 110
```

<210> SEQ ID NO 53
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 53

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
                 20                  25                  30

Ala Tyr Tyr Trp Thr Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Ser Ile Ser Ile Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Ser Ser Ser Trp Phe Asp Tyr Trp Gly Gln Gly Thr
            100                 105                 110

Leu Val Thr Val Ser Ser
        115
```

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

```
Gly Gly Cys Val Phe Asn Met Phe Asn Cys Gly Gly
  1               5                  10
```

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide

<400> SEQUENCE: 55

```
Gly Gly Cys His Leu Pro Phe Ala Val Cys Gly Gly
  1               5                  10
```

<210> SEQ ID NO 56
<211> LENGTH: 12
<212> TYPE: PRT
<213> ORGANISM: Artificial Sequence

```
<220> FEATURE:
<223> OTHER INFORMATION: Synthetic peptide

<400> SEQUENCE: 56

Gly Gly Cys Gly His Glu Tyr Met Trp Cys Gly Gly
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

Gly Gly Cys Trp Pro Leu Gln Asp Tyr Cys Gly Gly
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic peptide

<400> SEQUENCE: 58

Gly Gly Cys Met Gln Met Asn Lys Trp Cys Gly Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic peptide

<400> SEQUENCE: 59

Gly Gly Cys Asp Gly Arg Thr Lys Tyr Cys Gly Gly
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide

<400> SEQUENCE: 60

Gly Gly Cys Ala Leu Tyr Pro Thr Asn Cys Gly Gly
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide

<400> SEQUENCE: 61

Gly Gly Cys Gly Lys His Trp His Gln Cys Gly Gly
1               5                   10

<210> SEQ ID NO 62
<211> LENGTH: 12
<212> TYPE: PRT
<213> ORGANISM: Artificial Sequence
<220> FEATURE:
```

```
<223> OTHER INFORMATION: Synthetic peptide

<400> SEQUENCE: 62

Gly Gly Cys His Ser Phe Lys His Phe Cys Gly Gly
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide

<400> SEQUENCE: 63

Gly Gly Cys Gln Gly Met Trp Thr Trp Cys Gly Gly
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic peptide

<400> SEQUENCE: 64

Gly Gly Cys Ala Gln Gln Trp His His Glu Tyr Cys Gly Gly
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic peptide

<400> SEQUENCE: 65

Gly Gly Cys Glu Arg Phe His His Ala Cys Gly Gly
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Thr Val Ala Ala Pro
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Ala Ser Thr Lys Gly Pro
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 68

Gly Gly Gly Gly Ser Gly Gly Gly Ser
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide

<400> SEQUENCE: 69

Gly Gly Gly Gly Ser Ala Ala Ala
1               5

<210> SEQ ID NO 70
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 71
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 71

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

```
<210> SEQ ID NO 72
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Arg
            100                 105

<210> SEQ ID NO 73
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 73

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide

<400> SEQUENCE: 74

Gly Gly Gly Gly Ser Gly Gly Gly Gly Ser Gly Gly Gly Gly Ser
1               5                   10                  15

<210> SEQ ID NO 75
<211> LENGTH: 518
```

<212> TYPE: PRT
<213> ORGANISM: Artificial Sequence
<220> FEATURE:
<223> OTHER INFORMATION: Synthetic polypeptide

<400> SEQUENCE: 75

```
Glu Val Gln Leu Leu Glu Gln Ser Gly Ala Glu Leu Val Arg Pro Gly
1               5                   10                  15

Ala Leu Val Lys Leu Ser Cys Lys Ala Ser Gly Phe Lys Ile Lys Asp
            20                  25                  30

Tyr Phe Val Asn Trp Val Lys Gln Arg Pro Glu Gln Gly Leu Glu Trp
        35                  40                  45

Ile Gly Trp Ile Asp Pro Glu Asn Asp Asn Ser Leu Tyr Gly Pro Asn
    50                  55                  60

Phe Gln Asp Lys Ala Ser Ile Thr Ala Asp Thr Ser Ser Asn Thr Gly
65                  70                  75                  80

Tyr Leu Gln Leu Ser Gly Leu Thr Ser Glu Asp Thr Ala Val Tyr Tyr
                85                  90                  95

Cys Ala Leu Tyr Tyr Gly Ser Arg Gly Asp Ala Met Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Glu Leu Val Met Thr Gln Thr Pro
    130                 135                 140

Ser Ser Leu Ser Ala Ser Leu Gly Asp Arg Val Thr Ile Ser Cys Arg
145                 150                 155                 160

Ala Ser Gln Asp Ile Ser Asn Tyr Leu Asn Trp Tyr Gln Gln Lys Pro
                165                 170                 175

Asp Gly Thr Val Lys Leu Leu Ile Tyr Tyr Thr Ser Arg Leu His Ser
            180                 185                 190

Gly Val Pro Ser Arg Phe Ser Gly Ser Gly Ser Gly Thr Asp Tyr Ser
        195                 200                 205

Leu Thr Ile Ser Asn Leu Glu Gln Glu Asp Ile Ala Thr Tyr Phe Cys
    210                 215                 220

Gln Gln Gly Asn Thr Leu Pro Leu Thr Phe Gly Ala Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Ser Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Gly Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Val Ser Trp Trp Ala Tyr Trp Gly Gln Gly Thr
        355                 360                 365

Leu Val Thr Val Ser Ser Gly Gly Gly Ser Gly Gly Gly Ser
    370                 375                 380
```

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Ala Ala Ala Asp Tyr Lys Asp Asp Asp Asp Lys Gly Ser Ser
            500                 505                 510

His His His His His His
        515

<210> SEQ ID NO 76
<211> LENGTH: 518
<212> TYPE: PRT
<213> ORGANISM: Artificial Sequence
<220> FEATURE:
<223> OTHER INFORMATION: Synthetic polypeptide

<400> SEQUENCE: 76

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Ser Ser Ser Trp Phe Asp Tyr Trp Gly Gln Gly Thr
        100                 105                 110

Leu Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Glu Ala Pro Arg Gln Arg Val Thr Ile Ser Cys Ser Gly Ser Ser Ser
145                 150                 155                 160

Asn Ile Gly Asn Asn Ala Val Asn Trp Tyr Gln Gln Leu Pro Gly Lys
            165                 170                 175

Ala Pro Lys Leu Leu Ile Tyr Tyr Asp Asp Met Leu Ser Ser Gly Val
        180                 185                 190

Ser Asp Arg Phe Ser Gly Ser Lys Ser Gly Thr Ser Ala Ser Leu Ala
        195                 200                 205

Ile Ser Gly Leu Gln Ser Glu Asp Glu Ala Asp Tyr Tyr Cys Ala Ala
    210                 215                 220

```
Trp Asp Asp Ser Leu Asn Gly Val Val Phe Gly Gly Gly Thr Lys Leu
225                 230                 235                 240

Thr Val Leu Ser Gly Gly Gly Ser Glu Val Gln Leu Val Glu Ser
        245                 250                 255

Gly Gly Gly Leu Val Gln Pro Gly Gly Ser Leu Lys Leu Ser Cys Ala
            260                 265                 270

Ala Ser Gly Phe Thr Phe Asn Ser Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Gly Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Val Ser Trp Trp Ala Tyr Trp Gly Gln Gly Thr
        355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Ala Ala Ala Asp Tyr Lys Asp Asp Asp Asp Lys Gly Ser Ser
            500                 505                 510

His His His His His His
        515

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(9)
<223> OTHER INFORMATION: Any amino acid

<400> SEQUENCE: 77

Cys Xaa Xaa Xaa Xaa Xaa Xaa Xaa Xaa
1               5

<210> SEQ ID NO 78
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 78

Leu Glu Trp Ile Gly
1               5

<210> SEQ ID NO 79
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Any amino acid

<400> SEQUENCE: 79

Trp Gly Xaa Gly
1

<210> SEQ ID NO 80
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Any amino acid

<400> SEQUENCE: 80

Phe Gly Xaa Gly
1

<210> SEQ ID NO 81
<211> LENGTH: 5
<212> TYPE: PRT
<213> ORGANISM: Artificial Sequence
<220> FEATURE:
<223> OTHER INFORMATION: Synthetic peptide

<400> SEQUENCE: 81

Gln Asp Gly Asn Glu
1               5

<210> SEQ ID NO 82
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 82

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80
```

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 83
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 83

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 84
<211> LENGTH: 581
<212> TYPE: PRT
<213> ORGANISM: Artificial Sequence
<220> FEATURE:
<223> OTHER INFORMATION: Synthetic polypeptide

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Ser Ser Trp Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gln Thr Val Val Thr Gln Glu Pro Ser Leu Thr Val Ser Pro Gly Gly
    130                 135                 140

Thr Val Thr Leu Thr Cys Gly Ser Ser Thr Gly Ala Val Thr Ser Gly

```
            145                 150                 155                 160
Asn Tyr Pro Asn Trp Val Gln Gln Lys Pro Gly Gln Ala Pro Arg Gly
                165                 170                 175

Leu Ile Gly Gly Thr Lys Phe Leu Ala Pro Gly Thr Pro Ala Arg Phe
                180                 185                 190

Ser Gly Ser Leu Leu Gly Gly Lys Ala Ala Leu Thr Leu Ser Gly Val
                195                 200                 205

Gln Pro Glu Asp Glu Ala Glu Tyr Tyr Cys Val Leu Trp Tyr Ser Asn
        210                 215                 220

Arg Trp Val Phe Gly Gly Gly Thr Lys Leu Thr Val Leu Gly Gln Pro
225                 230                 235                 240

Lys Ala Ala Pro Ser Val Thr Leu Phe Pro Pro Ser Ser Glu Glu Leu
                245                 250                 255

Gln Ala Asn Lys Ala Thr Leu Val Cys Leu Ile Ser Asp Phe Tyr Pro
                260                 265                 270

Gly Ala Val Thr Val Ala Trp Lys Ala Asp Ser Ser Pro Val Lys Ala
                275                 280                 285

Gly Val Glu Thr Thr Thr Pro Ser Lys Gln Ser Asn Asn Lys Tyr Ala
        290                 295                 300

Ala Ser Ser Tyr Leu Ser Leu Thr Pro Glu Gln Trp Lys Ser His Arg
305                 310                 315                 320

Ser Tyr Ser Cys Gln Val Thr His Glu Gly Ser Thr Val Glu Lys Thr
                325                 330                 335

Val Ala Pro Thr Glu Cys Ser Glu Pro Lys Ser Ser Asp Lys Thr His
                340                 345                 350

Thr Cys Pro Pro Cys Pro Ala Pro Glu Ala Ala Gly Gly Pro Ser Val
                355                 360                 365

Phe Leu Phe Pro Pro Lys Pro Lys Asp Thr Leu Met Ile Ser Arg Thr
        370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
                420                 425                 430

Val Leu Thr Val Leu His Gln Asp Trp Leu Asn Gly Lys Glu Tyr Lys
                435                 440                 445

Cys Lys Val Ser Asn Lys Ala Leu Pro Ala Pro Ile Glu Lys Thr Ile
        450                 455                 460

Ser Lys Ala Lys Gly Gln Pro Arg Glu Pro Gln Val Tyr Thr Leu Pro
465                 470                 475                 480

Pro Ser Arg Lys Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Lys Ser
        515                 520                 525

Asp Gly Ser Phe Phe Leu Tyr Ser Lys Leu Thr Val Asp Lys Ser Arg
                530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys His
                565                 570                 575
```

His His His His His
          580

<210> SEQ ID NO 85
<211> LENGTH: 1746
<212> TYPE: DNA
<213> ORGANISM: Artificial Sequence
<220> FEATURE:
<223> OTHER INFORMATION: Synthetic polynucleotide

<400> SEQUENCE: 85

| | | | | |
|---|---|---|---|---|
| caggtgcagc tgcaggagtc gggcccagga ctggtgaagc cttcacagac cctgtccctc | 60 |
| acctgcactg tctctggtgg ctccatcagc agtggtgctt actactggac ctggatccgc | 120 |
| cagcacccag ggaagggcct ggagtggatt gggtacatct attacagtgg gagcacctac | 180 |
| tacaacccgt ccctcaagag tcgagttagc atatcaatag acacgtctaa gaaccagttc | 240 |
| tccctgaagc tgagctctgt gactgccgcg gacacggccg tgtattactg tgcgcgaggc | 300 |
| agcagcagct ggttcgacta ctggggccag ggaaccctgg tcaccgtctc ctcaggaggc | 360 |
| ggcggttcag gcggaggtgg ctctcagacc gtggtcaccc aggaaccttc tctgaccgtc | 420 |
| agtcccggcg aaccgtgac cctgacctgt ggctcctcta ccggcgctgt gacctccggc | 480 |
| aactacccta ctgggtgca gcagaaaccc ggccaggctc cagaggact catcggcggc | 540 |
| accaagtttc tggcccctgg caccctgcc agattctctg ctccctgct gggcggcaag | 600 |
| gctgctctga ccctgagcgg agtccagcca gaggacgagg ccgagtacta ctgtgtgctg | 660 |
| tggtactcca cagatgggt gttcggcggt ggcaccaagc tgaccgtgct gggtcagccc | 720 |
| aaggctgccc cctcggtcac tctgttcccg ccctcctctg aggagcttca agccaacaag | 780 |
| gccacactgg tgtgtctcat aagtgacttc tacccgggag ccgtgacagt ggcctggaag | 840 |
| gcagatagca gccccgtcaa ggcgggagtg gagaccacca cccctccaa acaaagcaac | 900 |
| aacaagtacg cggccagcag ctatctgagc ctgacgcctg agcagtggaa gtcccacaga | 960 |
| agctacagct gccaggtcac gcatgaaggg agcaccgtgg agaagacagt ggcccctaca | 1020 |
| gaatgttcag gcccaaatc ttctgacaaa actcacacat gcccccgtg cccagcacct | 1080 |
| gaagcagctg ggggaccgtc agtcttcctc ttccccccaa acccaagga caccctcatg | 1140 |
| atctcccgga cccctgaggt cacatgcgtg gtggtggacg tgagccacga agaccctgag | 1200 |
| gtcaagttca actggtacgt ggacggcgtg gaggtgcata atgccaagac aaagccgcga | 1260 |
| gaggagcagt acaacagcac gtaccgtgtg gtcagcgtcc tcaccgtcct gcaccaggac | 1320 |
| tggctgaatg gcaaggagta caagtgcaag gtctccaaca aagccctccc agcccccatc | 1380 |
| gagaaaacca tctccaaagc caagggcag ccccgagaac acaggtgta cccctgccc | 1440 |
| ccatcccgga aggagatgac caagaaccag gtcagcctga cctgcctggt caaaggcttc | 1500 |
| tatcccagcg acatcgccgt ggagtgggag agcaatgggc agccggagaa caactacaag | 1560 |
| accacgcctc ccgtgctgaa gtccgacggc tccttcttcc tctatagcaa gctcaccgtg | 1620 |
| gacaagagca ggtggcagca ggggaacgtc ttctcatgct ccgtgatgca tgaggctctg | 1680 |
| cacaaccact acacgcagaa gagcctctcc ctgtctccgg gtaaacatca ccaccaccat | 1740 |
| cactag | 1746 |

<210> SEQ ID NO 86
<211> LENGTH: 575
<212> TYPE: PRT
<213> ORGANISM: Artificial Sequence
<220> FEATURE:
<223> OTHER INFORMATION: Synthetic polypeptide

<400> SEQUENCE: 86

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gln Ser Val Leu Thr Gln Pro Pro Ser
    130                 135                 140

Val Ser Glu Ala Pro Arg Gln Arg Val Thr Ile Ser Cys Ser Gly Ser
145                 150                 155                 160

Ser Ser Asn Ile Gly Asn Asn Ala Val Asn Trp Tyr Gln Gln Leu Pro
                165                 170                 175

Gly Lys Ala Pro Lys Leu Leu Ile Tyr Tyr Asp Asp Met Leu Ser Ser
            180                 185                 190

Gly Val Ser Asp Arg Phe Ser Gly Ser Lys Ser Gly Thr Ser Ala Ser
        195                 200                 205

Leu Ala Ile Ser Gly Leu Gln Ser Glu Asp Glu Ala Asp Tyr Tyr Cys
    210                 215                 220

Ala Ala Trp Asp Asp Ser Leu Asn Gly Val Val Phe Gly Gly Gly Thr
225                 230                 235                 240

Lys Leu Thr Val Leu Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Asn
305                 310                 315                 320

Phe Gly Thr Gln Thr Tyr Thr Cys Asn Val Asp His Lys Pro Ser Asn
                325                 330                 335

Thr Lys Val Asp Lys Thr Val Glu Pro Lys Ser Ser Asp Lys Thr His
            340                 345                 350

Thr Cys Pro Pro Cys Pro Ala Pro Glu Ala Ala Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser His Glu Asp Pro Glu
385                 390                 395                 400
```

```
Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Asp Thr Thr Pro Pro Val Leu Asp Ser
        515                 520                 525

Asp Gly Ser Phe Phe Leu Tyr Ser Asp Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 87
<211> LENGTH: 1728
<212> TYPE: DNA
<213> ORGANISM: Artificial Sequence
<220> FEATURE:
<223> OTHER INFORMATION: Synthetic polynucleotide

<400> SEQUENCE: 87
gaagtgcagc tcgtggagag tggcggagga ctggtgcagc caggcggctc cctgaagctg      60
tcttgcgccg ccagcggctt caccttcaat aagtacgcta tgaattgggt ccggcaggca     120
cctggaaaag ggctcgaatg ggtcgcaagg attaggtcta agtacaacaa ctacgccacc     180
tattacgccg actctgtgaa ggaccggttc accatctccc gggacgactc taagaacacc     240
gcttacctgc agatgaacaa cctgaaaacc gaggataccg ctgtgtacta ttgtgtgcgg     300
cacggcaact cggcaactc ctacatctcc tactgggcct attggggaca gggcacactg     360
gtcaccgtgt cctctggagg cggcggatcc ggcggaggtg gctctcagtc tgtgctgact     420
cagccaccct cggtgtctga agccccagg cagagggtca ccatctcctg ttctggaagc     480
agctccaaca tcggaaataa tgctgtaaac tggtaccagc agctcccagg aaaggctccc     540
aaactcctca tctattatga tgatatgttg tcttcagggg tctcggaccg attttctggc     600
tccaagtctg gcacctcagc ctccctggcc atcagtgggc tccagtctga ggatgaggct     660
gattattact gtgcagcatg ggatgacagc ctgaatggtg tggtattcgg cggagggacc     720
aagctgaccg tcctagctag caccaagggc ccatcggtct tccccctggc gcctgctcc      780 aggagcacct ccgagagcac agcggccctg ggctgcctgg tcaaggacta cttccccgaa     840
ccggtgacgg tgtcgtggaa ctcaggcgct ctgaccagcg gcgtgcacac cttcccagct     900
gtcctacagt cctcaggact ctactccctc agcagcgtgg tgaccgtgcc ctccagcaac     960
ttcggcaccc agacctacac ctgcaacgta gatcacaagc ccagcaacac caaggtggac    1020
aagacagttg agcccaaatc ttctgacaaa actcacacat gcccaccgtg cccagcacct    1080
```

-continued

```
gaagcagctg ggggaccgtc agtcttcctc ttccccccaa acccaagga caccctcatg   1140 atctcccgga cccctgaggt cacatgcgtg gtggtggacg tgagccacga agaccctgag   1200
gtcaagttca actggtacgt ggacggcgtg gaggtgcata atgccaagac aaagccgcgg   1260
gaggagcagt acaacagcac gtaccgtgtg gtcagcgtcc tcaccgtcct gcaccaggac   1320
tggctgaatg gcaaggagta caagtgcaag gtctccaaca agccctccc agccccatc   1380 gagaaaacca tctccaaagc caagggcag ccccgagaac acaggtgta caccctgccc   1440 ccatcccggg aggagatgac caagaaccag gtcagcctga cctgcctggt caaaggcttc   1500
tatcccagcg acatcgccgt ggagtgggag agcaatgggc agccggagaa caactacgac   1560
accacgcctc ccgtgctgga ctccgacggc tccttcttcc tctatagcga cctcaccgtg   1620
gacaagagca ggtggcagca ggggaacgtc ttctcatgct ccgtgatgca tgaggctctg   1680
cacaaccact acacgcagaa gagcctctcc ctgtctccgg gtaaatga                1728
```

<210> SEQ ID NO 88
<211> LENGTH: 504
<212> TYPE: PRT
<213> ORGANISM: Artificial Sequence
<220> FEATURE:
<223> OTHER INFORMATION: Synthetic polypeptide

<400> SEQUENCE: 88

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Ser Ser Trp Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Glu Ala Pro Arg Gln Arg Val Thr Ile Ser Cys Ser Gly Ser Ser Ser
145                 150                 155                 160

Asn Ile Gly Asn Asn Ala Val Asn Trp Tyr Gln Gln Leu Pro Gly Lys
                165                 170                 175

Ala Pro Lys Leu Leu Ile Tyr Tyr Asp Asp Met Leu Ser Ser Gly Val
            180                 185                 190

Ser Asp Arg Phe Ser Gly Ser Lys Ser Gly Thr Ser Ala Ser Leu Ala
        195                 200                 205

Ile Ser Gly Leu Gln Ser Glu Asp Glu Ala Asp Tyr Tyr Cys Ala Ala
    210                 215                 220

Trp Asp Asp Ser Leu Asn Gly Val Val Phe Gly Gly Thr Lys Leu
225                 230                 235                 240

Thr Val Leu Ser Gly Gly Gly Gly Ser Glu Val Gln Leu Val Glu Ser
```

```
                245                 250                 255
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu His His His His His His
            500

<210> SEQ ID NO 89
<211> LENGTH: 1515
<212> TYPE: DNA
<213> ORGANISM: Artificial Sequence
<220> FEATURE:
<223> OTHER INFORMATION: Synthetic polynucleotide

<400> SEQUENCE: 89
caggtgcagc tgcaggagtc gggcccagga ctggtgaagc cttcacagac cctgtccctc      60
acctgcactg tctctggtgg ctccatcagc agtggtgctt actactggac ctggatccgc     120
cagcacccag ggaagggcct ggagtggatt gggtacatct attacagtgg gagcacctac     180
tacaacccgt ccctcaagag tcgagttagc atatcaatag acacgtctaa gaaccagttc     240
tccctgaagc tgagctctgt gactgccgcg gacacggccg tgtattactg cgcgaggc      300 agcagcagct ggttcgacta ctggggccag gaaccctgg tcaccgtctc ctcaggaggc     360
ggcggttcag gcggaggtgg ctctggcggt ggcggaagtc agtctgtgct gactcagcca     420
ccctcggtgt ctgaagcccc caggcagagg gtcaccatct cctgttctgg aagcagctcc     480
aacatcggaa ataatgctgt aaactggtac cagcagctcc caggaaaggc tcccaaactc     540
ctcatctatt atgatgatat gttgtcttca ggggtctcgg accgattttc tggctccaag     600
```

```
tctggcacct cagcctccct ggccatcagt gggctccagt ctgaggatga ggctgattat    660
tactgtgcag catgggatga cagcctgaat ggtgtggtat tcggcggagg gaccaagctg    720
accgtcctat ccggaggtgg tggatccgaa gtgcagctcg tggagagtgg cggaggactg    780
gtgcagccag gcggctccct gaagctgtct tgcgccgcca gcggcttcac cttcaataag    840
tacgctatga attgggtccg gcaggcacct ggaaaagggc tcgaatgggt cgcaaggatt    900
aggtctaagt acaacaacta cgccacctat tacgccgact ctgtgaagga ccggttcacc    960
atctcccggg acgactctaa gaacaccgct tacctgcaga tgaacaacct gaaaaccgag   1020
gataccgctg tgtactattg tgtgcggcac ggcaacttcg gcaactccta catctcctac   1080
tgggcctatt ggggacaggg cacactggtc accgtgtcct ctggcggtgg aggatctggt   1140
ggcggcggat ctggcggcgg aggttcccag accgtggtca cccaggaacc ttctctgacc   1200
gtcagtcccg gcggaaccgt gaccctgacc tgtggctcct ctaccggcgc tgtgacctcc   1260
ggcaactacc ctaactgggt gcagcagaaa cccggccagg ctcccagagg actcatcggc   1320
ggcaccaagt ttctggcccc tggcaccccgt gccagattct ctggctccct gctgggcggc   1380
```

```
aaggctgctc tgaccctgag cggagtccag ccagaggacg aggccgagta ctactgtgtg   1440
ctgtggtact ccaacagatg ggtgttcggc ggtggcacca agctgaccgt gctgcatcac   1500
caccaccatc actga                                                    1515
```

<210> SEQ ID NO 90
<211> LENGTH: 508
<212> TYPE: PRT
<213> ORGANISM: Artificial Sequence
<220> FEATURE:
<223> OTHER INFORMATION: Synthetic polypeptide

<400> SEQUENCE: 90

```
Val Leu Thr Gln Thr Pro Ser Pro Val Ser Ala Ala Val Gly Gly Thr
1               5                   10                  15

Val Thr Ile Asn Cys Gln Ser Ser Pro Ser Leu Ile Tyr Asp Ser Arg
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Gln Phe Thr Leu Thr Ile Ser Asp Val Gln Ser
65                  70                  75                  80

Asp Asp Ala Ala Thr Tyr Tyr Cys Gln Ser His Asp Thr Asn Pro Gly
                85                  90                  95

Ser Ser Thr Tyr Gly Ala Pro Phe Gly Gly Gly Thr Glu Val Val Val
            100                 105                 110

Gln Gly Gly Gly Ser Gly Gly Gly Ser Ser Gly Gly Gly Ser
        115                 120                 125

Glu Val Gln Leu Met Glu Ser Gly Gly Gly Leu Val Lys Pro Glu Gly
    130                 135                 140

Ser Leu Thr Leu Thr Cys Lys Val Ser Gly Phe Ser Phe Ser Thr Ser
145                 150                 155                 160

Ala Ile Ser Trp Val Arg Gln Ala Pro Gly Lys Arg Pro Glu Trp Ile
                165                 170                 175

Ala Gly Ile Tyr Asn Gly Gly Ser Thr Tyr Tyr Ala Ser Trp Val
            180                 185                 190
```

Asn Gly Arg Phe Ser Ile Ser Arg Ser Thr Ser Leu Asn Thr Val Thr
            195                 200                 205

Leu Gln Met Thr Arg Leu Thr Ala Ala Asp Thr Ala Thr Tyr Phe Cys
        210                 215                 220

Ala Arg Trp Ile Arg Ile His Tyr Ser Phe Asp Leu Trp Pro Gly
225                 230                 235                 240

Thr Leu Val Thr Val Ser Ser Gly Gly Gly Ser Glu Val Gln
                245                 250                 255

Leu Val Glu Ser Gly Gly Gly Leu Val Gln Pro Gly Gly Ser Leu Lys
                260                 265                 270

Leu Ser Cys Ala Ala Ser Gly Phe Thr Phe Asn Lys Tyr Ala Met Asn
        275                 280                 285

Trp Val Arg Gln Ala Pro Gly Lys Gly Leu Glu Trp Val Ala Arg Ile
        290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Ile Ser Tyr Trp Ala Tyr Trp
        355                 360                 365

Gly Gln Gly Thr Leu Val Thr Val Ser Ser Gly Gly Gly Gly Ser Gly
        370                 375                 380

Gly Gly Ser Gly Gly Gly Gly Ser Gln Thr Val Thr Gln Glu
385                 390                 395                 400

Pro Ser Leu Thr Val Ser Pro Gly Gly Thr Val Thr Leu Thr Cys Gly
                405                 410                 415

Ser Ser Thr Gly Ala Val Thr Ser Gly Asn Tyr Pro Asn Trp Val Gln
            420                 425                 430

Gln Lys Pro Gly Gln Ala Pro Arg Gly Leu Ile Gly Gly Thr Lys Phe
        435                 440                 445

Leu Ala Pro Gly Thr Pro Ala Arg Phe Ser Gly Ser Leu Leu Gly Gly
450                 455                 460

Lys Ala Ala Leu Thr Leu Ser Gly Val Gln Pro Glu Asp Glu Ala Glu
465                 470                 475                 480

Tyr Tyr Cys Val Leu Trp Tyr Ser Asn Arg Trp Val Phe Gly Gly Gly
                485                 490                 495

Thr Lys Leu Thr Val Leu His His His His His
            500                 505

<210> SEQ ID NO 91
<211> LENGTH: 1527
<212> TYPE: DNA
<213> ORGANISM: Artificial Sequence
<220> FEATURE:
<223> OTHER INFORMATION: Synthetic polynucleotide

<400> SEQUENCE: 91
gtcctcactc agacccttc tccggtctcc gcggccgtcg gcggaactgt cactatcaat      60
tgccagagtt ccccaagtct gatctatgac agtagattag cctggtatca gcaaaaacca    120
gggcaaccac ctaagctcct gatctataaa gcatccactt tggccagtgg ggtcccatca    180
aggttcagcg gcagtggatc tgggacacag ttcactctca caatcagcga cgtccagtct    240
gacgatgccg caacttatta ctgtcaaagt catgacacta tcctgggtc tagtacttat    300

```
ggcgccccat tcggaggagg cactgaagtc gtagtccagg gtggtggtgg ttctggcggc       360
ggcggctcca gtggtggtgg ttctgaggtg cagctgatgg agtctggggg aggcttggta       420
aagcccgagg ggtccctgac cctcacctgc aaggtctctg gattctcctt ttcaacgagt       480
gccattagct gggtccgcca ggctccaggg aagagaccag agtggatcgc cgggatttat       540
aacggaggtg gtagcacata ctacgcatcc tgggtgaacg gccggttcag catctccaga       600
tccacgtcct tgaacacggt gacgctgcaa atgaccagac tgacggccgc tgacacggcc       660
acatatttct gtgcgagatg gattcggatc cattattcct tcgacctgtg gggacctggc       720
acgttggtca ccgtctcctc atccggaggt ggtggctccg aggtgcagct ggtcgagtct       780
ggaggaggat tggtgcagcc tggagggtca ttgaaactct catgtgcagc ctctggattc       840
accttcaata gtacgccat gaactgggtc cgccaggctc caggaaaggg tttggaatgg       900
gttgctcgca taagaagtaa atataataat tatgcaacat attatgccga ttcagtgaaa       960
gacaggttca ccatctccag agatgattca aaaaacactg cctatctaca aatgaacaac      1020
ttgaaaactg aggacactgc cgtgtactac tgtgtgagac atgggaactt cggtaatagc      1080
tacatatcct actgggctta ctggggccaa gggactctgg tcaccgtctc ctcaggtggt      1140
ggtggttctg gcggcggcgg ctccggtggt ggtggttctc agactgttgt gactcaggaa      1200
ccttcactca ccgtatcacc tggtggaaca gtcacactca cttgtggctc ctcgactggg      1260
gctgttacat ctggcaacta cccaaactgg gtccaacaaa aaccaggtca ggcaccccgt      1320
ggtctaatag gtgggactaa gttcctcgcc cccggtactc ctgccagatt ctcaggctcc      1380
ctgcttggag gcaaggctgc cctcacgctc tcaggggtac agccagagga tgaggcagaa      1440
tattactgtg ttctatggta cagcaaccgc tgggtgttcg gtggaggaac caaactgact      1500
gtcctacatc atcaccatca tcattag                                          1527
```

<210> SEQ ID NO 92
<211> LENGTH: 525
<212> TYPE: PRT
<213> ORGANISM: Artificial Sequence
<220> FEATURE:
<223> OTHER INFORMATION: Synthetic polypeptide

<400> SEQUENCE: 92

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140
```

Pro Asp Ser Leu Thr Val Ser Leu Gly Glu Arg Thr Ile Asn Cys
145                 150                 155                 160

Lys Ser Ser Gln Ser Val Leu Asp Ser Ser Lys Asn Lys Asn Ser Leu
            165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Ser Tyr
        275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Val Ser Trp Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu Ala Ala Ala Asp Tyr Lys Asp
            500                 505                 510

Asp Asp Asp Lys Gly Ser Ser His His His His His
            515                 520                 525

<210> SEQ ID NO 93
<211> LENGTH: 1575
<212> TYPE: DNA
<213> ORGANISM: Artificial Sequence
<220> FEATURE:

<223> OTHER INFORMATION: Synthetic polynucleotide

<400> SEQUENCE: 93

```
caggtgcagc tggtgcagtc tggagctgag gtgaagaagc ctggagcgtc agtcaaggtc      60
tcctgcaagg ctagcgggta taccttcaca aactatggaa tgaactgggt gaagcaggct     120
ccaggacagg gtttaaagtg gatgggctgg ataaacacct acactggaga gccaacatat     180
gctgatgact tcaagggacg ggttaccatg acttcggata cctctaccag cactgcctat     240
ttggaactcc acaacctcag aagtgatgac acggctgtat attactgtgc gcgctggagt     300
tggagtgatg gttactacgt ttactttgac tactggggcc aaggcactac ggtcaccgtc     360
tcctcaggtg gtggtggttc tggcggcggc ggctccggtg gtggtggttc tgacatcgtg     420
atgacacagt ctccagactc cctgactgtg tctctgggcg agaggaccac catcaactgc     480
aagtccagcc agagtgtttt agacagctcc aagaataaga actccttagc ttggtaccag     540
cagaaaccag gacagcctcc taaattactc ctttcctggg catctacgcg ggaatccggg     600
atccctgacc gattcagtgg cagcgggtct ggacagatt tcactctcac tattgacagc      660
ctgcagcctg aagattctgc aacttactat tgtcaacagt ctgcccactt cccgatcacc     720
tttggccaag gacacgact ggagattaaa tccggaggtg gtggatccga ggtgcagctg      780
gtcgagtctg gaggaggatt ggtgcagcct ggagggtcat tgaaactctc atgtgcagcc     840
tctggattca ccttcaatag ctacgccatg aactgggtcc gccaggctcc aggaaagggt     900
ttggaatggg ttgctcgcat aagaagtaaa tataataatt atgcaacata ttatgccgat     960
tcagtgaaag gcaggttcac catctccaga gatgattcaa aaaacactgc ctatctacaa    1020
atgaacaact tgaaaactga ggacactgcc gtgtactact gtgtgagaca tgggaacttc    1080
ggtaatagct acgtttcctg gtgggcttac tggggccaag ggactctggt caccgtctcc    1140
tcaggtggtg gtggttctgg cggcggcggc tccggtggtg gtggttctca gactgttgtg    1200
actcaggaac cttcactcac cgtatcacct ggtggaacag tcacactcac ttgtggctcc    1260
tcgactgggg ctgttacatc tggcaactac ccaaactggg tccaacaaaa accaggtcag    1320
gcacccgtg gtctaatagg tgggactaag ttcctcgccc ccggtactcc tgccagattc     1380
tcaggctccc tgcttggagg caaggctgcc ctcaccctct caggggtaca gccagaggat    1440
gaggcagaat attactgtgt tctatggtac agcaaccgct gggtgttcgg tggaggaacc    1500
aaactgactg tcctagcggc cgcagactac aaagacgatg acgacaaggg cagttctcac    1560
catcaccatc accac                                                    1575
```

<210> SEQ ID NO 94
<211> LENGTH: 578
<212> TYPE: PRT
<213> ORGANISM: Artificial Sequence
<220> FEATURE:
<223> OTHER INFORMATION: Synthetic polypeptide

<400> SEQUENCE: 94

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

-continued

```
Ser Val Lys Asp Arg Phe Thr Ile Ser Arg Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Asp Ile Val Met Thr Gln Ser Pro Asp
    130                 135                 140

Ser Leu Thr Val Ser Leu Gly Glu Arg Thr Thr Ile Asn Cys Lys Ser
145                 150                 155                 160

Ser Gln Ser Val Leu Asp Ser Ser Thr Asn Lys Asn Ser Leu Ala Trp
                165                 170                 175

Tyr Gln Gln Lys Pro Gly Gln Pro Pro Lys Leu Leu Leu Ser Trp Ala
            180                 185                 190

Ser Thr Arg Glu Ser Gly Ile Pro Asp Arg Phe Ser Gly Ser Gly Ser
    195                 200                 205

Gly Thr Asp Phe Thr Leu Thr Ile Asp Ser Pro Gln Pro Glu Asp Ser
210                 215                 220

Ala Thr Tyr Tyr Cys Gln Gln Ser Ala His Phe Pro Ile Thr Phe Gly
225                 230                 235                 240

Gln Gly Thr Arg Leu Glu Ile Lys Ala Ser Thr Lys Gly Pro Ser Val
                245                 250                 255

Phe Pro Leu Ala Pro Cys Ser Arg Ser Thr Ser Glu Ser Thr Ala Ala
            260                 265                 270

Leu Gly Cys Leu Val Lys Asp Tyr Phe Pro Glu Pro Val Thr Val Ser
    275                 280                 285

Trp Asn Ser Gly Ala Leu Thr Ser Gly Val His Thr Phe Pro Ala Val
290                 295                 300

Leu Gln Ser Ser Gly Leu Tyr Ser Leu Ser Ser Val Val Thr Val Pro
305                 310                 315                 320

Ser Ser Asn Phe Gly Thr Gln Thr Tyr Thr Cys Asn Val Asp His Lys
                325                 330                 335

Pro Ser Asn Thr Lys Val Asp Lys Thr Val Glu Pro Lys Ser Ser Asp
            340                 345                 350

Lys Thr His Thr Cys Pro Pro Cys Pro Ala Pro Glu Ala Ala Gly Gly
    355                 360                 365

Pro Ser Val Phe Leu Phe Pro Pro Lys Pro Lys Asp Thr Leu Met Ile
370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
    435                 440                 445

Glu Tyr Lys Cys Lys Val Ser Asn Lys Ala Leu Pro Ala Pro Ile Glu
    450                 455                 460

Lys Thr Ile Ser Lys Ala Lys Gly Gln Pro Arg Glu Pro Gln Val Tyr
465                 470                 475                 480
```

```
Thr Leu Pro Pro Ser Arg Glu Glu Met Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Asp Thr Thr Pro Pro Val
        515                 520                 525

Leu Asp Ser Asp Gly Ser Phe Phe Leu Tyr Ser Asp Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 95
<211> LENGTH: 1737
<212> TYPE: DNA
<213> ORGANISM: Artificial Sequence
<220> FEATURE:
<223> OTHER INFORMATION: Synthetic polynucleotide

<400> SEQUENCE: 95
gaagtgcagc tcgtggagag tggcggagga ctggtgcagc caggcggctc cctgaagctg      60
tcttgcgccg ccagcggctt caccttcaat aagtacgcta tgaattgggt ccggcaggca     120
cctggaaaag ggctcgaatg ggtcgcaagg attaggtcta agtacaacaa ctacgccacc     180
tattacgccg actctgtgaa ggaccggttc accatctccc gggacgactc taagaacacc     240
gcttacctgc agatgaacaa cctgaaaacc gaggataccg ctgtgtacta ttgtgtgcgg     300
cacggcaact cggcaactc ctacatctcc tactgggcct attggggaca gggcacactg      360
gtcaccgtgt cctctggagg cggcggttca ggcggaggtg gctctgacat cgtgatgacc     420
cagtcccccg actccctgac cgtgtccctg ggcgagcgga ccaccatcaa ctgcaagtcc     480
tcccagtccg tgctggactc ctccaccaac aagaactccc tggcctggta tcagcagaag     540
cctggccagc ctcctaagct gctgctctct gggcttcca ccagagagag cgggattccc      600
gataggttct ccggctctgg ctccggcacc gacttcaccc tgaccatcga ctcccctcag     660
cctgaggact ccgccaccta ctactgccag cagtccgccc acttccctat caccttcggc     720
cagggaaccc ggctggaaat caaggctagc accaagggcc catcggtctt ccccctggcg     780
ccctgctcca ggagcacctc cgagagcaca gcggccctgg gctgcctggt caaggactac     840
ttccccgaac cggtgacggt gtcgtggaac tcaggcgctc tgaccagcgg cgtgcacacc     900
ttccagctg tcctacagtc ctcaggactc tactccctca gcagcgtggt gaccgtgccc      960
tccagcaact tcggcaccca gacctacacc tgcaacgtag atcacaagcc cagcaacacc    1020
aaggtggaca gacagttga gcccaaatct tctgacaaaa ctcacacatg cccaccgtgc     1080
ccagcacctg aagcagctgg ggaccgtca gtcttcctct ccccccaaa acccaaggac      1140
accctcatga tctcccggac ccctgaggtc acatgcgtgg tggtggacgt gagccacgaa    1200
gaccctgagg tcaagttcaa ctggtacgtg gacggcgtgg aggtgcataa tgccaagaca    1260
aagccgcggg aggagcagta caacagcacg taccgtgtgg tcagcgtcct caccgtcctg    1320
caccaggact ggctgaatgg caaggagtac aagtgcaagg tctccaacaa agccctccca    1380
gcccccatcg agaaaaccat ctccaaagcc aaagggcagc ccgagaacc acaggtgtac     1440
accctgcccc catcccggga ggagatgacc aagaaccagg tcagcctgac ctgcctggtc    1500
```

```
aaaggcttct atcccagcga catcgccgtg gagtgggaga gcaatgggca gccggagaac    1560
aactacgaca ccacgcctcc cgtgctggac tccgacggct ccttcttcct ctatagcgac    1620
ctcaccgtgg acaagagcag gtggcagcag gggaacgtct tctcatgctc cgtgatgcat    1680
gaggctctgc acaaccacta cacgcagaag agcctctccc tgtctccggg taaatag      1737
```

```
<210> SEQ ID NO 96
<211> LENGTH: 585
<212> TYPE: PRT
<213> ORGANISM: Artificial Sequence
<220> FEATURE:
<223> OTHER INFORMATION: Synthetic polypeptide

<400> SEQUENCE: 96
```

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gln Thr Val Val Thr Gln Glu Pro Ser Leu Thr Val
    130                 135                 140

Ser Pro Gly Gly Thr Val Thr Leu Thr Cys Gly Ser Ser Thr Gly Ala
145                 150                 155                 160

Val Thr Ser Gly Asn Tyr Pro Asn Trp Val Gln Gln Lys Pro Gly Gln
                165                 170                 175

Ala Pro Arg Gly Leu Ile Gly Gly Thr Lys Phe Leu Ala Pro Gly Thr
            180                 185                 190

Pro Ala Arg Phe Ser Gly Ser Leu Leu Gly Gly Lys Ala Ala Leu Thr
        195                 200                 205

Leu Ser Gly Val Gln Pro Glu Asp Glu Ala Glu Tyr Tyr Cys Val Leu
    210                 215                 220

Trp Tyr Ser Asn Arg Trp Val Phe Gly Gly Gly Thr Lys Leu Thr Val
225                 230                 235                 240

Leu Gly Gln Pro Lys Ala Ala Pro Ser Val Thr Leu Phe Pro Pro Ser
                245                 250                 255

Ser Glu Glu Leu Gln Ala Asn Lys Ala Thr Leu Val Cys Leu Ile Ser
            260                 265                 270

Asp Phe Tyr Pro Gly Ala Val Thr Val Ala Trp Lys Ala Asp Ser Ser
        275                 280                 285

Pro Val Lys Ala Gly Val Glu Thr Thr Thr Pro Ser Lys Gln Ser Asn
    290                 295                 300

Asn Lys Tyr Ala Ala Ser Ser Tyr Leu Ser Leu Thr Pro Glu Gln Trp
305                 310                 315                 320
```

-continued

```
Lys Ser His Arg Ser Tyr Ser Cys Gln Val Thr His Glu Gly Ser Thr
            325                 330                 335

Val Glu Lys Thr Val Ala Pro Thr Glu Cys Ser Glu Pro Lys Ser Ser
        340                 345                 350

Asp Lys Thr His Thr Cys Pro Pro Cys Pro Ala Pro Glu Ala Ala Gly
        355                 360                 365

Gly Pro Ser Val Phe Leu Phe Pro Pro Lys Pro Lys Asp Thr Leu Met
        370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
        450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Lys Glu Met Thr Lys Asn Gln Val Ser
                485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
        515                 520                 525

Val Leu Lys Ser Asp Gly Ser Phe Phe Leu Tyr Ser Lys Leu Thr Val
        530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
                565                 570                 575

Pro Gly Lys His His His His His
            580                 585
```

<210> SEQ ID NO 97
<211> LENGTH: 1758
<212> TYPE: DNA
<213> ORGANISM: Artificial Sequence
<220> FEATURE:
<223> OTHER INFORMATION: Synthetic polynucleotide

<400> SEQUENCE: 97

```
caggtgcagc tggtgcagtc tggcgccgaa gtgaagaaac tggagagtc tgtcaaagtc        60 agctgcaagg cctccggcta caccttcacc aactacggca tgaactgggt gaaacaggct      120
ccaggacagg gactcgagtg gatgggctgg atcaacacct acaccggcga gcctacctac      180
gccgacaagt tccagggcag agtgaccatg accaccgaca tctaccagca cagcttac        240 atggaaatcc ggaacctggg cggcgacgac accgccgtgt actactgcgc ccggtggtct      300
tggtccgacg gctactacgt gtacttcgac tactggggcc agggcacctc cgtgacagtg      360
tccagcggag gcggcggttc aggcggaggt ggctctcaga ccgtggtcac caggaacct       420 tctctgaccg tcagtcccgg cggaaccgtg accctgacct gtggctcctc taccggcgct      480
gtgacctccg gcaactaccc taactgggtg cagcagaaac ccggccaggc tcccagagga      540
```

```
ctcatcggcg gcaccaagtt tctggcccct ggcacccctg ccagattctc tggctccctg    600
ctgggcggca aggctgctct gaccctgagc ggagtccagc cagaggacga ggccgagtac    660
tactgtgtgc tgtggtactc aacagatgg gtgttcggcg gtggcaccaa gctgaccgtg    720
ctgggtcagc ccaaggctgc cccctcggtc actctgttcc cgccctcctc tgaggagctt    780
caagccaaca aggccacact ggtgtgtctc ataagtgact tctacccggg agccgtgaca    840
gtggcctgga aggcagatag cagccccgtc aaggcgggag tggagaccac cacaccctcc    900
aaacaaagca acaacaagta cgcggccagc agctatctga gcctgacgcc tgagcagtgg    960
aagtcccaca gaagctacag ctgccaggtc acgcatgaag ggagcaccgt ggagaagaca   1020
gtggccccta cagaatgttc agagcccaaa tcttctgaca aaactcacac atgccccccg   1080
tgcccagcac ctgaagcagc tgggggaccg tcagtcttcc tcttcccccc aaaacccaag   1140
gacaccctca tgatctcccg gacccctgag gtcacatgcg tggtggtgga cgtgagccac   1200
gaagaccctg aggtcaagtt caactggtac gtggacggcg tggaggtgca taatgccaag   1260
acaaagccgc gagaggagca gtacaacagc acgtaccgtg tggtcagcgt cctcaccgtc   1320
ctgcaccagg actggctgaa tggcaaggag tacaagtgca aggtctccaa caaagccctc   1380
ccagccccca tcgagaaaac catctccaaa gccaaagggc agccccgaga accacaggtg   1440
tacaccctgc ccccatcccg gaaggagatg accaagaacc aggtcagcct gacctgcctg   1500
gtcaaaggct tctatcccag cgacatcgcc gtggagtggg agagcaatgg gcagccggag   1560
aacaactaca agaccacgcc tcccgtgctg aagtccgacg gctccttctt cctctatagc   1620
aagctcaccg tggacaagag caggtggcag caggggaacg tcttctcatg ctccgtgatg   1680
catgaggctc tgcacaacca ctacacgcag aagagcctct ccctgtctcc gggtaaacat   1740
catcatcatc atcattaa                                                 1758
```